(12) United States Patent
Pellecchia et al.

(10) Patent No.: US 8,937,193 B2
(45) Date of Patent: Jan. 20, 2015

(54) APOGOSSYPOLONE DERIVATIVES AS ANTICANCER AGENTS

(75) Inventors: Maurizio Pellecchia, La Jolla, CA (US); Jun Wei, La Jolla, CA (US)

(73) Assignee: Sanford-Burnham Medical Research Institute, La Jolla, CA (US)

( * ) Notice: Subject to any disclaimer, the term of this patent is extended or adjusted under 35 U.S.C. 154(b) by 623 days.

(21) Appl. No.: 12/900,378

(22) Filed: Oct. 7, 2010

(65) Prior Publication Data

US 2011/0112112 A1    May 12, 2011

Related U.S. Application Data

(60) Provisional application No. 61/249,982, filed on Oct. 8, 2009.

(51) Int. Cl.
*C07C 50/12* (2006.01)
*C07C 50/10* (2006.01)
*C07C 235/84* (2006.01)

(52) U.S. Cl.
CPC ............... *C07C 50/10* (2013.01); *C07C 235/84* (2013.01); *G01N 2510/00* (2013.01); *G01N 2800/52* (2013.01)
USPC ............ 552/296; 552/297; 552/298; 552/299

(58) Field of Classification Search
USPC .................................. 552/296, 297, 298, 299
See application file for complete search history.

(56) References Cited

U.S. PATENT DOCUMENTS

| | | | |
|---|---|---|---|
| 4,559,157 A | 12/1985 | Smith et al. | |
| 4,608,392 A | 8/1986 | Jacquet et al. | |
| 4,820,508 A | 4/1989 | Wortzman | |
| 4,938,949 A | 7/1990 | Borch et al. | |
| 4,992,478 A | 2/1991 | Geria | |
| 7,223,395 B2 | 5/2007 | Muller et al. | |
| RE40,862 E | 7/2009 | Flack et al. | |
| 2003/0008924 A1 | 1/2003 | Wang et al. | |
| 2009/0105319 A1 | 4/2009 | Pellecchia et al. | |
| 2009/0118377 A1 | 5/2009 | Wang et al. | |

FOREIGN PATENT DOCUMENTS

| | | |
|---|---|---|
| EP | 1704136 B1 | 9/2006 |
| WO | WO 2005/009434 A2 | 2/2005 |
| WO | WO 2005/073158 A1 | 8/2005 |
| WO | WO 2006/050447 A2 | 5/2006 |

OTHER PUBLICATIONS

Youle et al., "The BCL-2 protein family: opposing activities that mediate cell death." Nature, vol. 9, pp. 47-59, 2008.*
Arnold et al., "Preclinical studies of Apogossypolone: a new nonpeptidic pan small-molecule inhibitor of BCL-2, BCL-XL and Mcl-1 proteins in Follicular Small Cleaved Cell Lymphoma model", Mol. Cancer., 7(20):1-10 (2008).
Baumgrass et al., "Reversible inhibition of calcineurin by the polyphenolic aldehyde gossypol", J. Biol. Chem., 276(51):47914-47921 (2001).
Emadi et al., "A chemical genetic screen for modulators of asymmetrical 2,2'-dimeric naphthoquinones cytotoxicity in yeast", PLoS One, 5(5):e10846 (2010).
Enyedy et al, "Discovery of small-molecule inhibitors of Bcl-2 through structure-based computer screening", J. Med. Chem., 44(25):4313-4324 (2001).
Garcia-Echeverria and Sellers, "Drug discovery approaches targeting the PI3K/Akt pathway in cancer", Oncogene, 27(41):5511-5526 (2008).
Laatsch H., "Synthese and Eigenschaften cyclopropanierter 2,2'-Binaphthyldichinone" = "Synthesis & properties of cyclopropanated 2,2'-binaphthoquinones", Z. Naturforsch, 45b 1037-1042 (1990).
Stagliano et al., "Effect of methoxyl group position on the regioselectivity of ammonia substitution reactions involving 3,3'-dichloro-2,2'-binaphthoquinones", J. Org. Chem., 69(15):5128-5131 (2004).
Takeya et al., "Aerobic oxidative dimerization of 1-naphthols to 2,2'-binaphthoquinones mediated by SnCl4 and its application to natural product synthesis", Tetrahedron, 60(41):pp. 9049-9060 (2004).
Tanoue et al., "A facile synthesis of naturally occurring binaphthoquinones: efficient oxidative dimerization of 4-alkoxy-1-naphthols using silver(II) oxide-40% nitric acid", Tetrahedron, 58(1), 99-104 (2002).
Yu et al., "A new method for the synthesis of 2-hydroxy-3-nitro-1,4-naphthoquinones: application to regiospecific preparation of unsymmetrical nitrobiquinones", J. Org. Chem., 71(17):6648-6651 (2006).
Yu M., "Methodology development for regiocontrolled synthesis of bis and trimeric quinone derivatives of conocurvone", Ph.D. Thesis, Illinois Institute of Technology, UMI 2006. < http://gradworks.umi.com/32/20/3220890.html >.

(Continued)

Primary Examiner — Barbara P Badio
(74) Attorney, Agent, or Firm — Wilson Sonsini Goodrich & Rosati

(57) ABSTRACT

The disclosure provides compounds and methods of using Apogossypolone derivatives for treating diseases and disorders. In particular, the disclosure provides compounds of Formula I:

or a pharmaceutically acceptable salt, hydrate, or solvate thereof, and provides methods for the preparation of compounds of Formula I; and methods for treating cancer, autoimmune diseases, and inflammation by administering a compound of Formula I.

11 Claims, 25 Drawing Sheets

(56) References Cited

OTHER PUBLICATIONS

Adams, et al. Apogossypol and its degradation products. J. Am. Chem. Soc. 1938; 60: 2174-2180.

Becattini, et al. Rational design and real time, in-cell detection of the proapoptotic activity of a novel compound targeting Bcl-X(L). Chemistry & biology. 2004; 11: 389-95.

Brunko, et al. Studies leading to potent, dual inhibitors of Bcl-2 and Bcl xL. J. Med. Chem. 2007; 50: 641-662.

Coward, et al. Quantitative determination of Apogossypol, a proapoptotic analog of Gossypol, in mouse plasma using LC/MS/MS. Journal of pharmaceutical and biomedical analysis. 2006; 42: 581-586.

Dao, et al. Synthesis and cytotoxicity of Gossypol related compounds. Eur J Med Chem. 2000; 35: 805-813.

Du, et al. Synthesis of N-substituted indole derivatives via PIFA-mediated intramolecular cyclization. Org. Lett. 2006; 8: 5919-5922.

Hu, et al. ApoG2, a novel inhibitor of antiapoptotic Bcl-2 family proteins, induces apoptosis and suppresses tumor growth in nasopharyngeal carcinoma xenografts. Int J Cancer. 2008; 123: 2418-2429.

Islam, et al. Structure-activity studies of antitumor agents based on pyrrolo[1,2-a]benzimidazoles: new reductive alkylating DNA cleaving agents. J Med Chem 1991; 34: 2954-2961.

Jun Wei, et al. Apogossypol derivatives as antagonists of antiapoptotic Bcl-2 family proteins. Mol Cancer Ther. Apr. 2009; 8(4): 904-913.

Kitada, et al. Bcl-2 antagonist Apogossypol (NSC736630) displays single-agent activity in Bcl-2-transgenic mice and has superior efficacy with less toxicity compared with Gossypol (NSC19048). Blood. 2008; 3: 3211-3249.

Kitada, et al. Discovery, characterization, and structure-activity relationships studies of proapoptotic polyphenols targeting B-celllymphocyte/leukemia-2 proteins. Journal of medicinal chemistry. 2003; 46: 4259-4264.

Li, et al. A small molecule pan-Bcl-2 family inhibitor, GX15-070, induces apoptosis and enhances cisplatin-induced apoptosis in non-small cell lung cancer cells. Cancer Chemother Pharmacol. 2008; 61: 525-534.

Lin, et al. [Effect of Apogossypolone on induction apoptosis in multiple myeloma cells and its mechanisms]. Zhongguo shi yan xue ye xue za zhi I Zhongguo bing li sheng li xue hui = Journal of experimental hematology I Chinese Association of Pathophysiology 2009; 17: 92-98. (abstract only).

Meltzer, et al. Regioselective Route to Gossypol Analogues: The Synthesis of Gossypol and 5,5'-Didesisopropyl-5,5'-diethylgossypol. J. Org. Chem. 1985; 50: 3121-3124.

Meng, et al. Natural BH3 mimetic (−)-gossypol chemosensitizes human prostate cancer via Bcl-xL inhibition accompanied by increase of Puma and Noxa. Mol Cancer Ther. 2008; 7: 2192-2202.

Mi, et al. Synergistic antitumoral activity and induction of apoptosis by novel pan Bcl-2 proteins inhibitor Apogossypolone with adriamycin in human hepatocellular carcinoma. Acta Pharmacal. Sin. 2008; 29: 1467-1477.

Mohammad, et al. Preclinical studies of a nonpeptidic small-molecule inhibitor of Bcl-2 and Bcl-X(L) [(−) gossypol] against diffuse large cell lymphoma. Mol Cancer. Ther. 2005; 4: 13-21.

Oliver, et al. (−)—Gossypol acts directly on the mitochondria to overcome Bcl-2- and Bcl-X(L)-mediated apoptosis resistance. Mol. Cancer Ther. 2005; 4: 23-31.

Oltersdorf, et al. An inhibitor of Bcl-2 family proteins induces regression of solid tumours. Nature. 2005; 435: 677-681.

Rega, et al. Structure-based discovery of a new class of Bcl-xL antagonists. Bioorg. Chem. 2007; 35; 344-353.

Royer, et al. Synthesis and anti-HIV activity of 1,1'-dideoxygossypol and related compounds. J. Med. Chem. 1995; 38: 2427-2432.

Sakamoto, et al. Probing substrate binding site of the *Escherichia coli* quinol oxidases using synthetic ubiquinol analogues. J. Biol. Chem. 1996; 271: 29897-29902.

Shelley, et al. Stereo-specific cytotoxic effects of Gossypol enantiomers and Gossypolone in tumour cell lines. Cancer letters. 1999; 135: 171-180.

Sun, et al. Apogossypolone inhibits cell growth by inducing cell cycle arrest in U937 cells. Oncology reports. 2009; 22: 193-198.

Tang, et al. Structure-based design of flavonoid compounds as a new class of small-molecule inhibitors of the anti-apoptotic Bcl-2 proteins. J. Med. Chem. 2007; 50: 3163-3166.

Wang, et al. Structure-based design of potent small molecule inhibitors of antiapoptotic Bcl-2 proteins. Journal of medicinal chemistry. 2006; 49: 6139-6142.

Wei et al. Apogossypol derivatives as pan-active inhibitors of antiapoptotic B-cell lymphoma/leukemia-2 (Bcl-2) family proteins. J Med Chem. Jul. 23, 2009;52(14):4511-4523.

Wei, et al. BI-97C1, an optically pure Apogossypol derivative as pan-active inhibitor of antiapoptotic B-cell lymphoma/leukemia-2 (Bcl-2) family proteins. J Med Chem. 2010; 53: 4166-4176.

Wei, et al. Synthesis and evaluation of Apogossypol atropisomers as potential Bcl-xL antagonists. Cancer Lett. 2009; 273: 107-113.

Yamanoi, et al.. Direct and selective arylation of tertiary silanes with rhodium catalyst. J. Org. Chem. 2008; 73: 6671-6678.

Zhang, et al. Molecular mechanism of Gossypol-induced cell growth inhibition and cell death of HT-29 human colon carcinoma cells. Biochemical Pharmacology. 2003; 66: 93-103.

Adams et al., The Bcl-2 protein family: arbiters of cell survival. Science (New York, NY) 1998, 281:1322-6.

Brien et al., Down regulation ofBfl-1 protein expression sensitizes malignant B cells to apoptosis. Oncogene 2007, 26:5828-32.

CA2773576 Office Action dated Dec. 6, 2013.

Cory et al., Killing cancer cells by flipping the Bcl-2/Bax switch. Cancer cell 2005, 8:5-6.

Degterev et al., Identification of small-molecule inhibitors of interaction between the BH3 domain and Bcl-xL. Nat Cell Biol2001, 3:173-82.

Eldridge et al., Empirical scoring functions: I. The development of a fast empirical scoring function to estimate the binding affinity of ligands in receptor complexes. J Comput Aided Mol Des 1997, 11:425-445.

Ferreira et al., Chemotherapy triggers apoptosis in a caspase-8-dependent and mitochondria-controlled manner in the non-small cell lung cancer cell line NCI-H460. Cancer Res 2000, 60:7133-41.

Gross et al., BCL-2 family members and the mitochondria in apoptosis. Genes & development 1999, 13:1899-911.

Johnstone et al., Apoptosis: a link between cancer genetics and chemotherapy. Cell 2002, 108:153-64.

Jones et al., Development and validation of a genetic algorithm for flexible docking. Journal of molecular biology 1997, 267:727-748. Abstract only.

Katsumata et al., Differential effects ofBcl-2 on T and B cells in transgenic mice. Proc Natl Acad Sci US A 1992, 89:11376-11380.

PCT/2010/051845 International Search Report & Written Opinion dated Mar. 29, 2011.

PCT/2010/051845 International Preliminary Report on Patentability dated Apr. 19, 2012.

Ramjaun et al, Upregulation of two BH3-only proteins, Bmf and Bim, during TGF beta-induced apoptosis. Oncogene 2007, 26:970-981.

Reed, Apoptosis-based therapies. Nature reviews Drug discovery 2002, 1:111-21.

Reed, Bcl-2 family proteins. Oncogene 1998, 17:3225-36.

Reed, Bcl-2 family proteins: strategies for overcoming chemoresistance in cancer. Advances in pharmacology (San Diego, Calif) 1997, 41 501-32.

Reed, Dysregulation of apoptosis in cancer, J Clin Oncol., 1999, 17:2941-53.

Reed, Molecular biology of chronic lymphocytic leukemia: implications for therapy, Seminars in hematology 1998, 35:3-13.

Sattler et al., Structure of Bcl-xL-Bak peptide complex: recognition between regulators of apoptosis. Science (New York, NY) 1997, 275:983-986.

Teschner et al., Texture mapping: a new tool for molecular graphics. J Mol Graph 1994, 12:98-105.

Vaux et al., Cell death in development. Cel/1999, 96:245-54.

(56) References Cited

OTHER PUBLICATIONS

Voortman et al., Bortezomib, but not cisplatin, induces mitochondria-dependent apoptosis accompanied by up-regulation of noxa in the non-small cell lung cancer cell line NCI-H460. Mol Cancer Ther 2007, 6:1046-53.

Wang et al., Structure-based discovery of an organic compound that binds Bcl-2 protein and induces apoptosis of tumor cells. Proceedings of the National Academy of Sciences of the United States of America 2000, 97:7124-9.

Wei et al., Proapoptotic BAX and BAK: a requisite gateway to mitochondrial dysfunction and death. Science (New York, NY) 2001, 292:727-30.

Wesarg et al., Targeting BCL-2 family proteins to overcome drug resistance in non-small cell lung cancer. Int J Cancer 2007, 121:2387-94.

White et al., Antibody-targeted immunotherapy for treatment of malignancy., Annu. Rev. Med., 52:125 (2001).

Zhai et al., Gambogic acid is an antagonist of antiapoptotic Bcl-2 family proteins. Mol Cancer Ther 2008, 7:1639-46.

* cited by examiner 1 (Gossypol)($R_1$ = CHO; $R_2$ = isopropyl)
2a (Apogossypol)($R_1$ =H; $R_2$ = isopropyl)
3a (BI79D10)($R_1$ =H; $R_2$ = $COCH_2Ph$)
4a (8r)($R_1$ = h; $R_2$ = $CONHCH_2CH(CH)_3Ph$)

5 (Gossypolone)($R_1$ = CHO; $R_2$ = isopropyl)
6a (Apogossypolone)($R_1$ = H; $R_2$ = isopropyl)
7 ($R_1$ =H; $R_2$ = $COCH_2Ph$)
8a ($R_1$ =H; $R_2$ = $CONH_2CH(CH)_3Ph$)

A

Gossypol (1) (R₁ = CHO; R₂ = isopropyl)
Apogossypol (2) (R₁ = H; R₂ = isopropyl)
BI79D10 (3) (R₁ = H; R = COCH₂Ph)

B 5, 5' Substituted Apogossypol
Ketone derivatives (R = COR)
Amide derivatives (R = CONHR)
Alkyl derivatives (R = alkyl groups)

C

D

SEQUENCE LISTING

<160> NUMBER OF SEQ ID NOS: 1

<210> SEQ ID NO 1
<211> LENGTH: 16
<212> TYPE: PRT
<213> ORGANISM: Artificial Sequence
<220> FEATURE:
<223> OTHER INFORMATION: Synthetic construct

<400> SEQUENCE: 1

Gly Gln Val Gly Arg Gln Leu Ala Ile Ile Gly Asp Asp Ile Asn Arg
1               5                   10                  15

APOGOSSYPOLONE DERIVATIVES AS ANTICANCER AGENTS

CROSS REFERENCE TO RELATED APPLICATION

This application is based on and claims benefit of priority benefit under 35 U.S.C. §119(e) to U.S. Provisional Application No. 61/249,982 filed on Oct. 8, 2009, the disclosure of which is hereby incorporated by reference in its entirety for all purposes.

GRANT INFORMATION

This invention was made in part with government support under NCI-U19, CA113319, and CA149668. The Government has certain rights in the invention.

FIELD OF THE DISCLOSURE

The disclosure relates generally to Apogossypolone (APOG2) and derivatives thereof, and more specifically, to the use of APOG2 and derivatives thereof, in treating cancer, autoimmune diseases, and/or inflammation.

BACKGROUND OF THE DISCLOSURE

The apoptotic cascade in cells is known to lead to cell death. When anti-apoptotic proteins, such as BCL-2 (B-cell lymphoma/leukemia-2) family proteins, are overproduced by the cells, uncontrollable cell growth may ensue, potentially leading to the development of various serious diseases, disorders, and pathologies, particularly cancer. Programmed cell-death (apoptosis) plays a critical role in the maintenance of normal tissue homeostasis, ensuring a proper balance of cell production and cell loss. Defects in the regulation of programmed cell death promote tumorgenesis, and also contribute significantly to chemoresistance. Bcl-2 family proteins are central regulators of apoptosis. Over-expression of anti-apoptotic Bcl-2 family proteins occurs in many human cancers and leukemias and therefore, these proteins are very attractive targets for the development of novel anticancer agents. In humans, six anti-apoptotic members of the Bcl-2 family have been identified and characterized thus far, including Bcl-2, Bcl-$X_L$, Mcl-1, Bfl-1, Bcl-W and Bcl-B. Members of the Bcl-2 family proteins also include pro-apoptotic effectors such as Bak, Bax, Bad, Bim and Bid. Anti-apoptotic and pro-apoptotic Bcl-2 family proteins dimerize and negate each other's functions. Structural studies have elucidated a hydrophobic crevice on the surface of anti-apoptotic Bcl-2 family proteins that binds the BH3 dimerization domain of pro-apoptotic family members. Thus, molecules that mimic the BH3 domain of pro-apoptotic proteins may induce apoptosis and/or abrogate the ability of anti-apoptotic Bcl-2 proteins to inhibit cancer cell death.

Apoptosis plays a role in tissue homeostatis, for example, in the physiological removal of unwanted cells during development and in host defense mechanism. The BCL-2 family of proteins are believed to be involved in regulating of apoptosis. Specifically, members of the BCL-2 gene family can act to inhibit programmed cell death (e.g., BCL-2, BCL-$X_L$, and ced-9) or promote cell death (e.g., Bax, Bak, and BCL-$X_S$). Pro-survival members of this family, such as BCL-$X_L$, contain on the surface, a hydrophobic groove, which is believed to allow binding of the BH3 domain of the pro-apoptotic counterpart. This binding is believed to play a role in apoptosis regulation, in fact pro- and anti-survival proteins can reverse each others function through dimerization. Various potential BCL-2 antagonists have been previously identified that inhibit anti-apoptotic proteins, such as the BCL-2 family proteins. However, none of these compounds inhibit all six proteins in the BCL-2 family, i.e., all of the following proteins: BCL-$X_L$, BCL-2, BCL-W, BCL-B, BFL-1, and MCL-1. For example, none of the previously identified synthetic BCL-2 antagonists were effective in inhibiting the protein BFL-1. In addition, the existing antagonists are characterized by other drawbacks, such as lack of efficacy or safety issues.

It has been previously shown that the natural product Gossypol, shown on FIGS. 1 and 2, is an inhibitor of BCL-2, BCL-$X_L$ and MCL-1, and functions as a BH3 mimic. (−)Gossy-pol is currently in phase II clinical trails, displaying single-agent antitumor activity in patients with advanced malignancies. Given that Gossypol has toxicity problems likely due to it's two reactive aldehyde groups, Apogossypol was prepared. Apogossypol lacks these aldehydes but retains activity against anti-apoptotic BCL-2 family proteins in vitro and in cells. The efficacy and toxicity in mice of Gossypol and Apogossypol have been compared. Preclinical in vivo data show that Apogossypol has better efficacy and reduced toxicity compared to Gossypol, as well as better single-dose pharmacokinetic characteristics, including, superior blood concentrations over time compared to Gossypol, due to slower clearance. Recently, the separation and characterization of atropoisomers of Apogossypolone was accomplished, in which it was shown that racemic Apogossypolone is as effective as its individual isomers. Further, the synthesis and evaluation of several 5,5' alkyl, ketone and amide substituted Apogossypolone derivatives, as well as the preparation of the optically pure compound, which had improved in vitro and in vivo efficacy, was reported. These observations indicate that Apogossypol and its deriviatives, may be promising lead compounds for cancer therapy.

BCL-2 family members are also believed to be involved in inflammatory disorders. For example, BCL-2 family members have been shown to play roles in neutrophil apoptosis and inflammatory accumulation. In several inflammatory diseases, the delay of neutrophil apoptosis is associated with reduced levels of the pro-apoptotic BCL-2 family member BAX. It has also been shown that eosinophils isolated from children with acute asthma have an increased expression of the anti-apoptotic protein BCL-2, which was inversely correlated with expiratory flow rate. BCL-2 family proteins are also associated with Crohn's disease. BAX expression is attenuated and BCL-$X_L$ expression is increased in T cells isolated from the lamina propria from patients with Crohn's disease. This shows that inflammatory cell survival, by means of prosurvival and anti-apoptotic signaling mechanisms, are involved in the pathogenesis of inflammatory diseases. Lupus is a complex systemic autoimmune disease, characterized by high levels of anti-DNA and anti-glomerular autoantibodies, activated B and T-cells, and glomerulonephritis. Neutrophils from lupus-susceptible mice display reduced rates of apoptosis. The decreased apoptosis is associated with the altered expression of BCL-2 family proteins contributing to the greater accumulation of neutrophils in the lupus-susceptible mice. Signaling studies using several different lupus strains indicate that multiple signaling pathways are upregulated in lymphocytes and non lymphocytes as disease evolves, including the activation of BCL-2 and BCL-$X_L$. These anti-apoptotic molecules are known to prolong the lifespan of all cells, including autoreactive B and T cells.

Thus, in view of these considerations, there remains a need in the art for improved antagonists of anti-apoptotic proteins including the BCL-2 family.

SUMMARY OF THE DISCLOSURE

Overexpression of anti-apoptotic Bcl-2 family proteins is commonly related with tumor maintenance, progression, and chemoresistance. Inhibition of these anti-apoptotic proteins is an attractive approach for cancer therapy. Apogossypol and its derivatives were evaluated as anti-cancer agents for their ability to induce apoptosis via the inhibition of anti-apototic Bcl-2 family proteins. The oxidation product of Apogossypol results in Apogossypolone, which has been shown to retain some of the anticancer properties in cell cultures and mice models of Apogossypol, but has reduced anti-Bcl-2 activity in vitro. Guided by nuclear magnetic resonance (NMR) binding assays, a series of 5,5' substituted Apogossypolone derivatives were synthesized and pan-active antagonists of anti-apoptotic Bcl-2 family proteins were identified with binding potency in the low micromolar to nanomolar range. Thus, the present disclosure provides novel Apogossypolone derivatives, which exhibit improved in vitro and in vivo activity.

According to one aspect, the disclosure provides compounds having Formula I:

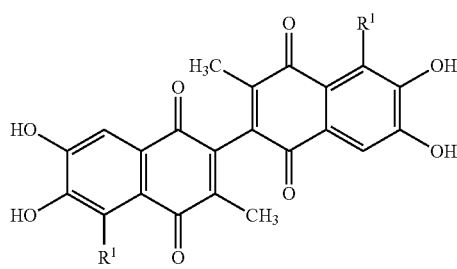

or a pharmaceutically acceptable salt, hydrate, or solvate thereof, wherein:

$R^1$ is independently hydrogen, halogen, amino, nitro, cyano, hydroxyl, substituted or unsubstituted alkyl, substituted or unsubstituted cycloalkyl, perfluoroalkyl, substituted or unsubstituted alkenyl, substituted or unsubstituted alkynyl, substituted or unsubstituted alkoxy, substituted or unsubstituted heteroalkyl, substituted or unsubstituted heterocyclic, substituted or unsubstituted aryl, substituted or unsubstituted arylalkyl, substituted or unsubstituted heteroaryl, substituted or unsubstituted heteroarylalkyl, $—(CH_2)_jOR^2$, $—(CH_2)_jC(O)R^2$, $—(CH_2)_jC(O)OR^2$, $—(CH_2)_jOC(O)R^2$, $—(CH_2)_jNR^3R^4$, $—(CH_2)_jC(O)NR^3R^4$, $—(CH_2)_jC(O)NR^3R^4$, $—(CH_2)_jNR^5C(O)R^2$, $—(CH_2)_jNR^5C(O)OR^2$, $—(CH_2)_jNR^5C(O)NR^3R^4$, $—(CH_2)_jS(O)_mR^6$, or $—(CH_2)_jNR^5S(O)_mR^6$, wherein j is an integer from 0 to 12; and m is an integer from 0 to 2;

$R^2$ is independently hydrogen, substituted or unsubstituted alkyl, substituted or unsubstituted cycloalkyl, perfluoroalkyl, substituted or unsubstituted alkenyl, substituted or unsubstituted alkynyl, substituted or unsubstituted heteroalkyl, substituted or unsubstituted heterocyclic, substituted or unsubstituted aryl, substituted or unsubstituted arylalkyl, substituted or unsubstituted heteroaryl, substituted or unsubstituted heteroarylalkyl;

$R^3$ and $R^4$ are each independently hydrogen, substituted or unsubstituted alkyl, substituted or unsubstituted cycloalkyl, perfluoroalkyl, substituted or unsubstituted alkenyl, substituted or unsubstituted alkynyl, substituted or unsubstituted heteroalkyl, substituted or unsubstituted heterocyclic, substituted or unsubstituted aryl, substituted or unsubstituted arylalkyl, substituted or unsubstituted heteroaryl, substituted or unsubstituted heteroarylalkyl, or $R^3$ and $R^4$, together with the N atom to which they are attached, form substituted or unsubstituted heterocyclic, or substituted or unsubstituted heteroaryl;

$R^5$ is independently hydrogen, substituted or unsubstituted alkyl, substituted or unsubstituted cycloalkyl, perfluoroalkyl, substituted or unsubstituted alkenyl, substituted or unsubstituted alkynyl, substituted or unsubstituted heteroalkyl, substituted or unsubstituted heterocyclic, substituted or unsubstituted aryl, substituted or unsubstituted arylalkyl, substituted or unsubstituted heteroaryl, substituted or unsubstituted heteroarylalkyl;

$R^6$ is independently hydrogen, substituted or unsubstituted alkyl, substituted or unsubstituted cycloalkyl, perfluoroalkyl, substituted or unsubstituted alkenyl, substituted or unsubstituted alkynyl, substituted or unsubstituted heteroalkyl, substituted or unsubstituted heterocyclic, substituted or unsubstituted aryl, substituted or unsubstituted arylalkyl, substituted or unsubstituted heteroaryl, substituted or unsubstituted heteroarylalkyl;

R, $R^1$, $R^2$, $R^3$, $R^4$, $R^5$, and $R^6$ may be optionally independently substituted with 1 to 3 groups selected from hydrogen, halogen, amino, nitro, cyano, hydroxyl, alkyl, cycloalkyl, perfluoroalkyl, alkenyl, alkynyl, alkoxy, heteroalkyl, heterocyclic, aryl, arylalkyl, heteroaryl, heteroarylalkyl, $—(CH_2)_jOR^7$, $—(CH_2)_jC(O)R^7$, $—(CH_2)_jC(O)OR^7$, $—(CH_2)_jOC(O)R^7$, $—(CH_2))NR^8R^9$, $—(CH_2)_jC(O)NR^8R^9$, $—(CH_2)_jOC(O)NR^8R^9$, $—(CH_2)_jNR^{10}C(O)R^7$, $—(CH_2)_jNR^{10}C(O)OR^7$, $—(CH_2)_jNR^{10}C(O)NR^8R^9$, $—(CH_2)_jS(O)_mR^{11}$, or $—(CH_2)_jNR^{10}S(O)_mR^{11}$, wherein j is an integer from 0 to 12; and m is an integer from 0 to 2;

$R^7$ is independently hydrogen, alkyl, cycloalkyl, perfluoroalkyl, alkenyl, alkynyl, heteroalkyl, heterocyclic, aryl, arylalkyl, heteroaryl, or heteroarylalkyl;

$R^8$ and $R^9$ are each independently hydrogen, alkyl, cycloalkyl, perfluoroalkyl, alkenyl, alkynyl, heteroalkyl, heterocyclic, aryl, arylalkyl, heteroaryl, heteroarylalkyl, or $R^8$ and $R^9$, together with the N atom to which they are attached, form heterocyclic or heteroaryl;

$R^{10}$ is independently hydrogen, alkyl, cycloalkyl, perfluoroalkyl, alkenyl, alkynyl, heteroalkyl, heterocyclic, aryl, arylalkyl, heteroaryl, or heteroarylalkyl; and $R^{11}$ is independently hydrogen, alkyl, cycloalkyl, perfluoroalkyl, alkenyl, alkynyl, heteroalkyl, heterocyclic, aryl, arylalkyl, heteroaryl, or heteroarylalkyl; and with the provision that $R^1$ is not isopropyl.

In another aspect, the disclosure provides methods for treating diseases and/or disorders including cancers, for example, lung cancer, breast cancer, prostate cancer, and lymphomoas, autoimmune diseases, inflammation, and the like, by administering to a subject in need thereof a therapeutically effective amount of a compound of Formula I, thereby treating the disease or the disorder.

DETAILED DESCRIPTION OF THE DISCLOSURE

Figure 1:
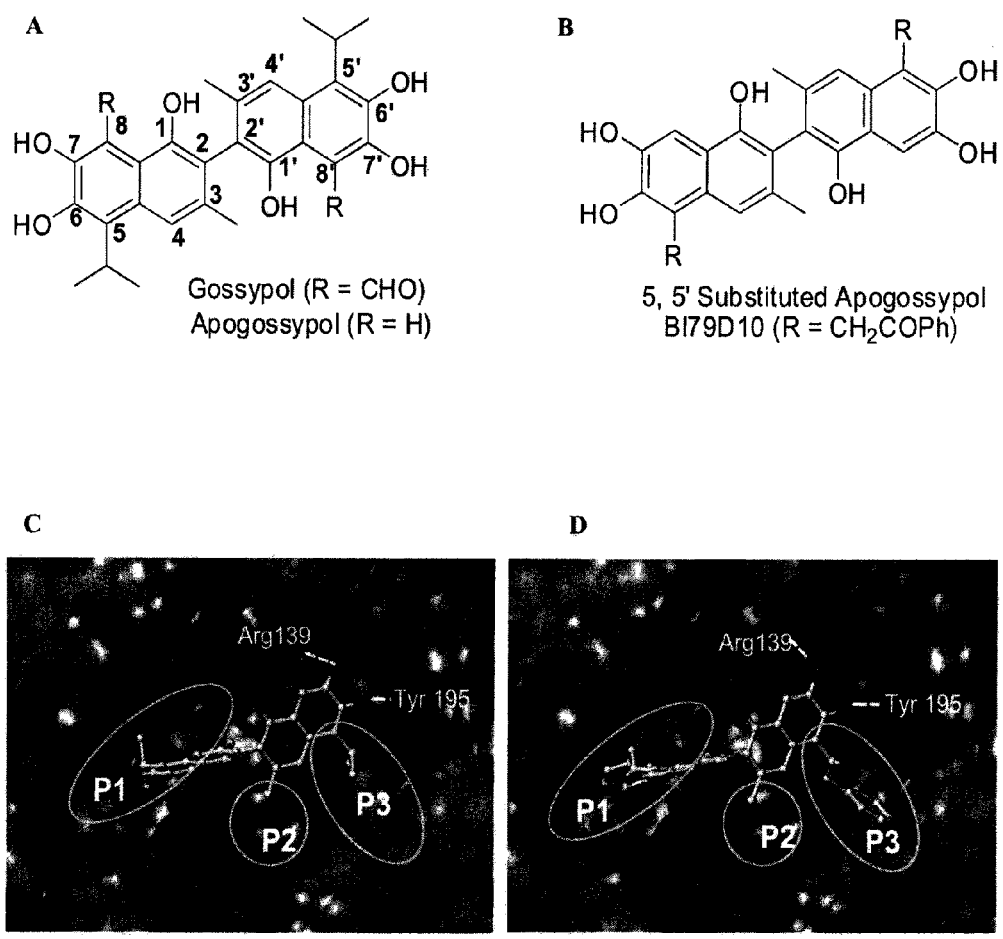
FIG. 1 provides the structures of Gossypol and Apogossypol (A); structure of a compound of the disclosure (B); and molecular docking studies (C) and (D).
Figure 2:
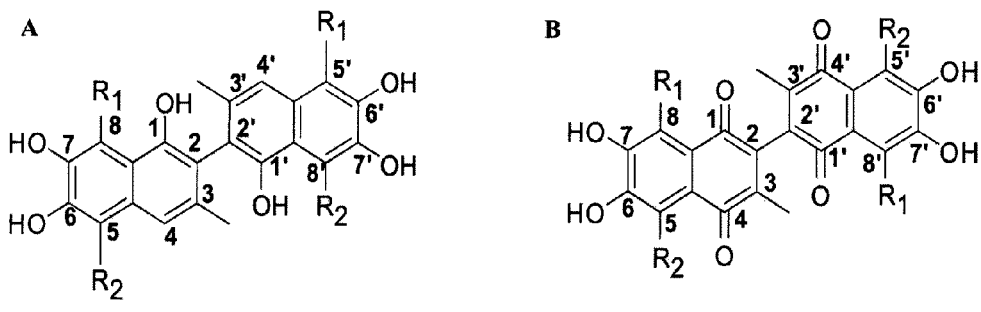
FIG. 2 provides: (A) the structure of Gossypol (1), Apogossypol (2a), BI79D10 (3a) and 8r (4a); (B) the structure of Gossypolone (5), Apogossypolone (6a) and 5,5' substituted 6a derivatives (7, 8a); and the molecular docking studies, including docked structures of (C) compound 6a (Apogossypolone), and (D) compound 6f into Bcl-2 (PDB ID:1YSW).
Figure 2:
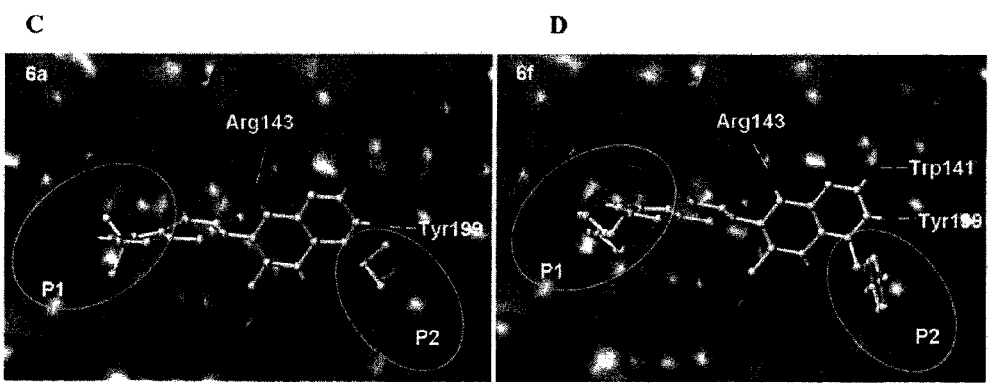
Figure 3:
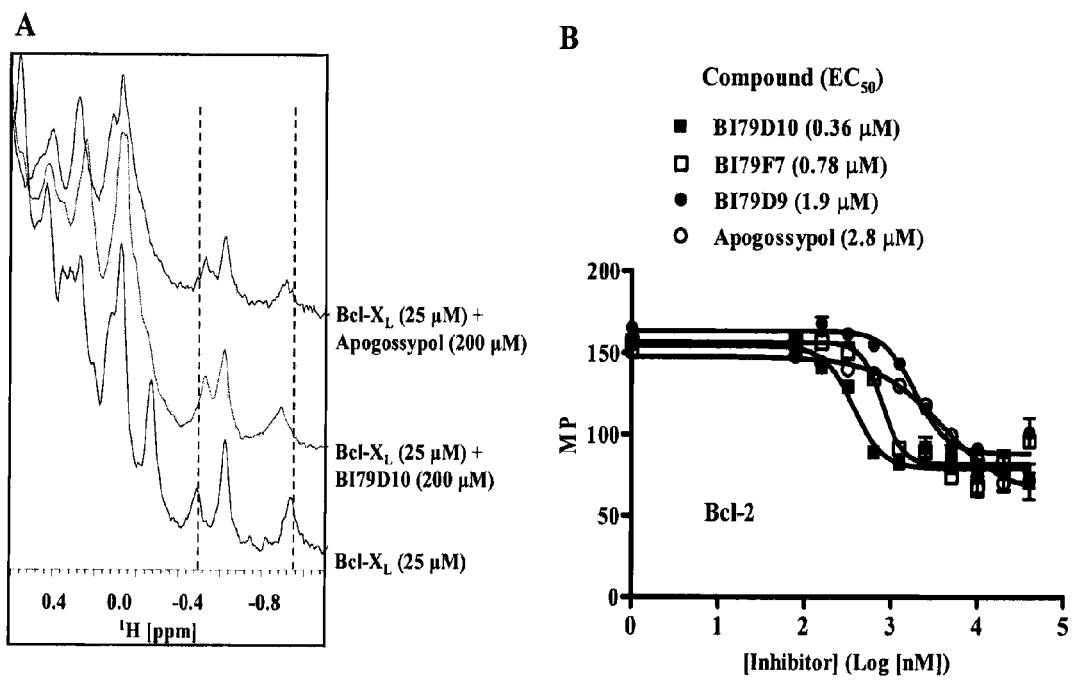
FIG. 3 provides: (A) NMR binding studies of the aliphatic region of the $^1$H-NMR spectrum of Bcl-$X_L$ (25 μM, black), and Bcl-X$_L$ in the presence of Apogossypol and BI79D10; and (B) the EC$_{50}$ values for Apogossypol (2.8 µM) and compounds B179D9 (1.9 µM), B179F7 (0.78 µM), and B179D10 (0.36 µM).
Figure 4:
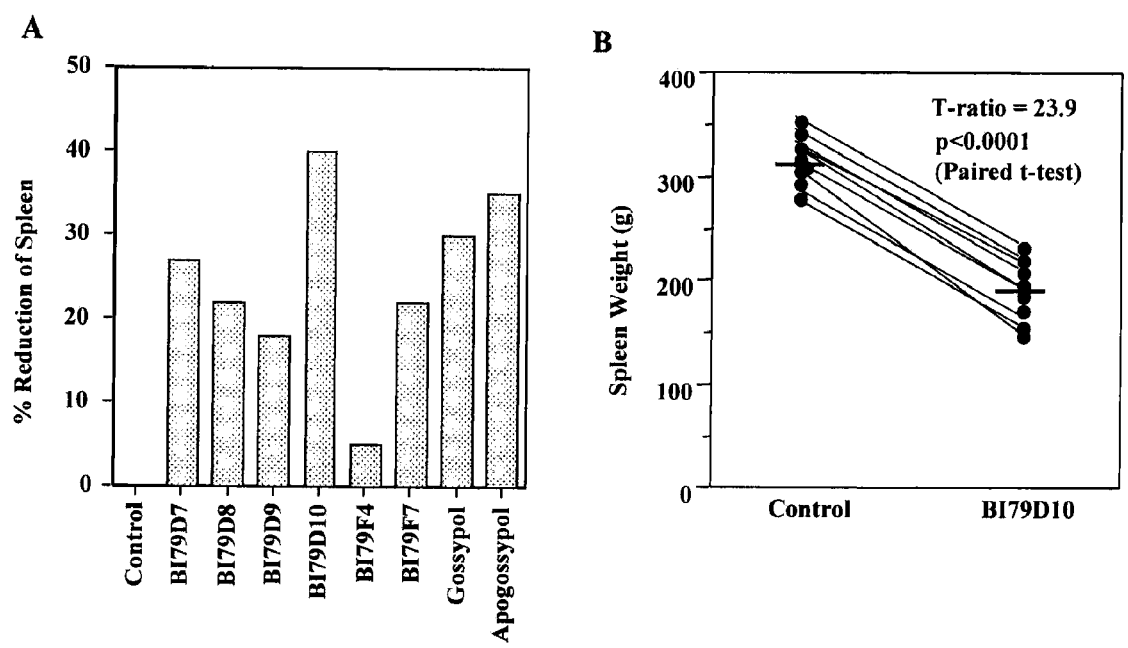
FIGS. 4(A) and 4(B) illustrates the effectiveness of Gossypol, Apogossypol and the compounds of the disclosure on shrinkage of BCL-2 mouse spleen.
Figure 5:
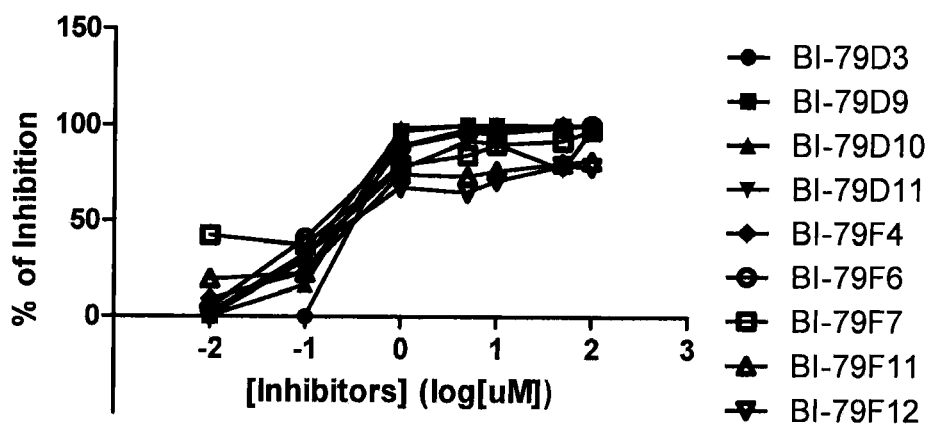
FIG. 5 provides the FP competitive binding curves of compounds of the disclosure using BCL-X$_L$.
Figure 6A:
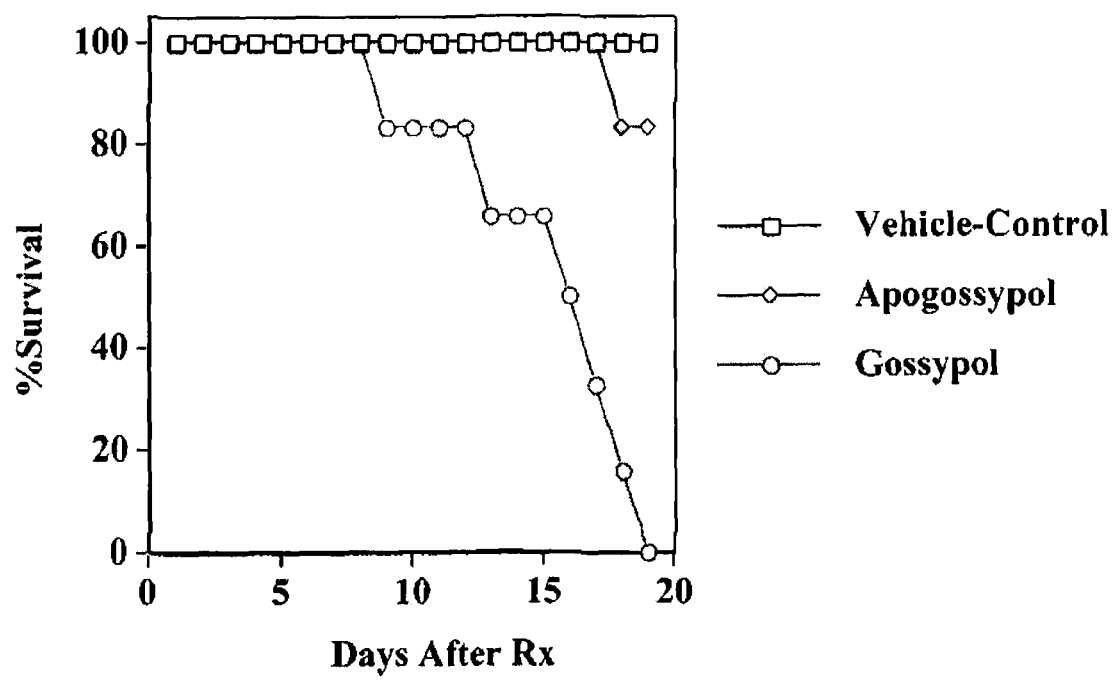
FIGS. 6A and 6B provide the toxicity profiles of Gossypol vs. Apogossypol.
Figure 6B:
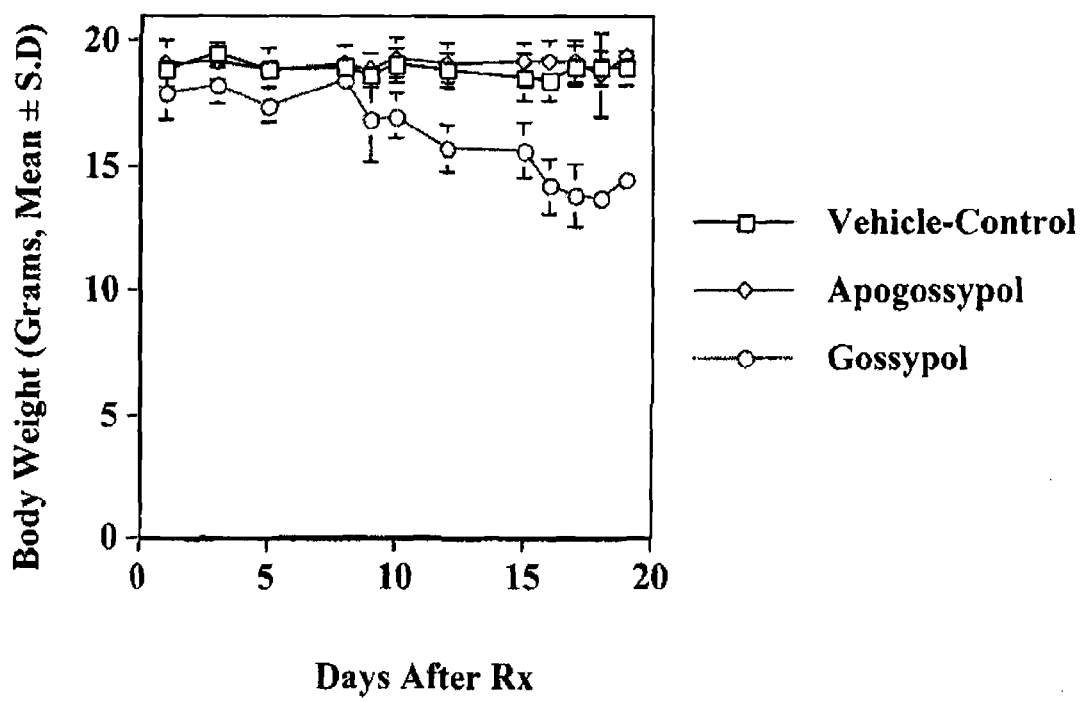
Figure 7A:
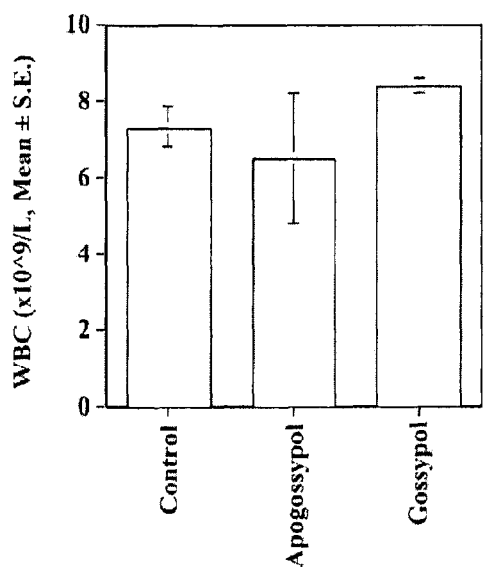
FIGS. 7A, 7B and 7C depict the hematological profiles of mice treated with Apogossypol or Gossypol.
Figure 7A:
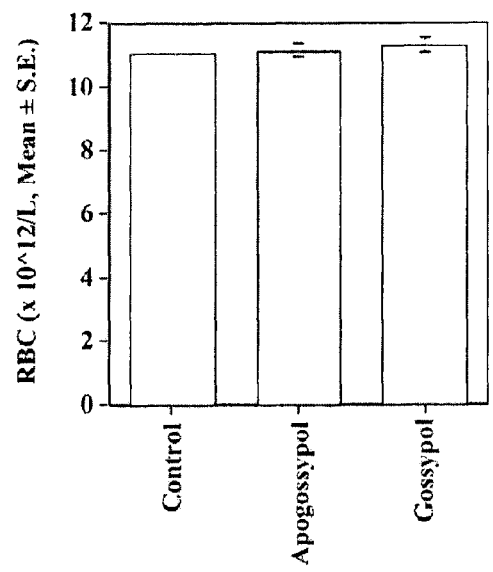
Figure 7B:
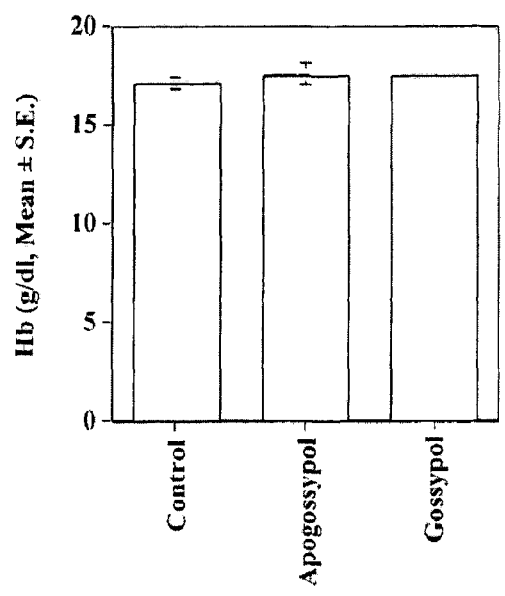
Figure 7B:
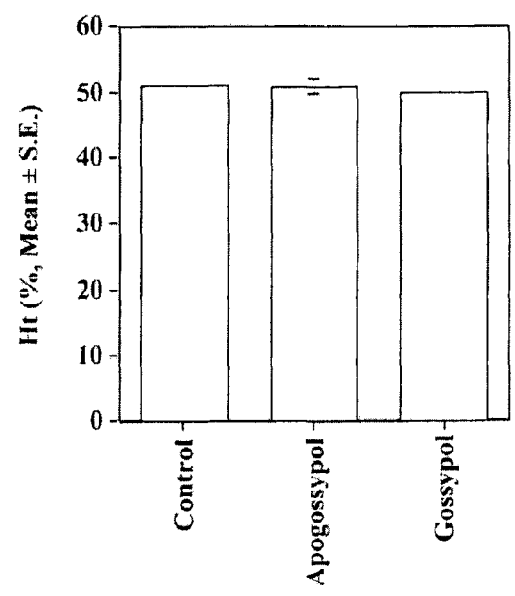
Figure 7C:
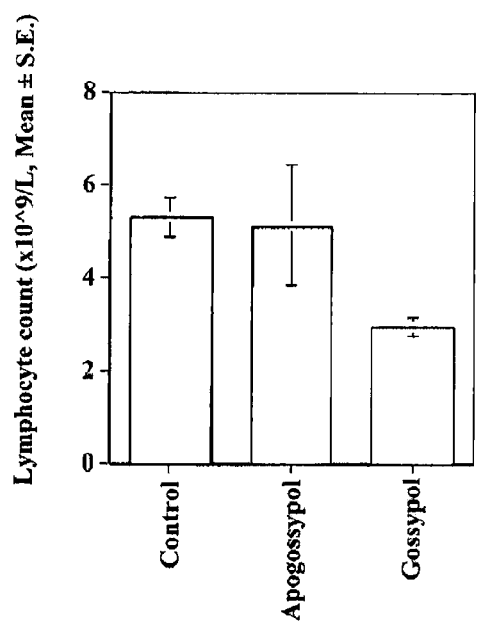
Figure 7C:
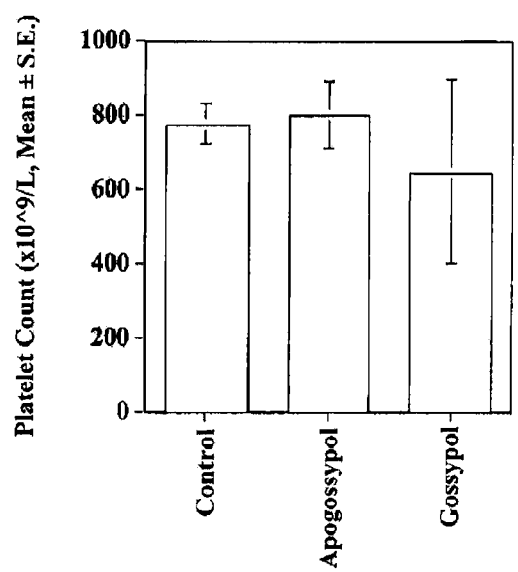
Figure 8:
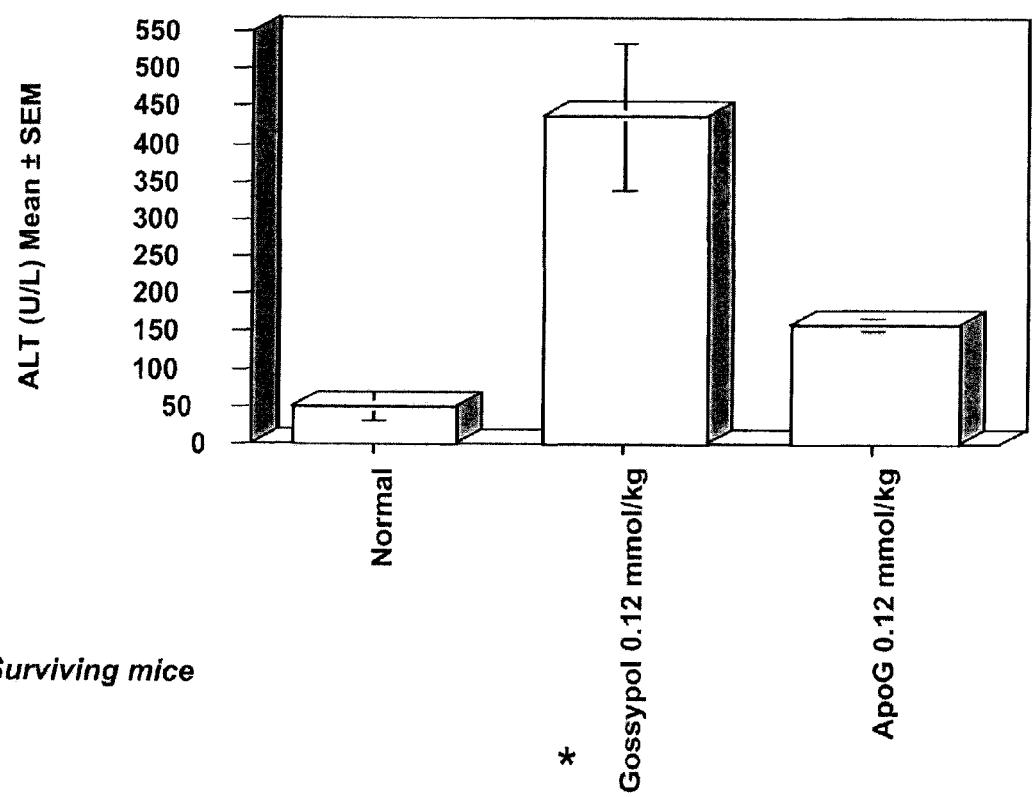
FIG. 8 shows the relative blood chemistry profiles of mice treated with Apogossypol or Gossypol.
Figure 9:
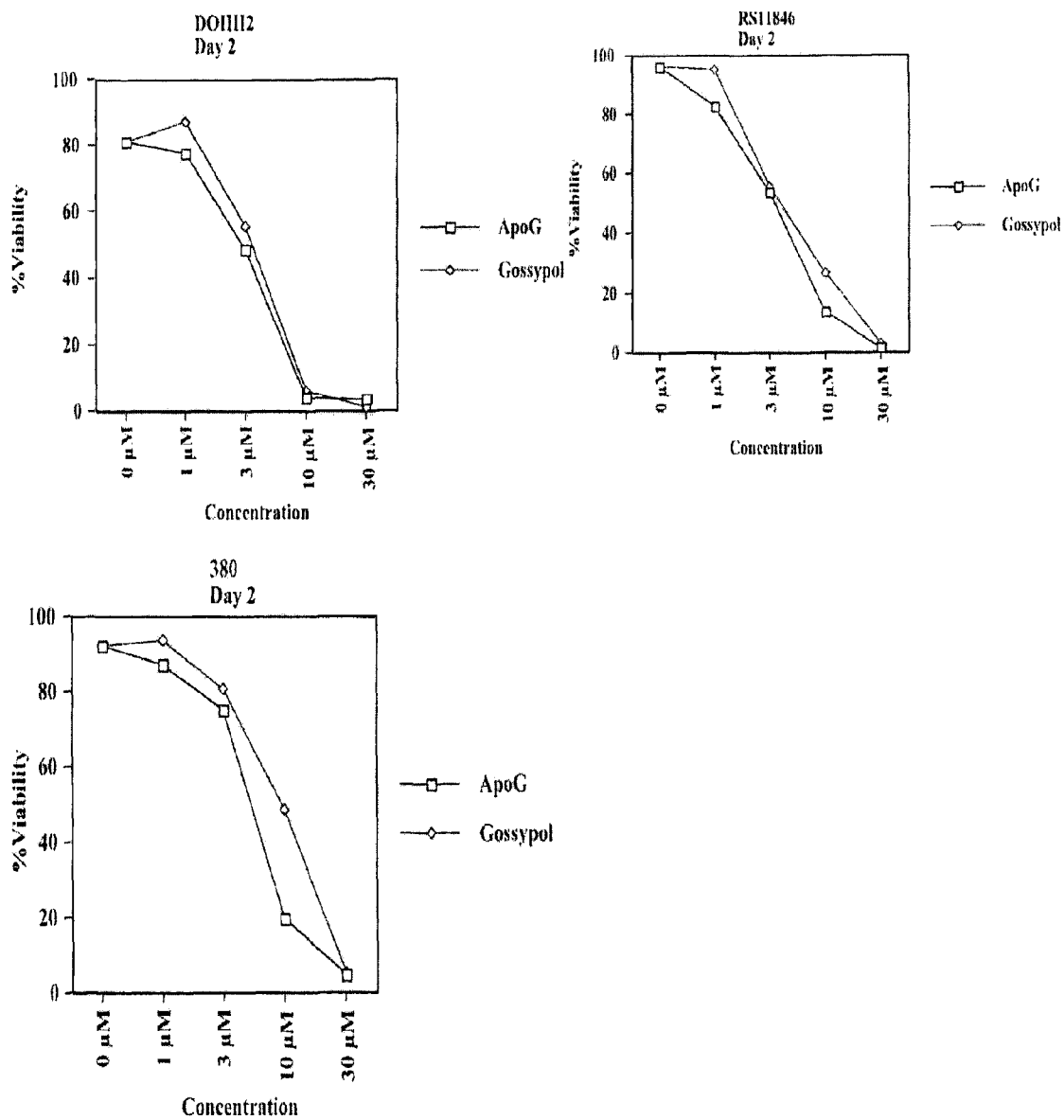
FIG. 9 provides a comparison of apoptosis induction of NHL B-cell lines, including DOHH2, RS11846 and 380, by Apogossypol and Gossypol.
Figure 10:
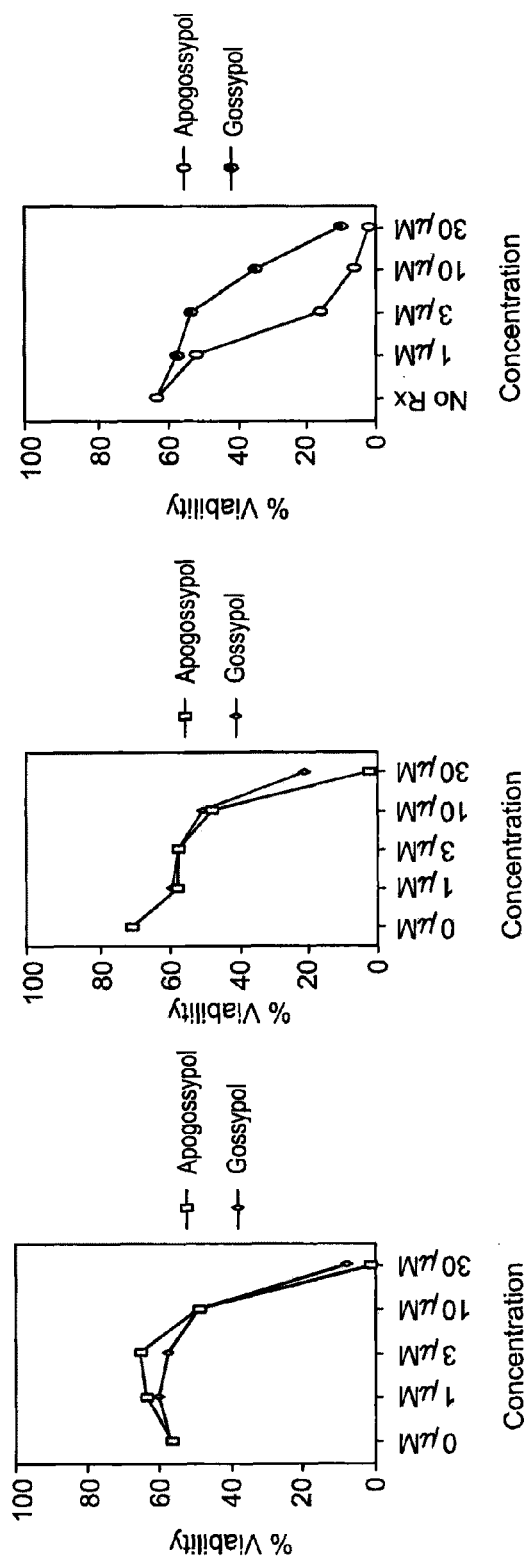
FIG. 10 provides a comparison of activity of Gossypol and Apogossypol against cultured murine B-cells from transgenic mice: BCL-2 vs. BCL-2/TRAF2DN.
Figure 11:
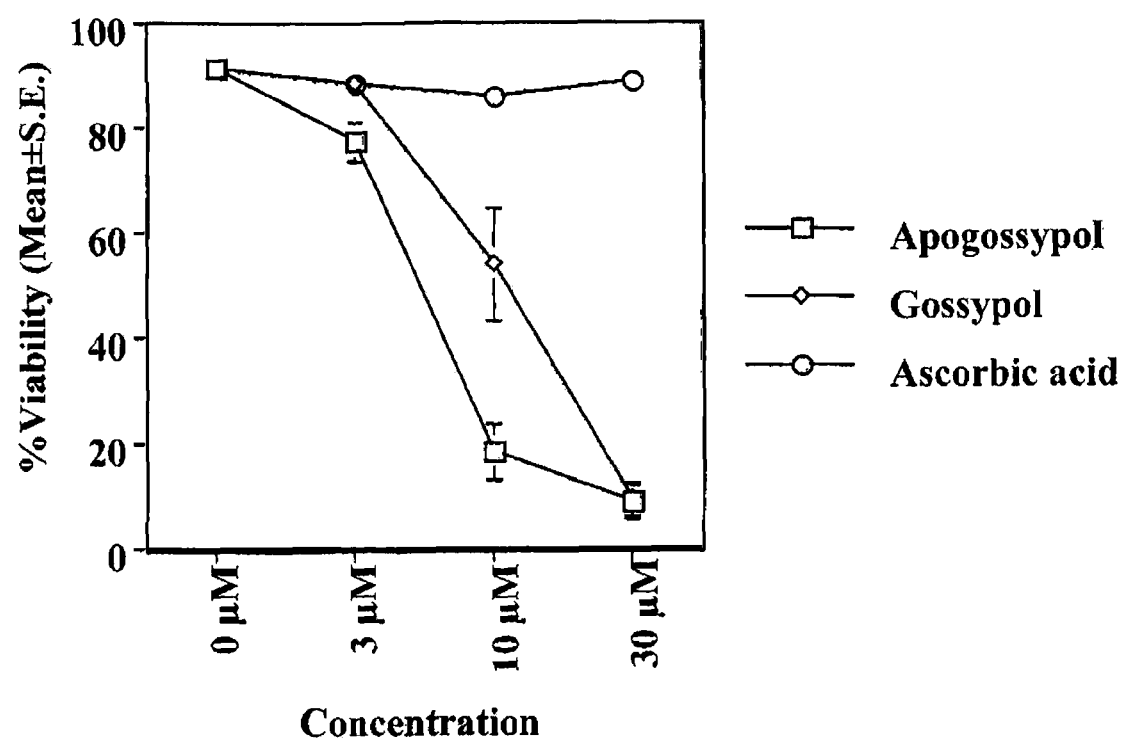
FIG. 11 provides a comparison of Apogossypol and Gossypol induction of apoptosis of cultured CLL B-cells.
Figure 12A:
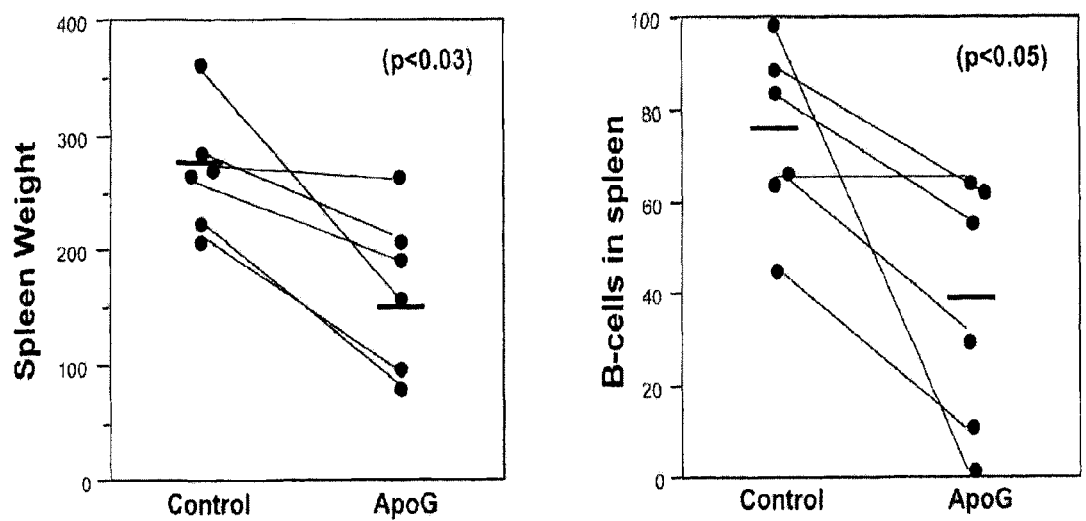
FIGS. 12A and 12B show the Apogossypol activity in BCL-2 transgenic mice.
Figure 12B:
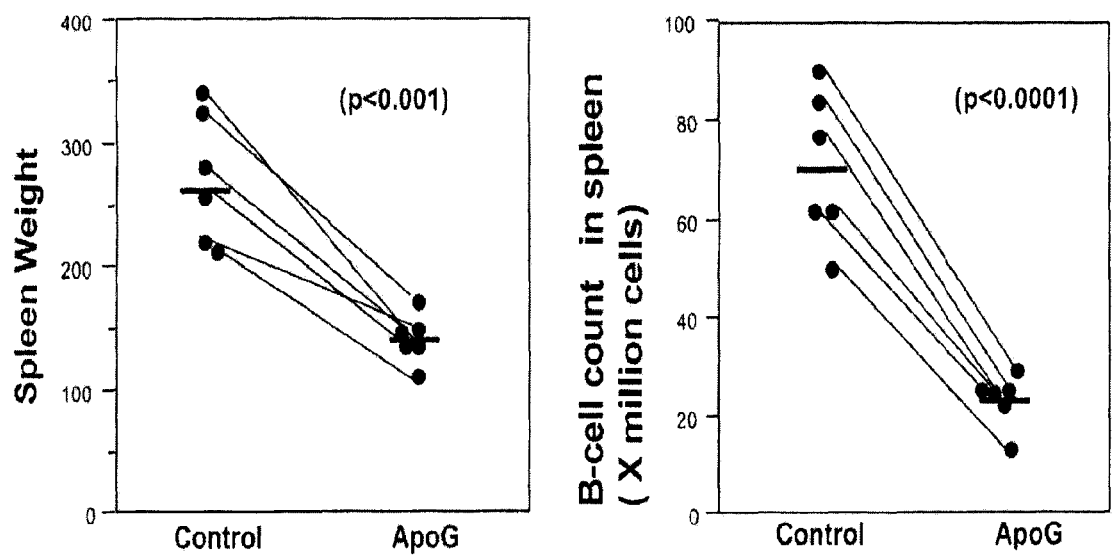
Figure 13:
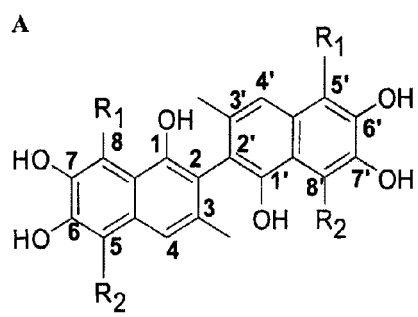
FIG. 13 provides: (A) the structure of Gossypol (1), Apogossypol (2) and BI79D10 (3); (B) structure of 5,5' substituted Apogossypol derivatives; Molecular docking studies and stereo views of docked structures of: (C) compound 2 (Apogossypol) and (D) compound 8r into Bcl-2 (PDB ID:1YSW).
Figure 13:
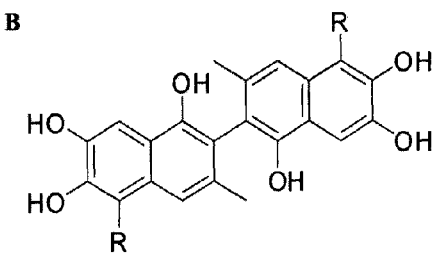
Figure 13:
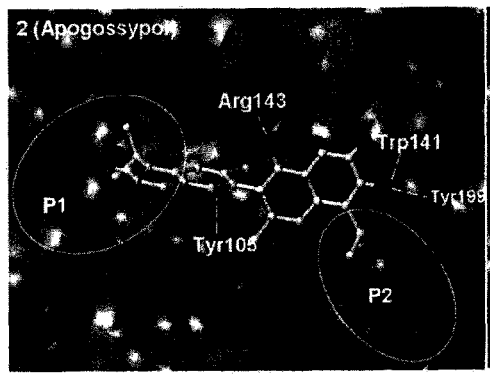
Figure 13:
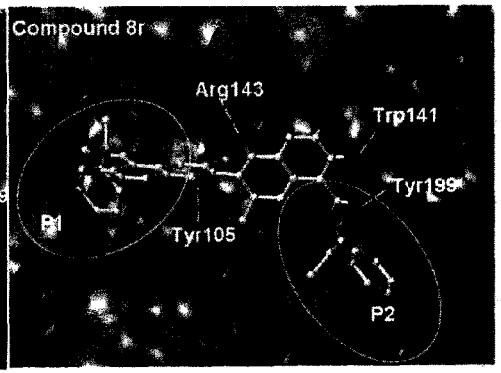
Figure 14:
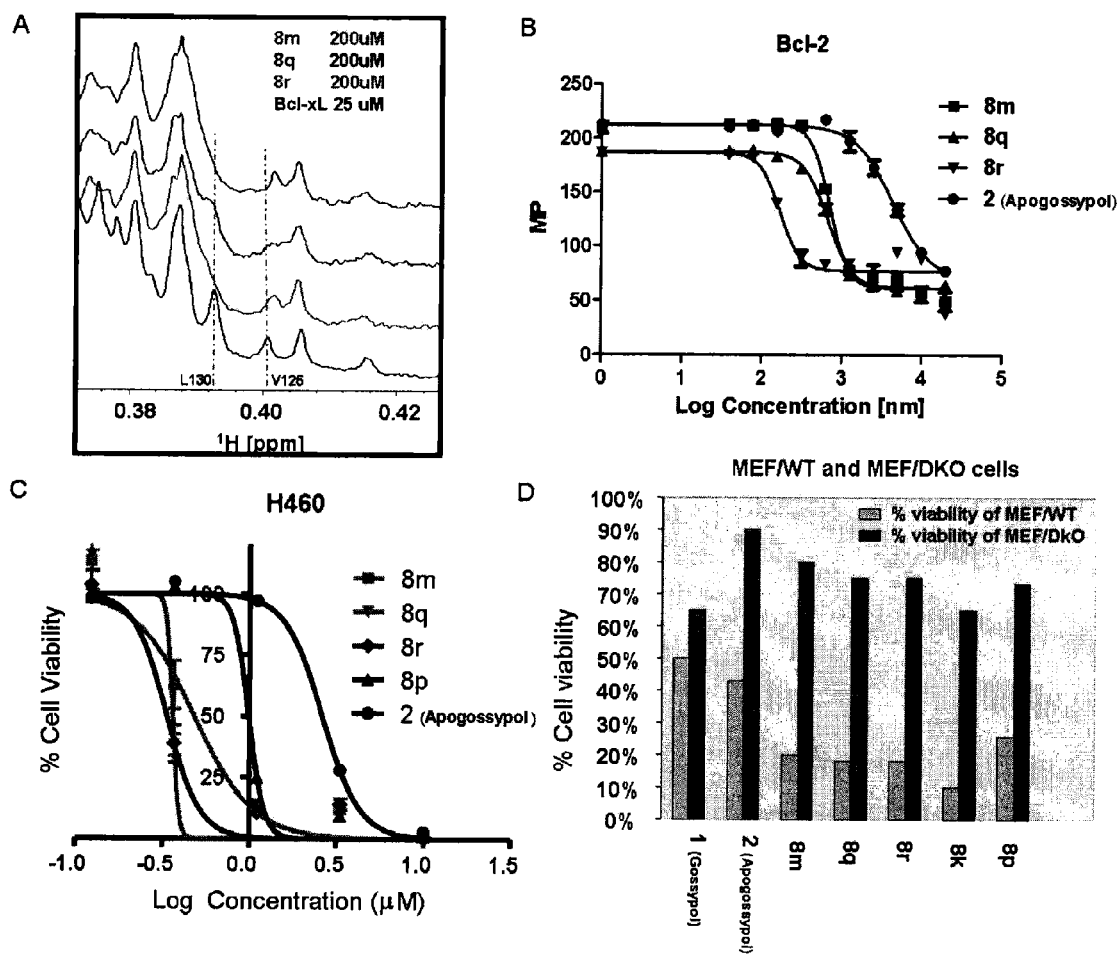
FIG. 14 provides: (A) NMR binding studies. Aliphatic region of the $^1$H-NMR spectrum of Bcl-X$_L$ (25 µM, black) and Bcl-X$_L$ in the presence of compound 8m (200 µM, grey), compound 8q (200 µM, blue), and compound 8r (200 µM, red). (B) Fluorescence polarization-based competitive binding curves of 8m (solid squares), 8q (solid up triangle), 8r (solid down triangle) and 2 (Apogossypol) (solid dots) using Bcl-2. (C) Inhibition of cell growth by compounds 8m (red square), 8q (green triangle), 8r (blue diamond), 8p (dark triangle) and 2 (Apogossypol) (dark dots) in the H460 human lung cell line. Cells were treated for 3 days and cell viability was evaluated using ATP-LITE assay. (D) Mouse embryonic fibroblast cells with wild-type (MEF/WT; blue bars) or bax$^{-/-}$bak$^{-/-}$ double knockout (red bars) genotypes were treated with various 5,5' substituted Apogossypol derivatives at 10 µM and apoptosis was monitored by Annexin V-FITC assays.
Figure 15:
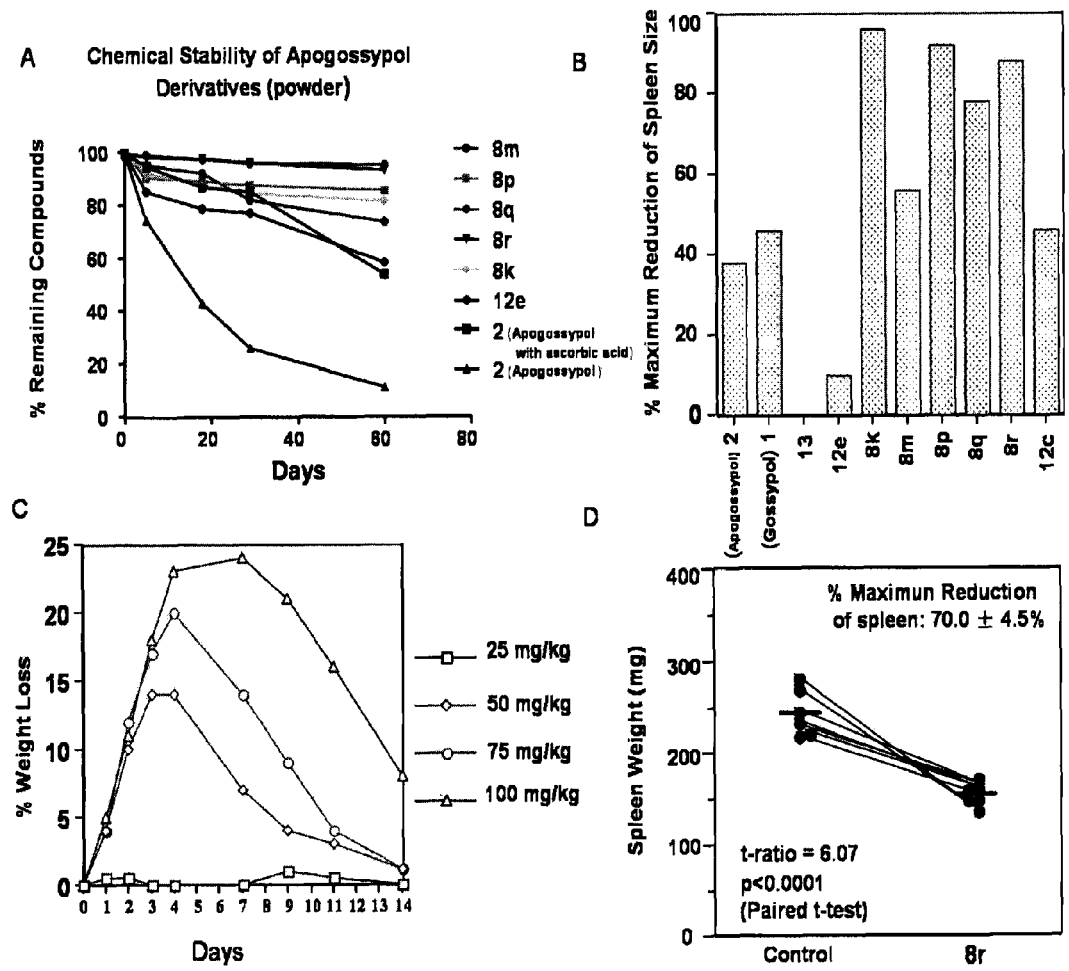
FIG. 15 provides: (A) Fluorescence polarization-based competitive curves of 6f using Bcl-X$_L$ (red square), Bcl-2 (blue dot) and Mcl-1 (green down triangle). (B) Inhibition of cell growth by compounds 1 (dark dot), 6a (blue square), 6i (red down triangle), 8a (purple diamond) and 6f (green up triangle) in the PC-3 human prostate cancer cell line. Cells were treated for 3 days and cell viability was evaluated using ATP-LITE assay. (C) Inhibition of cell growth by compounds 6a (red dot), 6b (green square), 6i (blue up triangle) and 6f (purple down triangle) in the H460 human lung cancer cell line. Cells were treated for 3 days and cell viability was evaluated using ATP-LITE assay. (D) Inhibition of cell growth by compounds 6a (dark square), 6f (red diamond) and 6i (green cycle) in the human primary CLL cells. Cells were treated for 1 days and cell viability was evaluated using Annexin-V apoptosis assay.
Figure 16:
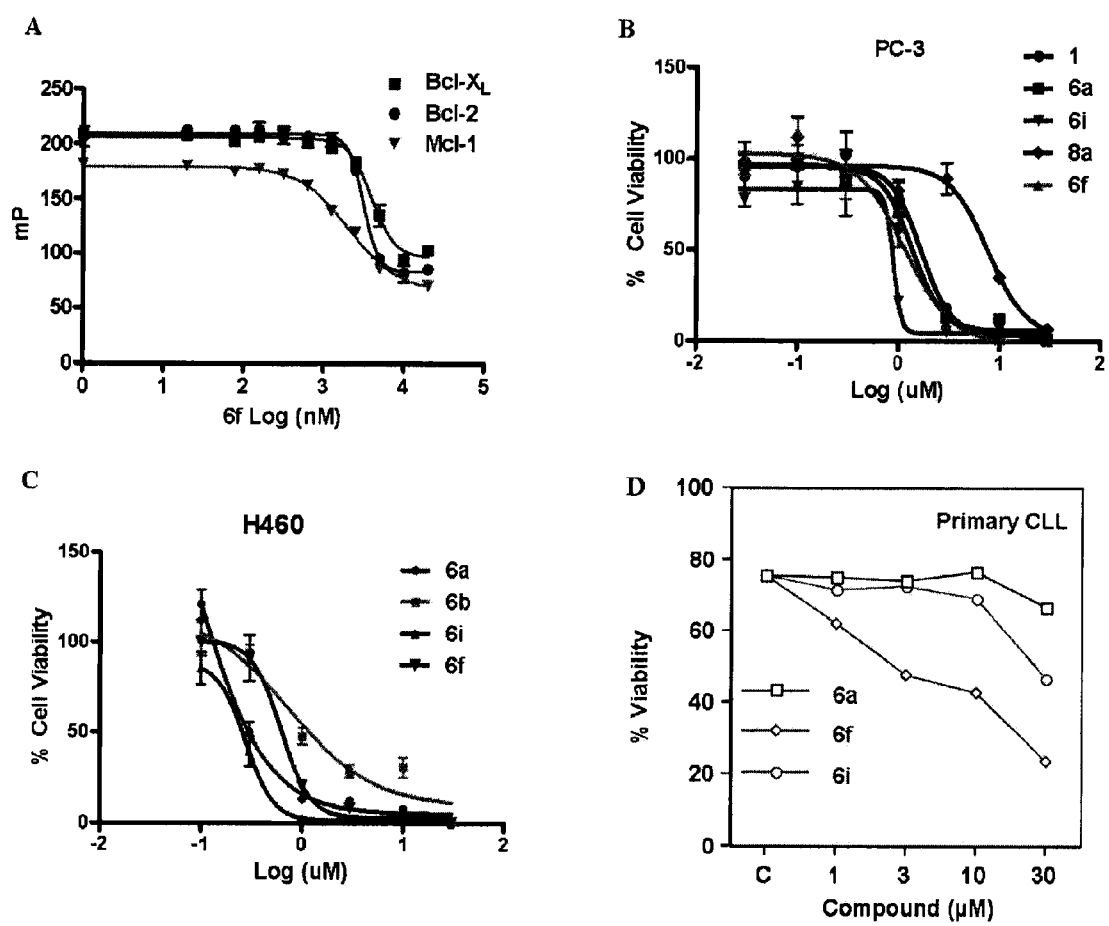
FIG. 16 provides: (A) Chemical stability of Apogossypol derivatives when left at room temperature in powder form: 8m (red dot), 8p (green square), 8q (purple dot), 8r (blue triangle), 8k (pink dot), 12e (dark dot), 2 (Apogossypol with ascorbic acid, dark square) and 2 (Apogossypol, dark triangle). Chemical stability was evaluated in the air for 60 days at room temperature. The stability was monitored using a combination of HPLC and LCMS. (B) Effects of 5,5' substituted Apogossypol derivatives on shrinkage of Bcl-2 mouse spleen at a single intraperitoneal injection dose of 0.072 mmol/kg. All shrinkage data are percentage of maximum reduction of mice spleen size. (C) % Weight loss in mice induced by single ip injection of various amount of compound 8r. (D) Effects of compound 8r at 42 mg/kg (0.06 mmol/kg) on reduction of spleen weight of six Bcl-2 mice treatment with a single intraperitoneal injection. Data shown as means±S.E. (n=6). P<0.0001.
Figure 17:
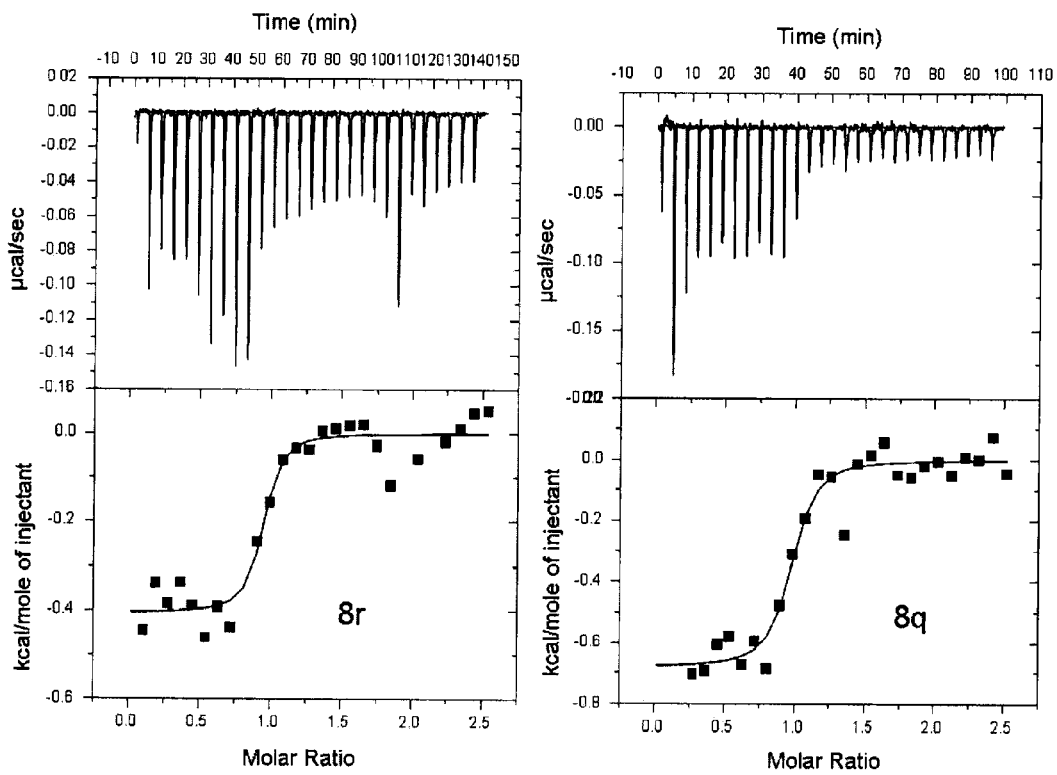
FIG. 17 shows the ITC studies of 5,5' substituted Apogossypol derivatives.
Figure 18:
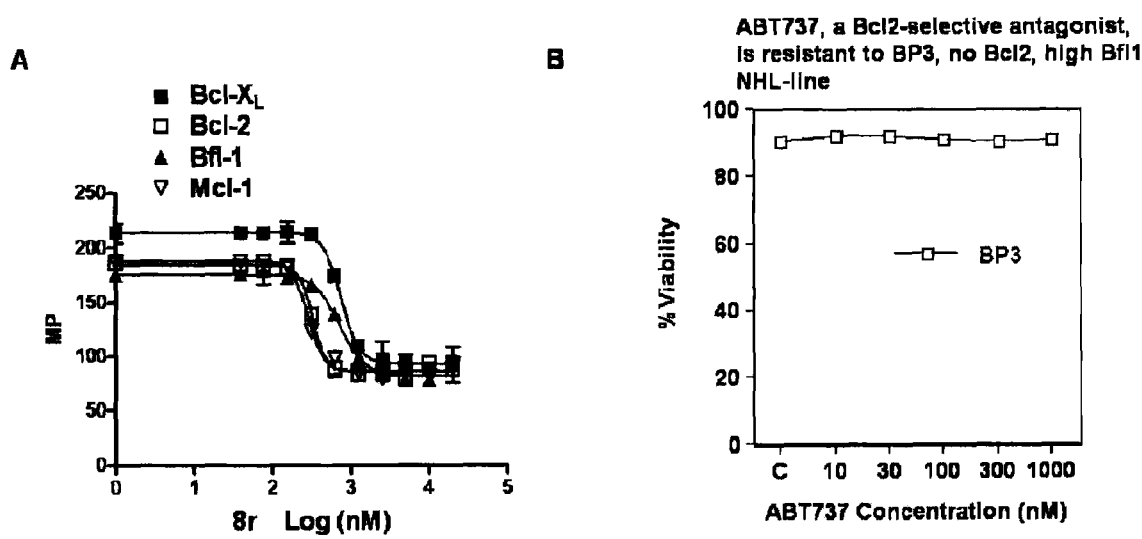
FIG. 18 provides: (A) Compound 8r competes with the binding of Bcl-2 family proteins to FITC-Bim BH3 peptide; (B) Cytotoxicity assays of ABT-737 against BP3 using Annexin V-FITC and propidium iodide assay.
Figure 19:
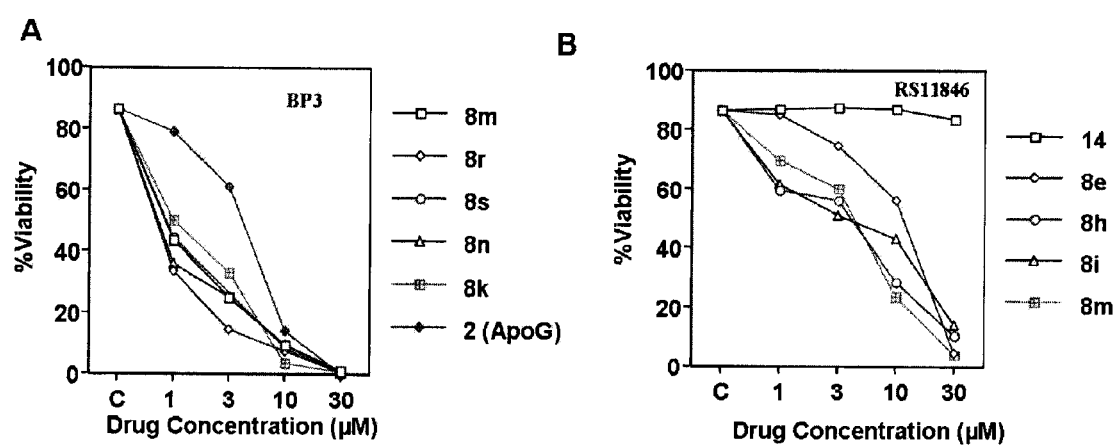
FIG. 19 shows the cytotoxicity assays of 5,5' substituted Apogossypol derivatives against (A) BP3 cell and (B) RS11846 cancer cell lines using Annexin V-FITC and propidium iodide assay.
Figure 20:
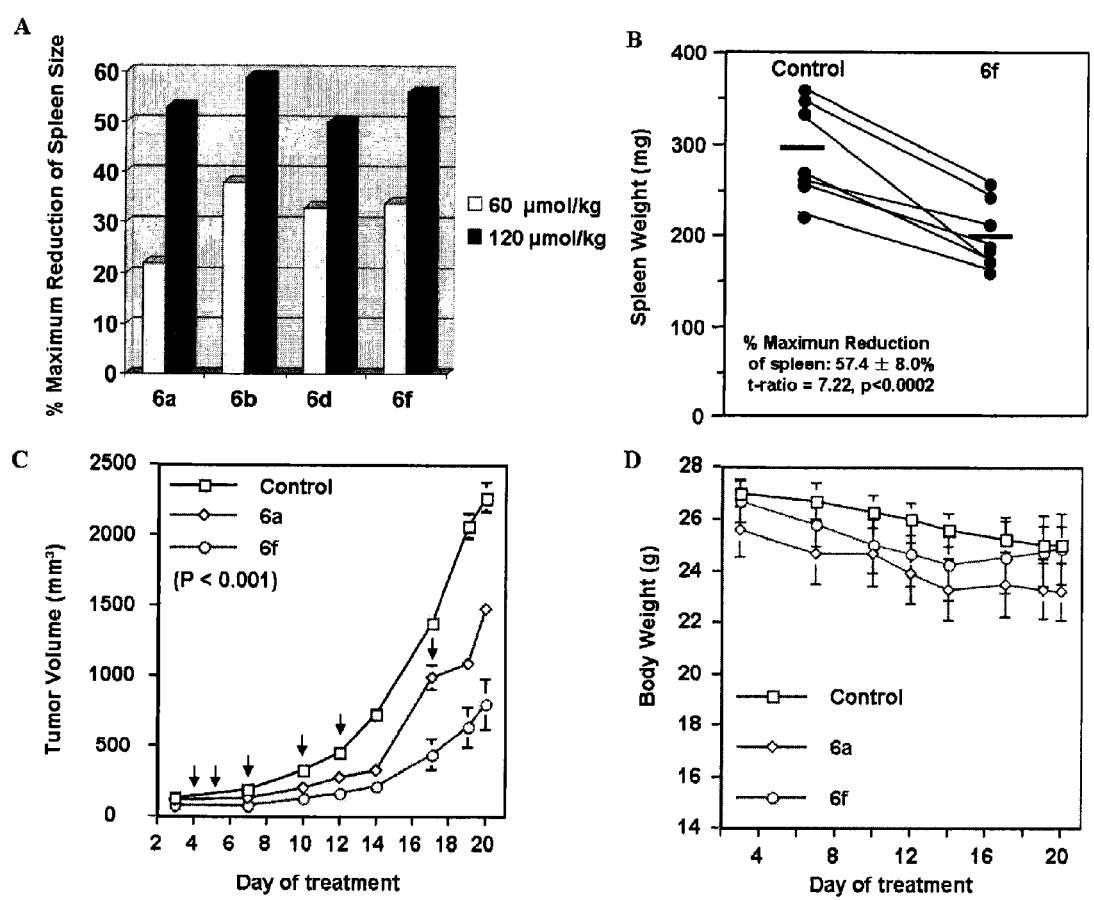
FIG. 20 shows the characterization of compounds in vivo. (A) Effects of 5,5' substituted 6a derivatives on shrinkage of Bcl-2 mouse spleen at a single intraperitoneal injection dose of 60 µmmol/kg and 120 µmmol/kg, respectively. All shrinkage data are percentage of maximum reduction of mice spleen size. (B) Effects of compound 6f at 60 µmmol/kg on reduction of spleen weight of six Bcl-2 mice treatment with a single intraperitoneal injection. Data shown as means±S.E. (n=7). P<0.0002. (C) Effect of i.p. 6f and 6a at 50 mg/kg on the growth of PCC-1 tumors in nude mice. Compound 6f significantly inhibited tumor growth compared to vehicle control determined with Anova statistics (P<0.001). Tumor growth inhibition ratios (T/C %) were calculated by dividing the average tumor volume in the treatment group by the average tumor volume in the control group. Dark down arrow "↓" represents the date mice were treated with compounds (D) Average body weight changes during treatment.

Unless otherwise defined, scientific and technical terms used in connection with the disclosure shall have the meanings that are commonly understood by those of ordinary skill in the art. Further, unless otherwise required by context, singular terms shall include pluralities and plural terms shall include the singular. Generally, nomenclatures utilized in connection with, and techniques of, cell and tissue culture, molecular biology, and protein and oligo- or polynucleotide chemistry and hybridization described herein are those well known and commonly used in the art. Standard techniques are used for recombinant DNA, oligonucleotide synthesis, and tissue culture and transformation (e.g., electroporation, lipofection). Enzymatic reactions and purification techniques are performed according to manufacturer's specifications or as commonly accomplished in the art or as described herein. The nomenclatures utilized in connection with, and the laboratory procedures and techniques of, analytical chemistry, synthetic organic chemistry, and medicinal and pharmaceutical chemistry described herein are those well known and commonly used in the art. Standard techniques are used for chemical syntheses, chemical analyses, pharmaceutical preparation, formulation, and delivery, and treatment of patients.

The following terms, definitions and abbreviations further apply:

The term "patient" refers to organisms to be treated by the methods of the disclosure. Such organisms include, but are not limited to, humans and other mammals. In the context of the disclosure, the term "subject" generally refers to an individual who will receive or who has received treatment described herein (e.g., administration of the compounds of the disclosure, and optionally one or more additional therapeutic agents).

The term "BCL-2 family of proteins" refers to the family of proteins that currently includes at least the following six proteins: BCL-$X_L$, BCL-2, BCL-W, BCL-B, BFL-1, and MCL-1.

Where substituent groups are specified by their conventional chemical formulae, written from left to right, they equally encompass the chemically identical substituents that would result from writing the structure from right to left, e.g., —$CH_2O$— is equivalent to —$OCH_2$—.

The term "alkyl," by itself or as part of another substituent, means, unless otherwise stated, a straight (i.e. unbranched) or branched chain, or cyclic hydrocarbon radical, or combination thereof, which may be fully saturated, mono- or polyunsaturated and can include di- and multivalent radicals, having the number of carbon atoms designated (i.e. $C_1$-$C_{10}$ means one to ten carbons). Examples of saturated hydrocarbon radicals include, but are not limited to, groups such as methyl, ethyl, n-propyl, isopropyl, n-butyl, t-butyl, isobutyl, sec-butyl, cyclohexyl, (cyclohexyl)methyl, cyclopropylmethyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. Alkyl groups which are limited to hydrocarbon groups are termed "homoalkyl."

Specific values listed herein for groups, substituents, and ranges, are for illustration only; they do not exclude other defined values or other values within defined ranges for the groups and substituents. For example, "alkyl" may be methyl, ethyl, propyl, isopropyl, butyl isobutyl, sec-butyl, pentyl, 3-pentyl, or hexyl; cycloalkyl may be cyclopropyl, cyclobutyl, cyclopentyl, or cyclohexyl; "—O($C_1$-$C_6$)alkyl (alkoxy)" may be methoxy, ethoxy, propoxy, isopropoxy, butoxy, isobutoxy, sec-butoxy, pentoxy, 3-pentoxy, or hexyloxy.

The term "alkylene" by itself or as part of another substituent means a divalent radical derived from an alkyl, as exemplified, but not limited, by —$CH_2CH_2CH_2CH_2$—, —$CH_2CH$=$CHCH_2$—, —$CH_2C$.ident.$CCH_2$—, —$CH_2CH_2CH(CH_2CH_2CH_3)CH_2$—. Typically, an alkyl (or alkylene) group will have from 1 to 24 carbon atoms, with those groups having 10 or fewer carbon atoms being in the disclosure. A "lower alkyl" or "lower alkylene" is a shorter chain alkyl or alkylene group, generally having eight or fewer carbon atoms.

The terms "alkyl, alkoxy, alkenyl, alkynyl," etc. denote both straight and branched groups; but reference to an individual group such as "propyl" embraces only the straight chain group, a branched chain isomer such as "isopropyl" being specifically referred to.

The term "heteroalkyl," by itself or in combination with another term, means, unless otherwise stated, a stable straight or branched chain, or cyclic hydrocarbon radical, or combinations thereof, consisting of at least one carbon atoms and at least one heteroatom selected from the group consisting of O, N, P, Si and 5, and wherein the nitrogen, phosphorus, and sulfur atoms may optionally be oxidized and the nitrogen heteroatom may optionally be quaternized. The heteroatom(s) O, N, P and S and Si may be placed at any interior position of the heteroalkyl group or at the position at which alkyl group is attached to the remainder of the molecule. Examples include, but are not limited to, —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$, —S(O)—$CH_3$, —$CH_2$—$CH_2$—S(O)$_2$—$CH_3$, —CH=CH—O—$CH_3$, —Si($CH_3$)$_3$, —$CH_2$—CH=N—$OCH_3$, —CH=CH—N($CH_3$)—$CH_3$, O—$CH_3$, —O—$CH_2$—$CH_3$, and —CN. Up to two or three heteroatoms may be consecutive, such as, for example, —$CH_2$—NH—$OCH_3$ and —$CH_2$—O—Si($CH_3$)$_3$. Similarly, the term "heteroalkylene" by itself or as part of another substituent means a divalent radical derived from heteroalkyl, as exemplified, but not limited by, —$CH_2$—$CH_2$—S—$CH_2$—$CH_2$— and —$CH_2$—S—$CH_2$—$CH_2$—NH—$CH_2$—. For heteroalkylene groups, heteroatoms can also occupy either or both of the chain termini (e.g., alkyleneoxo, alkylenedioxo, alkyleneamino, alkylenediamino, and the like). Still further, for alkylene and heteroalkylene linking groups, no orientation of the linking group is implied by the direction in which the formula of the linking group is written. For example, the formula —C(O)OR'— res both —C(O)OR'— and —R'OC(O)—. As described above, heteroalkyl groups, as used herein, include those groups that are attached to the remainder of the molecule through a heteroatom, such as —C(O)R', —C(O)NR', —NR'R', —OR', —SR', and/or —$SO_2$R'. Where "heteroalkyl" is recited, followed by recitations of specific heteroalkyl groups, such as —NR'R" or the like, it will be understood that the terms heteroalkyl and —NR'R" are not redundant or mutually exclusive. Rather, the specific heteroalkyl groups are recited to add clarity. Thus, the term "heteroalkyl" should not be interpreted herein as excluding specific heteroalkyl groups, such as —NR'R" or the like.

The terms "cycloalkyl" and "heterocycloalkyl", by themselves or in combination with other terms, re, unless otherwise stated, cyclic versions of "alkyl" and "heteroalkyl", respectively. Additionally, for heterocycloalkyl, a heteroatom can occupy the position at which the heterocycle is attached to the remainder of the molecule. Examples of cycloalkyl include, but are not limited to, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like. The terms "cycloalkylene" and "heterocycloalkylene" refer to the divalent derivatives of cycloalkyl and heterocycloalkyl, respectively.

More specifically, the term "alkyl" refers to a branched or unbranched saturated hydrocarbon group of 1 to 6 carbon atoms, such as methyl, ethyl, n-propyl, isopropyl, n-butyl, isobutyl, t-butyl, pentyl, and the like. Alkyl groups disclosed herein contain 1 to 6 carbon atoms, such as, for example, methyl, ethyl, and the like. As used herein the term "alkyl"

also includes the term "cycloalkyl," which refers to a cyclic alkyl group of three to eight, or three, five or six, carbon atoms. The term "cycloalkylene" as used herein refers to a divalent cyclic alkylene group, typically a 3-, 5-, 6-, or 8-membered ring.

The term "alkoxy" as used herein refers to an alkyl group bound through a single, terminal ether linkage, i.e., an "alkoxy" group may be defined as —OR, where R is alkyl as defined herein. A "lower alkoxy" group refers to an alkoxy group containing 1 to 6, carbon atoms.

The term "aryl" means, unless otherwise stated, a polyunsaturated, aromatic, hydrocarbon substituent which may be a single ring or multiple rings (from 1 to 3 rings) which are fused together or linked covalently. The term "heteroaryl" refers to aryl groups (or rings) that contain from one to four heteroatoms (in each separate ring in the case of multiple rings) selected from N, O, and S, wherein the nitrogen and sulfur atoms are optionally oxidized, and the nitrogen atom(s) are optionally quaternized. A heteroaryl group may be attached to the remainder of the molecule through a carbon or heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of above noted aryl and heteroaryl ring systems are selected from the group of acceptable substituents described below. The terms "arylene" and "heteroarylene" refer to the divalent radicals of aryl and heteroaryl, respectively.

For brevity, the term "aryl" when used in combination with other terms (e.g., aryloxo, arylthioxo, arylalkyl) includes both aryl and heteroaryl rings as defined above. Thus, the term "arylalkyl" is meant to include those radicals in which an aryl group is attached to an alkyl group (e.g., benzyl, phenethyl, pyridylmethyl and the like) including those alkyl groups in which a carbon atom (e.g., a methylene group) has been replaced by, for example, an oxygen atom (e.g., phenoxymethyl, 2-pyridyloxymethyl, 3-(1-naphthyloxy)propyl, and the like).

The term "aryl" as used herein refers to an aromatic carbocyclic ring, typically 6- or 10-membered, wherein at least one ring is aromatic. For example, "aryl" denotes a phenyl group or an ortho-fused bicyclic carbocyclic group having about nine to ten ring atoms in which at least one ring is aromatic.

"Heteroaryl" encompasses a group attached via a ring carbon of a monocyclic aromatic ring containing five or six ring atoms consisting of carbon and one to four heteroatoms each independently may be non-peroxide oxygen, sulfur, and N(X), where X is absent or is H, O, ($C_1$-$C_4$)alkyl, phenyl or benzyl, as well as a group of an ortho-fused bicyclic-heterocycle of about eight to ten ring atoms derived therefrom, particularly a benz-derivative or one derived by fusing a propylene, trimethylene, or tetramethylene digroup thereto.

Where a heteroalkyl, heterocycloalkyl, or heteroaryl includes a specific number of members (e.g. "3 to 7 membered"), the term "member" referrers to a carbon or heteroatom.

The terms "halo" or "halogen," by themselves or as part of another substituent, mean, unless otherwise stated, a fluorine, chlorine, bromine, or iodine atom. Additionally, terms such as "haloalkyl," are meant to include monohaloalkyl and polyhaloalkyl. For example, the term "halo($C_1$-$C_4$)alkyl" is mean to include, but not be limited to, trifluoromethyl, 2,2,2-trifluoroethyl, 4-chlorobutyl, 3-bromopropyl, and the like. The term "halo" also refers to fluoro, chloro, bromo, or iodo.

The term "oxo" as used herein means an oxygen that is double bonded to a carbon atom.

Each of above terms (e.g., "alkyl," "heteroalkyl," "cycloalkyl, and "heterocycloalkyl", "aryl," "heteroaryl" as well as their divalent radical derivatives) are meant to include both substituted and unsubstituted forms of the indicated radical. Substituents for each type of radical are provided below.

Substituents for alkyl, heteroalkyl, cycloalkyl, heterocycloalkyl monovalent and divalent derivative radicals (including those groups often referred to as alkylene, alkenyl, heteroalkylene, heteroalkenyl, alkynyl, cycloalkyl, heterocycloalkyl, cycloalkenyl, and heterocycloalkenyl) may be one or more of a variety of groups selected from, but not limited to: —OR', =O, =NR', =N—OR', —NR'R", —SR', -halogen, —SiR'R"R'", —OC(O)R', —C(O)R', —CO$_2$R', —C(O)NR'R", —OC(O)NR'R", —NR"C(O)R', —NR'—C(O)NR"R'", —NR"C(O)OR', —NR—C(NR'R")=NR''', —S(O)R', —S(O)$_2$R', —S(O)$_2$NR'R", —NRSO$_2$R', —CN and —NO$_2$ in a number ranging from zero to (2 m'+1), where m' is the total number of carbon atoms in such radical. R', R", R'" and R"" each independently refer to hydrogen, substituted or unsubstituted heteroalkyl, substituted or unsubstituted cycloalkyl, substituted or unsubstituted heterocycloalkyl, substituted or unsubstituted aryl (e.g., aryl substituted with 1-3 halogens), substituted or unsubstituted alkyl, alkoxy or thioalkoxy groups, or arylalkyl groups. When a compound of the disclosure includes more than one R group, for example, each of the R groups is independently selected as are each R', R", R'" and R"" groups when more than one of these groups is. When R' and R'" are attached to the same nitrogen atom, they may be combined with the nitrogen atom to form a 4-, 5-, 6-, or 7-membered ring. For example, —NR'R" is meant to include, but not be limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —CF$_3$ and —CH$_2$CF$_3$) and acyl (e.g., —C(O)CH—, —C(O)CF$_3$, —C(O)CH$_2$OCH$_3$, and the like).

Similar to the substituents described for alkyl radicals above, exemplary substituents for aryl and heteroaryl groups (as well as their divalent derivatives) are varied and are selected from, for example: halogen, —OR', —NR'R", —SR', -halogen, —SiR'R"R'", —OC(O)R', —C(O)R', —CO$_2$R', —C(O)NR'R", —OC(O)NR'R", —NR"C(O)R', —NR'—C(O)NR"R'", —NR"C(O)OR', —NR—C(NR'R"R''')=NR'''', —NR—C(NR'R")=NR''', —S(O)R', —S(O)$_2$R', —S(O)$_2$NR'R", —NRSO$_2$R', —CN and —NO$_2$, —R', —N$_3$, —CH(Ph)$_2$, fluoro($C_1$-$C_4$)alkoxo, and fluoro($C_1$-$C_4$)alkyl, in a number ranging from zero to the total number of open valences on aromatic ring system; and where R', R", R'" and R'" are each independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl and substituted or unsubstituted heteroaryl. When a compound of the disclosure includes more than one R' group, for example, each of the R groups is independently selected as are each R', R", R'" and R"" groups when more than one of these groups is.

Two of the substituents on adjacent atoms of aryl or heteroaryl ring may optionally form a ring of the formula -T-C (O)—(CRR')$_q$—U—, wherein T and U are independently —NR—, —O—, —CRR'— or a single bond, and q is an integer of from 0 to 3. Alternatively, two of the substituents on adjacent atoms of aryl or heteroaryl ring may optionally be replaced with a substituent of the formula -A-(CH$_2$)$_r$—B—, wherein A and B are independently —CRR'—, —O—, —NR—, —S(O)—, —S(O)$_2$—, —S(O)$_2$NR'— or a single bond, and r is an integer of from 1 to 4. One of the single bonds of the new ring so formed may optionally be replaced with a double bond. Alternatively, two of the substituents on adjacent atoms of aryl or heteroaryl ring may optionally be replaced with a substituent of the formula —(CRR')$_s$—X'—(C"R''')$_d$—, where s and d are independently integers of from 0 to 3, and X' is —O—, —NR'—, —S(O)—, —S(O)$_2$—, or —S(O)$_2$NR'—. The substituents R, R', R" and R''' are each independently selected from hydrogen, substituted or unsubstituted alkyl, substituted or unsubstituted cycloalkyl, substituted or unsubstituted heterocycloalkyl, substituted or unsubstituted aryl, and substituted or unsubstituted heteroaryl.

As used herein, the term "heteroatom" or "ring heteroatom" is meant to include oxygen (O), nitrogen (N), sulfur (S), phosphorus (P), and silicon (Si).

An "aminoalkyl" as used herein refers to an amino group covalently bound to an alkylene linker. The amino group is —NR'R", wherein R' and R" are typically selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

A "substituent group," as used herein, means a group selected from the following moieties:

(A) —OH, —NH$_2$, —SH, —CN, —CF$_3$, NO$_2$, oxo, halogen, unsubstituted alkyl, unsubstituted heteroalkyl, unsubstituted cycloalkyl, unsubstituted heterocycloalkyl, unsubstituted aryl, unsubstituted heteroaryl, and (B) alkyl, heteroalkyl, cycloalkyl, heterocycloalkyl, aryl, and heteroaryl, substituted with at least one substituent selected from:

(i) oxo, —OH, —NH$_2$, —SH, —CN, —CF$_3$, —NO$_2$, halogen, unsubstituted alkyl, unsubstituted heteroalkyl, unsubstituted cycloalkyl, unsubstituted heterocycloalkyl, unsubstituted aryl, unsubstituted heteroaryl, and (ii) alkyl, heteroalkyl, cycloalkyl, heterocycloalkyl, aryl, and heteroaryl, substituted with at least one substituent selected from:

(a) oxo, —OH, —NH$_2$, —SH, —CN, —CF$_3$, —NO$_2$, halogen, unsubstituted alkyl, unsubstituted heteroalkyl, unsubstituted cycloalkyl, unsubstituted heterocycloalkyl, unsubstituted aryl, unsubstituted heteroaryl, and (b) alkyl, heteroalkyl, cycloalkyl, heterocycloalkyl, aryl, or heteroaryl, substituted with at least one substituent selected from oxo, —OH, —NH$_2$, —SH, —CN, —CF$_3$, —NO$_2$, halogen, unsubstituted alkyl, unsubstituted heteroalkyl, unsubstituted cycloalkyl, unsubstituted heterocycloalkyl, unsubstituted aryl, and unsubstituted heteroaryl.

A "size-limited substituent" or "size-limited substituent group," as used herein means a group selected from all of the substituents described above for a "substituent group," wherein each substituted or unsubstituted alkyl is a substituted or unsubstituted $C_1$-$C_{20}$ alkyl, each substituted or unsubstituted heteroalkyl is a substituted or unsubstituted 2 to 20 membered heteroalkyl, each substituted or unsubstituted cycloalkyl is a substituted or unsubstituted $C_4$-$C_8$ cycloalkyl, and each substituted or unsubstituted heterocycloalkyl is a substituted or unsubstituted 4 to 8 membered heterocycloalkyl.

A "lower substituent" or "lower substituent group," as used herein means a group selected from all of the substituents described above for a "substituent group," wherein each substituted or unsubstituted alkyl is a substituted or unsubstituted $C_1$-$C_8$ alkyl, each substituted or unsubstituted heteroalkyl is a substituted or unsubstituted 2 to 8 membered heteroalkyl, each substituted or unsubstituted cycloalkyl is a substituted or unsubstituted $C_5$-$C_7$ cycloalkyl, and each substituted or unsubstituted heterocycloalkyl is a substituted or unsubstituted 5 to 7 membered heterocycloalkyl.

The compounds of the disclosure may exist as salts. The disclosure includes such salts. Examples of applicable salt forms include hydrochlorides, hydrobromides, sulfates, methanesulfonates, nitrates, maleates, acetates, citrates, fumarates, tartrates (eg (+)-tartrates, (−)-tartrates or mixtures thereof including racemic mixtures, succinates, benzoates and salts with amino acids such as glutamic acid. These salts may be prepared by methods known to those skilled in art. Also included are base addition salts such as sodium, potassium, calcium, ammonium, organic amino, or magnesium salt, or a similar salt. When compounds of the disclosure contain relatively basic functionalities, acid addition salts may be obtained by contacting the neutral form of such compounds with a sufficient amount of the desired acid, either neat or in a suitable inert solvent. Examples of acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like. Certain specific compounds of the disclosure contain both basic and acidic functionalities that allow the compounds to be converted into either base or acid addition salts.

The neutral forms of the compounds may be regenerated by contacting the salt with a base or acid and isolating the parent compound in the conventional manner. The parent form of the compound differs from the various salt forms in certain physical properties, such as solubility in polar solvents.

Certain compounds of the disclosure can exist in unsolvated forms as well as solvated forms, including hydrated forms. In general, the solvated forms are equivalent to unsolvated forms and are encompassed within the scope of the disclosure. Certain compounds of the disclosure may exist in multiple crystalline or amorphous forms. In general, all physical forms are equivalent for the uses contemplated by the disclosure and are intended to be within the scope of the disclosure.

Certain compounds of the disclosure possess asymmetric carbon atoms (optical or chiral centers) or double bonds; the enantiomers, racemates, diastereomers, tautomers, geometric isomers, stereoisometric forms that may be defined, in terms of absolute stereochemistry, as (R)- or (S)- or, as (D)- or (L)- for amino acids, and individual isomers are encompassed within the scope of the disclosure. The compounds of the disclosure do not include those which are known in art to be too unstable to synthesize and/or isolate. The disclosure is meant to include compounds in racemic and optically pure forms. Optically active (R)- and (S)-, or (D)- and (L)-isomers may be prepared using chiral synthons or chiral reagents, or resolved using conventional techniques. When the compounds described herein contain olefinic bonds or other centers of geometric asymmetry, and unless specified otherwise, it is intended that the compounds include both E and Z geometric isomers.

The term "tautomer," as used herein, refers to one of two or more structural isomers which exist in equilibrium and which are readily converted from one isomeric form to another.

It will be apparent to one skilled in the art that certain compounds of this disclosure may exist in tautomeric forms, all such tautomeric forms of the compounds being within the scope of the disclosure.

Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the compounds are within the scope of the disclosure.

Unless otherwise stated, structures depicted herein are also meant to include compounds which differ only in the presence of one or more isotopically enriched atoms. For example, compounds having the structures except for the replacement of a hydrogen by a deuterium or tritium, or the replacement of a carbon by $^{13}$C- or $^{14}$C-enriched carbon are within the scope of this disclosure.

The compounds of the disclosure may also contain unnatural proportions of atomic isotopes at one or more of atoms that constitute such compounds. For example, the compounds may be radiolabeled with radioactive isotopes, such as for example tritium (3H), iodine-125 ($^{125}$I) or carbon-14 ($^{14}$C). All isotopic variations of the compounds of the disclosure, whether radioactive or not, are encompassed within the scope of the disclosure.

The term "pharmaceutically acceptable salts" is meant to include salts of active compounds which are prepared with relatively nontoxic acids or bases, depending on the particular substituent moieties found on the compounds described herein. When compounds of the disclosure contain relatively acidic functionalities, base addition salts may be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the disclosure contain relatively basic functionalities, acid addition salts may be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge et al., "Pharmaceutical Salts", Journal of Pharmaceutical Science, 1977, 66, 1-19). Certain specific compounds of the disclosure contain both basic and acidic functionalities that allow the compounds to be converted into either base or acid addition salts.

In addition to salt forms, the disclosure provides compounds, which are in a prodrug form. Prodrugs of the compounds described herein are those compounds that readily undergo chemical changes under physiological conditions to provide the compounds of the disclosure. Additionally, prodrugs may be converted to the compounds of the disclosure by chemical or biochemical methods in an ex vivo environment. For example, prodrugs may be slowly converted to the compounds of the disclosure when placed in a transdermal patch reservoir with a suitable enzyme or chemical reagent.

The terms "a," "an," or "a(n)", when used in reference to a group of substituents herein, mean at least one. For example, where a compound is substituted with "an" alkyl or aryl, the compound is optionally substituted with at least one alkyl and/or at least one aryl. Moreover, where a moiety is substituted with an R substituent, the group may be referred to as "R-substituted." Where a moiety is R-substituted, the moiety is substituted with at least one R substituent and each R substituent is optionally different.

Description of compounds of the disclosure are limited by principles of chemical bonding known to those skilled in the art. Accordingly, where a group may be substituted by one or more of a number of substituents, such substitutions are selected so as to comply with principles of chemical bonding and to give compounds which are not inherently unstable and/or would be known to one of ordinary skill in the art as likely to be unstable under ambient conditions, such as aqueous, neutral, and several known physiological conditions. For example, a heterocycloalkyl or heteroaryl is attached to the remainder of the molecule via a ring heteroatom in compliance with principles of chemical bonding known to those skilled in the art thereby avoiding inherently unstable compounds.

The terms "treating" or "treatment" in reference to a particular disease includes prevention of the disease.

The term "prodrug" or "pro-drug" refers to an agent that is converted into the parent drug in vivo. Prodrugs are often useful because, in some situations, they may be easier to administer than the parent drug. They may, for instance, be bioavailable by oral administration whereas the parent is not. The prodrug may also have improved solubility in pharmaceutical compositions over the parent drug, or may demonstrate increased palatability or be easier to formulate.

As used herein, the term "Apogossypol" is a broad term which includes, without limitation, L-Apogossypol, D-Apogossypol, racemic Apogossypol, S-Apogossypol, R-Apogossypol, (−)Apogossypol and (+)Apogossypol, and includes (−)Apogossypol that is substantially free of (+)Apogossypol.

Throughout the disclosure, when a particular compound is mentioned by name, for example, Apogossypol or Apogossypolone, it is understood that the scope of the disclosure encompasses pharmaceutically acceptable salts, esters, amides, metabolites, or prodrugs of the named compound.

It will be appreciated by those skilled in the art that compounds of the disclosure having a chiral center may exist in and be isolated in optically active and racemic forms. Some compounds may exhibit polymorphism. It is to be understood that the disclosure encompasses any racemic, optically active, polymorphic, or stereoisomeric form, or mixtures thereof, of a compound of the disclosure, which possesses the useful properties described herein. Also, if the named compound comprises a chiral center, the scope of the disclosure also includes compositions comprising the racemic mixture of the two enantiomers, as well as compositions comprising each enantiomer individually, substantially free of the other enantiomer. Thus, for example, contemplated herein is a composition comprising the S enantiomer substantially free of the R enantiomer, or a composition comprising the R enantiomer substantially free of the S enantiomer.

By "substantially free" it is meant that the composition comprises less than 10%, or less than 8%, or less than 5%, or less than 3%, or less than 1% of the minor enantiomer. If the named compound comprises more than one chiral center, the scope of the disclosure also includes compositions comprising a mixture of the various diastereomers, as well as compositions comprising each diastereomer substantially free of the other diastereomers. Thus, for example, commercially available Apogossypol is a racemic mixture comprising two separate enantiomers. The recitation of "Apogossypol" throughout this disclosure includes compositions that comprise the racemic mixture of Apogossypol, compositions that comprise the (+) enantiomer substantially free of the (−) enantiomer, and compositions that comprise the (−) enantiomer substantially free of the (+) enantiomer.

It is well known in the art how to prepare optically active forms (for example, by resolution of the racemic form by recrystallization techniques, by synthesis from optically active starting materials, by chiral synthesis, or by chromatographic separation using a chiral stationary phase) and how to determine the anti cancer activity using the standard tests described herein, or using other similar tests which are well known in the art.

The term "pharmaceutical composition" refers to a mixture of a compound with other chemical components, such as diluents or carriers. The pharmaceutical composition facilitates administration of the compound to an organism. Multiple techniques of administering a compound exist in the art including, but not limited to, oral, injection, aerosol, parenteral, and topical administration. Pharmaceutical compositions can also be obtained by reacting compounds with inorganic or organic acids such as hydrochloric acid, hydrobromic acid, sulfuric acid, nitric acid, phosphoric acid, methanesulfonic acid, ethanesulfonic acid, p-toluenesulfonic acid, salicylic acid and the like.

The term "pharmaceutically acceptable salt" refers to a formulation of a compound that does not cause significant irritation to an organism to which it is administered and does not abrogate the biological activity and properties of the compound. Pharmaceutical salts may be obtained by reacting a compound of the disclosure with inorganic acids such as hydrochloric acid, hydrobromic acid, sulfuric acid, nitric acid, phosphoric acid, methanesulfonic acid, ethanesulfonic acid, p-toluenesulfonic acid, salicylic acid and the like. Pharmaceutical salts can also be obtained by reacting a compound of the disclosure with a base to form a salt such as an ammonium salt, an alkali metal salt, such as a sodium or a potassium salt, an alkaline earth metal salt, such as a calcium or a magnesium salt, a salt of organic bases such as dicyclohexylamine, N-methyl-D-glucamine, tris(hydroxymethyl)methylamine, and salts thereof with amino acids such as arginine, lysine, and the like.

"Inflammation" as used herein is a general term for the local accumulation of fluid, plasma proteins, and white blood cells that is initiated by physical injury, infection, or a local immune response. Many different forms of inflammation are associated with different diseases.

"Inflammation-associated" diseases include, for example, lupus, psoriasis, rheumatoid arthritis, and inflammatory bowel disease. Other inflammation-associated diseases are discussed herein.

As used herein, the terms "anti-inflammatory agent" refers to any anti-inflammatory compounds that are used in the treatment of inflammation.

"Treatment," as used herein, pertains to the therapeutic administration of the compounds of the disclosure for the prevention, amelioration, or cure of disease.

The term "pharmaceutical agent or drug" as used herein refers to a chemical compound or composition capable of inducing a desired therapeutic effect when properly administered to a patient.

As used herein, "substantially pure" means an object species is the predominant species (i.e., on a molar basis it is more abundant than any other individual species in the composition), and a substantially purified fraction is a composition wherein the object species comprises at least about 50 percent (on a molar basis) of all macromolecular species. Generally, a substantially pure composition will comprise more than about 80 percent of all macromolecular species in the composition, for example, more than about 85%, 90%, 95%, and 99%. The object species may be also purified to essential homogeneity (contaminant species cannot be detected in the composition by conventional detection methods), wherein the composition consists essentially of a single species.

Accordingly, in one aspect the disclosure provides compounds of Formula I:

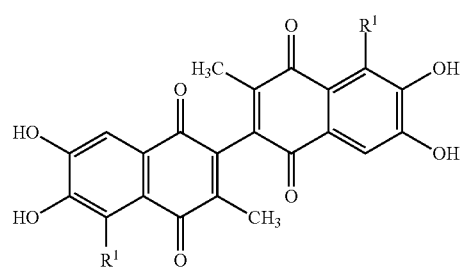

or a pharmaceutically acceptable salt, hydrate, or solvate thereof, wherein:

$R^1$ is independently hydrogen, halogen, amino, nitro, cyano, hydroxyl, substituted or unsubstituted alkyl, substituted or unsubstituted cycloalkyl, perfluoroalkyl, substituted or unsubstituted alkenyl, substituted or unsubstituted alkynyl, substituted or unsubstituted alkoxy, substituted or unsubstituted heteroalkyl, substituted or unsubstituted heterocyclic, substituted or unsubstituted aryl, substituted or unsubstituted arylalkyl, substituted or unsubstituted heteroaryl, substituted or unsubstituted heteroarylalkyl, $-(CH_2)_jOR^2$, $-(CH_2)_jC(O)R^2$, $-(CH_2)_jC(O)OR^2$, $-(CH_2)_jOC(O)R^2$, $-(CH_2)_jNR^3R^4$, $-(CH_2)_jC(O)NR^3R^4$, $-(CH_2)_jOC(O)NR^3R^4$, $-(CH_2)_jNR^5C(O)R^2$, $-(CH_2)_jNR^5C(O)OR^2$, $-(CH_2)_jNR^5C(O)NR^3R^4$, $-(CH_2)_jS(O)_mR^6$, or $-(CH_2)_jNR^5S(O)_mR^6$, wherein j is an integer from 0 to 12; and m is an integer from 0 to 2;

$R^2$ is independently hydrogen, substituted or unsubstituted alkyl, substituted or unsubstituted cycloalkyl, perfluoroalkyl, substituted or unsubstituted alkenyl, substituted or unsubstituted alkynyl, substituted or unsubstituted heteroalkyl, substituted or unsubstituted heterocyclic, substituted or unsubstituted aryl, substituted or unsubstituted arylalkyl, substituted or unsubstituted heteroaryl, substituted or unsubstituted heteroarylalkyl;

$R^3$ and $R^4$ are each independently hydrogen, substituted or unsubstituted alkyl, substituted or unsubstituted cycloalkyl, perfluoroalkyl, substituted or unsubstituted alkenyl, substituted or unsubstituted alkynyl, substituted or unsubstituted heteroalkyl, substituted or unsubstituted heterocyclic, substituted or unsubstituted aryl, substituted or unsubstituted arylalkyl, substituted or unsubstituted heteroaryl, substituted or unsubstituted heteroarylalkyl, or $R^3$ and $R^4$, together with the N atom to which they are attached, form substituted or unsubstituted heterocyclic, or substituted or unsubstituted heteroaryl;

$R^5$ is independently hydrogen, substituted or unsubstituted alkyl, substituted or unsubstituted cycloalkyl, perfluoroalkyl, substituted or unsubstituted alkenyl, substituted or unsubstituted alkynyl, substituted or unsubstituted heteroalkyl, substituted or unsubstituted heterocyclic, substituted or unsubstituted aryl, substituted or unsubstituted arylalkyl, substituted or unsubstituted heteroaryl, substituted or unsubstituted heteroarylalkyl;

$R^6$ is independently hydrogen, substituted or unsubstituted alkyl, substituted or unsubstituted cycloalkyl, perfluoroalkyl, substituted or unsubstituted alkenyl, substituted or unsubstituted alkynyl, substituted or unsubstituted heteroalkyl, substituted or unsubstituted heterocyclic, substituted or unsubstituted aryl, substituted or unsubstituted arylalkyl, substituted or unsubstituted heteroaryl, substituted or unsubstituted heteroarylalkyl;

R, $R^1$, $R^2$, $R^3$, $R^4$, $R^5$, and $R^6$ may be optionally independently substituted with 1 to 3 groups selected from hydrogen, halogen, amino, nitro, cyano, hydroxyl, alkyl, cycloalkyl, perfluoroalkyl, alkenyl, alkynyl, alkoxy, heteroalkyl, heterocyclic, aryl, arylalkyl, heteroaryl, heteroarylalkyl, $-(CH_2)_jOR^7$, $-(CH_2)_jC(O)R^7$, $-(CH_2)_jC(O)OR^7$, $-(CH_2)_jOC(O)R^7$, $-(CH_2)_jNR^8R^9$, $-(CH_2)_jC(O)NR^8R^9$, $-(CH_2)_jOC(O)NR^8R^9$, $-(CH_2)_jNR^{10}C(O)R^7$, $-(CH_2)_jNR^{10}C(O)OR^7$, $-(CH_2)_jNR^{10}C(O)NR^8R^9$, $-(CH_2)_jS(O)_mR^{11}$, or $-(CH_2)_jNR^{10}S(O)_mR^{11}$, wherein j is an integer from 0 to 12; and m is an integer from 0 to 2;

$R^7$ is independently hydrogen, alkyl, cycloalkyl, perfluoroalkyl, alkenyl, alkynyl, heteroalkyl, heterocyclic, aryl, arylalkyl, heteroaryl, or heteroarylalkyl;

$R^8$ and $R^9$ are each independently hydrogen, alkyl, cycloalkyl, perfluoroalkyl, alkenyl, alkynyl, heteroalkyl, heterocyclic, aryl, arylalkyl, heteroaryl, heteroarylalkyl, or $R^8$ and $R^9$, together with the N atom to which they are attached, form heterocyclic or heteroaryl;

$R^{10}$ is independently hydrogen, alkyl, cycloalkyl, perfluoroalkyl, alkenyl, alkynyl, heteroalkyl, heterocyclic, aryl, arylalkyl, heteroaryl, or heteroarylalkyl; and $R^{11}$ is independently hydrogen, alkyl, cycloalkyl, perfluoroalkyl, alkenyl, alkynyl, heteroalkyl, heterocyclic, aryl, arylalkyl, heteroaryl, or heteroarylalkyl;

with the provision that $R^1$ is not isopropyl.

In another aspect the disclosure provides compounds of Formula I, wherein $R^1$ is $-(CH_2)_jC(O)NR^3R^4$; and $R^3$ and $R^4$ are each independently hydrogen, substituted or unsubstituted alkyl, or substituted or unsubstituted arylalkyl.

In another aspect the disclosure provides compounds of Formula I, wherein $R^1$ is $-(CH_2)_jC(O)NR^3R^4$; j is 0; $R^3$ is hydrogen; and $R^4$ is $-CH_2CH(CH_3)C_6H_5$, $-CH_2(C_6H_4)CH_3$, or $-CH_2(C_6H_4)CH_2CH_3$.

In another aspect the disclosure provides compounds of Formula I, wherein $R^1$ is $-(CH_2)_jC(O)NR^3R^4$; j is 0; $R^3$ is hydrogen; and $R^4$ is

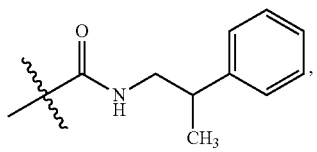

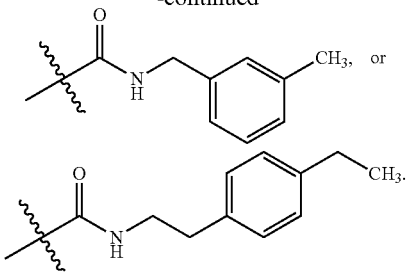

In another aspect the disclosure provides compounds of Formula I, wherein $R^1$ is $-(CH_2)_jC(O)R^2$; and $R^2$ is substituted or unsubstituted alkyl, substituted or unsubstituted arylalkyl.

In another aspect the disclosure provides compounds of Formula I, wherein $R^1$ is $-(CH_2)_jC(O)R^2$; j is 0; and $R^2$ is $CH_2C_6H_5$.

In another aspect the disclosure provides compounds of Formula I, wherein $R^1$ is substituted or unsubstituted alkyl or substituted or unsubstituted cycloalkyl.

In another aspect the disclosure provides compounds of Formula I, wherein $R^1$ is $(C_1-C_6)$alkyl.

In another aspect the disclosure provides compounds of Formula I, wherein $R^1$ is $-CH_3$, $-CH_2CH_3$, $-CH_2CH_2CH_3$, or $-CH_2CH(CH_3)_2$.

In another aspect the disclosure provides compounds of Formula I, wherein $R^1$ is $-(CH_2)_q(C_5H_9)$ or $-(CH_2)_q(C_6H_{11})$, wherein q is an integer from 0 to 6.

In another aspect the disclosure provides compounds of Formula I, wherein $R^1$ is substituted or unsubstituted arylalkyl.

In another aspect the disclosure provides compounds of Formula I, wherein $R^1$ is substituted or unsubstituted aryl($C_1$-$C_6$)alkyl.

In another aspect the disclosure provides compounds of Formula I, wherein $R^1$ is substituted or unsubstituted $-(C_1-C_6)$alkyl($C_6H_5$).

In another aspect the disclosure provides compounds of Formula I, wherein $R^1$ is

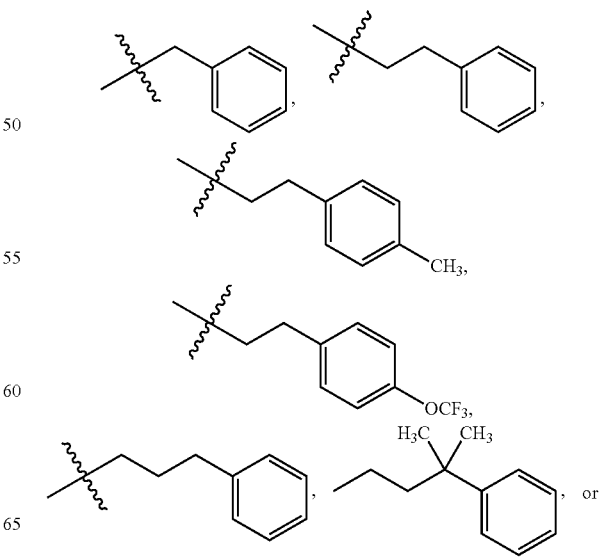

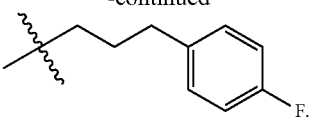

In another aspect the disclosure provides methods for treating a disease or a disorder, by administering to a subject in need thereof a therapeutically effective amount of a compound of Formula I, thereby treating the disease or the disorder.

In another aspect the disclosure provides methods for treating a disease or a disorder, by administering to a subject in need thereof a therapeutically effective amount of a compound of Formula I, wherein the disease or the disorder is cancer.

In another aspect the disclosure provides methods for treating a disease or a disorder, by administering to a subject in need thereof a therapeutically effective amount of a compound of Formula I, wherein the disease or the disorder is cancer, wherein cancer is lung cancer, breast cancer, prostate cancer, or lymphomas.

In another aspect the disclosure provides methods for treating a disease or a disorder, by administering to a subject in need thereof a therapeutically effective amount of a compound of Formula I, wherein the treatment includes inhibition of activity of at least one BCL-2 family protein.

In another aspect the disclosure provides methods for treating a disease or a disorder, by administering to a subject in need thereof a therapeutically effective amount of a compound of Formula I in combination with an anticancer agent.

In another aspect the disclosure provides methods for treating cancer or an autoimmune disease in a subject having at least one elevated BCL-2 family protein expression level by administering to the subject a therapeutically effective amount of a compound of Formula I, thereby treating the cancer or autoimmune disease.

In another aspect the disclosure provides methods for treating cancer or an autoimmune disease in a subject having at least one elevated BCL-2 family protein expression level by administering to the subject a therapeutically effective amount of a compound of Formula I, and determining whether the subject is responsive to a therapy that utilizes the compound, by determining the level of at least one of the BCL-2 family protein in the subject and comparing to a normal control sample, wherein an elevated level is indicative of a subject responsive to the therapy.

In another aspect the disclosure provides methods for treating cancer or an autoimmune disease in a subject having at least one elevated BCL-2 family protein expression level by administering to the subject a therapeutically effective amount of a compound of Formula I, and determining whether the subject is responsive to a therapy that utilizes the compound, by determining the level of at least one of the BCL-2 family protein in the subject and comparing to a normal control sample, wherein an elevated level is indicative of a subject responsive to the therapy, wherein the determination is made based on a sample from the subject.

In another aspect the disclosure provides methods for determining whether a subject is responsive to a therapy that utilizes a compound of Formula I, by determining the level of at least one of the BCL-2 family protein in the subject and comparing to a normal control sample, wherein an elevated level is indicative of a subject responsive to the therapy.

In another aspect the disclosure provides methods for determining whether a subject is responsive to a therapy that utilizes a compound of Formula I, by determining the level of at least one of the BCL-2 family protein in the subject and comparing to a normal control sample, wherein an elevated level is indicative of a subject responsive to the therapy, and wherein the determination is made based on a sample from the subject.

In another aspect the disclosure provides methods for determining whether a subject is responsive to a therapy that utilizes a compound of Formula I, by determining the level of at least one of the BCL-2 family protein in the subject and comparing to a normal control sample, wherein an elevated level is indicative of a subject responsive to the therapy, wherein the determination is made based on a sample from the subject, and wherein the sample is a biological fluid or tumor sample.

In another aspect the disclosure provides methods for determining whether a subject is responsive to a therapy that utilizes a compound of Formula I, by determining the level of at least one of the BCL-2 family protein in the subject and comparing to a normal control sample, wherein an elevated level is indicative of a subject responsive to the therapy, and wherein the BCL-2 family polynucleotide or polypeptide is BCL-2, BCL-XL, BCL-W, MCL-1, or BCL-A1.

In another aspect the disclosure provides methods for inducing apoptosis in a cell having a level of at least one of the BCL-2 family protein member greater than levels in a control cell, by administering to the cell an effective amount of a compound of Formula I, thereby reducing the level of BCL-2 family protein(s) and inducing apoptosis in the cell In another aspect the disclosure provides methods for inducing apoptosis in a cell having a level of at least one of the BCL-2 family protein member greater than levels in a control cell, by administering to the cell an effective amount of a compound of Formula I, thereby reducing the level of BCL-2 family protein(s) and inducing apoptosis in the cell, wherein the cell is a cancer cell.

In another aspect the disclosure provides methods for inducing apoptosis in a cell having a level of at least one of the BCL-2 family protein member greater than levels in a control cell, by administering to the cell an effective amount of a compound of Formula I, thereby reducing the level of BCL-2 family protein(s) and inducing apoptosis in the cell, wherein the cell is a cancer cell, and wherein cancer is lung cancer, breast cancer, prostate cancer, or lymphomas.

In another aspect the disclosure provides methods for inducing apoptosis in a cell having a level of at least one of the BCL-2 family protein member greater than levels in a control cell, by administering to the cell an effective amount of a compound of Formula I, thereby reducing the level of BCL-2 family protein(s) and inducing apoptosis in the cell, wherein the cell is a cell of the immune system.

In another aspect the disclosure provides methods for determining the effectiveness of a therapeutic regimen including administration of the compound of Formula I to a subject, by comparing the level of a BCL-2 family protein in a cell of the subject prior to and during treatment with the compound, wherein a decreased level of BCL-2 family protein is indicative of effectiveness of the therapy that utilizes the compound.

In another aspect the disclosure provides methods for determining the effectiveness of a therapeutic regimen including administration of the compound of Formula I in a subject, by comparing the level of a BCL-2 family protein in a cell of the subject prior to and during treatment with the compound, wherein a decreased level of BCL-2 family protein is indicative of effectiveness of the therapy that utilizes the compound, wherein the subject has cancer.

In another aspect the disclosure provides methods for determining the effectiveness of a therapeutic regimen including administration of the compound of Formula I in a subject, by comparing the level of a BCL-2 family protein in a cell of the subject prior to and during treatment with the compound, wherein a decreased level of BCL-2 family protein is indicative of effectiveness of the therapy that utilizes the compound, wherein the subject has cancer, and wherein cancer is lung cancer, breast cancer, prostate cancer, or lymphomas.

In another aspect the disclosure provides methods for determining the effectiveness of a therapeutic regimen including administration of the compound of Formula I in a subject, by comparing the level of a BCL-2 family protein in a cell of the subject prior to and during treatment with the compound, wherein a decreased level of BCL-2 family protein is indicative of effectiveness of the therapy that utilizes the compound, wherein the subject has cancer, and wherein cancer includes, but are not limited to, an alimentary/gastrointestinal tract cancer, colon cancer, liver cancer, skin cancer, breast cancer, ovarian cancer, prostate cancer, lymphoma, leukemia (including acute myelogenous leukemia and chronic myelogenous leukemia), kidney cancer, lung cancer, muscle cancer, bone cancer, bladder cancer or brain cancer.

In another aspect the disclosure provides methods for determining the effectiveness of a therapeutic regimen including administration of the compound of Formula I in a subject, by comparing the level of a BCL-2 family protein in a cell of the subject prior to and during treatment with the compound, wherein a decreased level of BCL-2 family protein is indicative of effectiveness of the therapy that utilizes the compound, wherein the subject has an autoimmune disorder.

In another aspect the disclosure provides methods for treating inflammation in a subject by administering to the subject in need of the treatment a pharmaceutically effective amount of a compound of Formula I, or a pharmaceutically acceptable salt, hydrate, or solvate thereof, to reduce the inflammation thereby, wherein $R^1$ is as describe above.

In another aspect the disclosure provides methods for treating a disease or a disorder, by administering to a subject in need thereof a therapeutically effective amount of a compound of Formula I, wherein the disease or disorder is lupus erythmatosus, psoriasis, psoriatic arthritis, lupus nephritis, rheumatoid arthritis, multiple sclerosis, ulcerative colitis, myasthenia gravis, ITP, TTP, Grave's disease, Hashimoto's thyroiditis, Crohn's disease, autoimmune hemolytic anemias, insulin dependent diabetes mellitus, glomerulonephritis, rheumatic fever, osteoarthritis, gouty arthritis, dermatitis, bronchitis, rhinitis, asthma, Sjogrens' syndrome, meningitis, adrenoleukodystrophy, CNS vasculitis, mitochondrial myopathies, Amyotrophic Lateral Sclerosis, Alzheimer's disease, or a tumor.

In another aspect the disclosure provides methods for treating a disease or a disorder, by administering to a subject in need thereof a therapeutically effective amount of a compound of Formula I, wherein the disease or disorder is a mitochondrial myopathy such as MELAS syndrome, MERF syndrome, Leber's disease, Wernicke's encephalopathy, Rett syndrome, homocystinuria, hyperprolinemia, nonketotic hyperglycinemia, hydroxybutyric aminoaciduria, sulfite oxidase deficiency, or combined systems disease (B12 deficiency).

In another aspect the disclosure provides methods for treating a disease or a disorder, by administering to a subject in need thereof a therapeutically effective amount of a compound of Formula I, by further administering a selective serotonin reuptake inhibitor (SSRI).

In another aspect the disclosure provides methods for treating inflammation in a subject by administering to the subject in need of the treatment a pharmaceutically effective amount of a compound of Formula I, by further administering a selective serotonin reuptake inhibitor (SSRI).

In another aspect the disclosure provides methods for treating inflammation in a subject by administering to the subject in need of the treatment a pharmaceutically effective amount of a compound of Formula I, wherein the inflammation is inflammation associated with a condition wherein the condition is lupus erythmatosus, psoriasis, psoriatic arthritis, lupus nephritis, rheumatoid arthritis, multiple sclerosis, ulcerative colitis, myasthenia gravis, ITP, TTP, Grave's disease, Hashimoto's thyroiditis, Crohn's disease, autoimmune hemolytic anemias, insulin dependent diabetes mellitus, glomerulonephritis, rheumatic fever, osteoarthritis, gouty arthritis, dermatitis, bronchitis, rhinitis, asthma, Sjogrens' syndrome, meningitis, adrenoleukodystrophy, CNS vasculitis, mitochondrial myopathies, Amyotrophic Lateral Sclerosis, Alzheimer's disease, or a tumor.

In another aspect the disclosure provides methods for treating inflammation in a subject by administering to the subject in need of the treatment a pharmaceutically effective amount of a compound of Formula I, wherein the inflammation is inflammation associated with a condition wherein the condition is a mitochondrial myopathy, wherein the mitochondrial myopathy is MELAS syndrome, MERF syndrome, Leber's disease, Wernicke's encephalopathy, Rett syndrome, homocystinuria, hyperprolinemia, nonketotic hyperglycinemia, hydroxybutyric aminoaciduria, sulfite oxidase deficiency, or combined systems disease (B12 deficiency).

Inflammation disorders may involve the activity of apoptotic regulators. Thus, it is desirable to identify compounds that modulate the activity of apoptotic regulators, such as BCL-2 proteins. Such compounds are described herein. In some embodiments, the binding of these compounds prevents the interaction of anti-apoptotic BCL-2 family members with pro-apoptotic BCL-2 family members, and thereby reduces the biological activity of anti-apoptotic BCL-2 family members. As a result, the compounds may be used to treat or prevent inflammatory disorders involving anti-apoptotic BCL-2 protein activity. In various embodiments, the compounds of interest comprise various derivatives of Apogossypolone having Formula I. These compounds may be administered to a patient with a high susceptibility to developing a condition associated with inflammation, for example, lupus erythematosus, to reduce the likelihood that the patient will develop such conditions.

The disclosure also provides prodrugs of Apogossypolone having Formula I. For example, when $R^1$ is the acetate moiety (—OC(O)CH$_3$) in Formula I, these compounds may be used as pro-drugs for the oral administration of the Apogossypolone derivatives. In another embodiment the compounds of the disclosure include compounds of Formula I, wherein the compound is substantially pure, such as more than about 85%, 90%, 95%, and 99%. For example, the compounds of Formula I may be purified to essential homogeneity.

Apogossypolone may be more efficacious than Gossypol, yet less toxic. The aldehydes in Gossypol make this compound reactive, thus effectively reducing the available concentrations of active drug and causing toxicity. Apogossypolone, a Gossypol analog without the problematic aldehydes, retains activity against anti-apoptotic BCL-2-family proteins. Daily dosing studies show that mice tolerate doses of Apogossypolone. Furthermore, Apogossypolone may be superior to parent compound Gossypol with respect to toxicology and efficacy. The use of Apogossypol for treating cancer is described in PCT Publication No. WO 2005/009434, filed Jun. 25, 2005, which is hereby incorporated by reference in its entirety. Given that Gossypol has toxicity problems likely due to two reactive aldehyde groups, the compounds of Formula I were designed to lack these aldehydes but retain activity against anti-apoptotic Bcl-2 family proteins in vitro and in cells.

Molecular docking studies of Apogossypol into the BH3 binding groove in Bcl-2 suggest that Apogossypol forms two hydrogen bonds with residues Arg 143 and Tyr 105 in Bcl-2 through 1 and 1' hydroxyl group, respectively. Apogossypol also forms hydrogen bonds with Trp141 and Tyr 199 in Bcl-2 through 6' hydroxyl group on the right naphthalene ring. The isopropyl group on the left naphthalene ring inserts into the first hydrophobic pocket (P1) in Bcl-2, while the isopropyl group on the right naphthalene ring inserts into the hydrophobic pocket (P2). Analysis of the predicted binding models indicates that while the overall core structure of Apogossypol fits rather well into BH3 binding groove of Bcl-2, the two isopropyl groups do not apparently fully occupy the hydrophobic pockets P1 and P2.

A general synthetic scheme that may be used to synthesize the compounds of the disclosure is provided below.

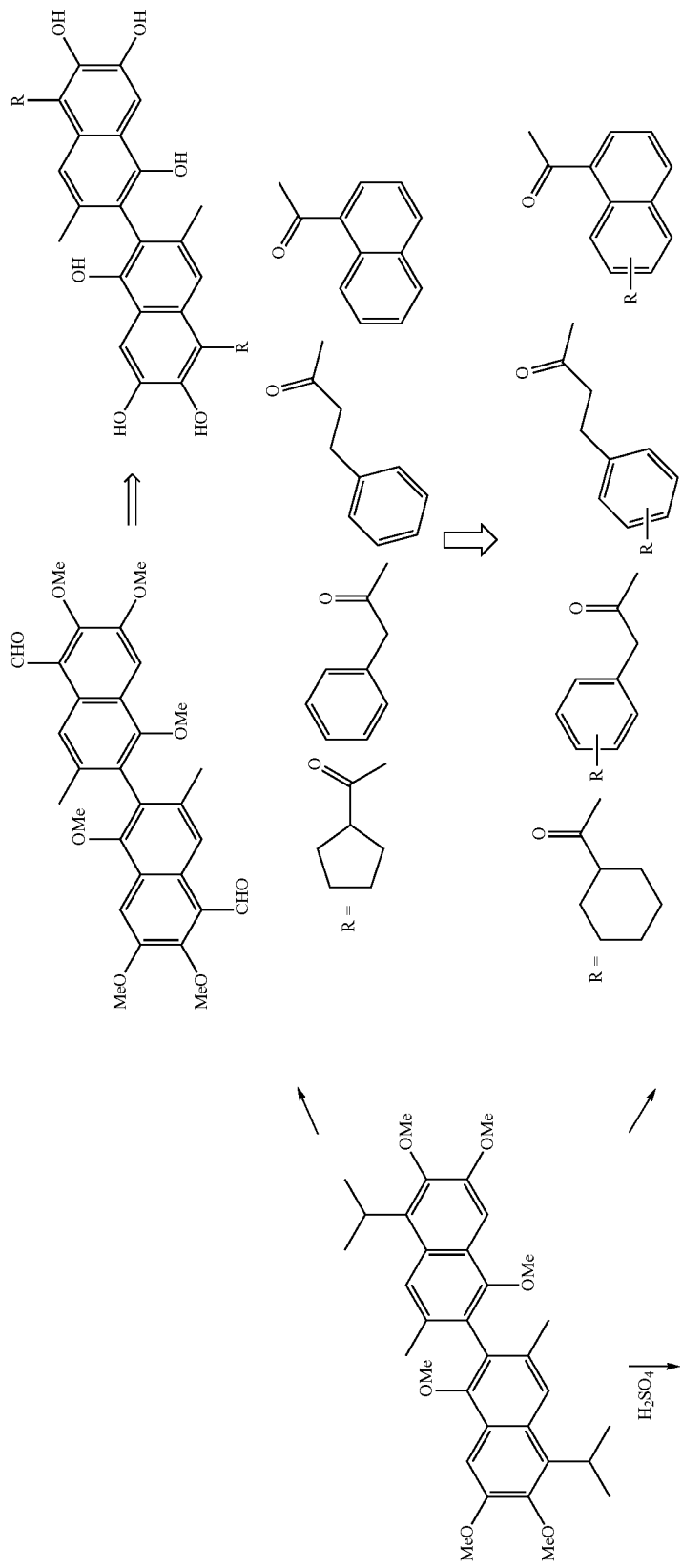

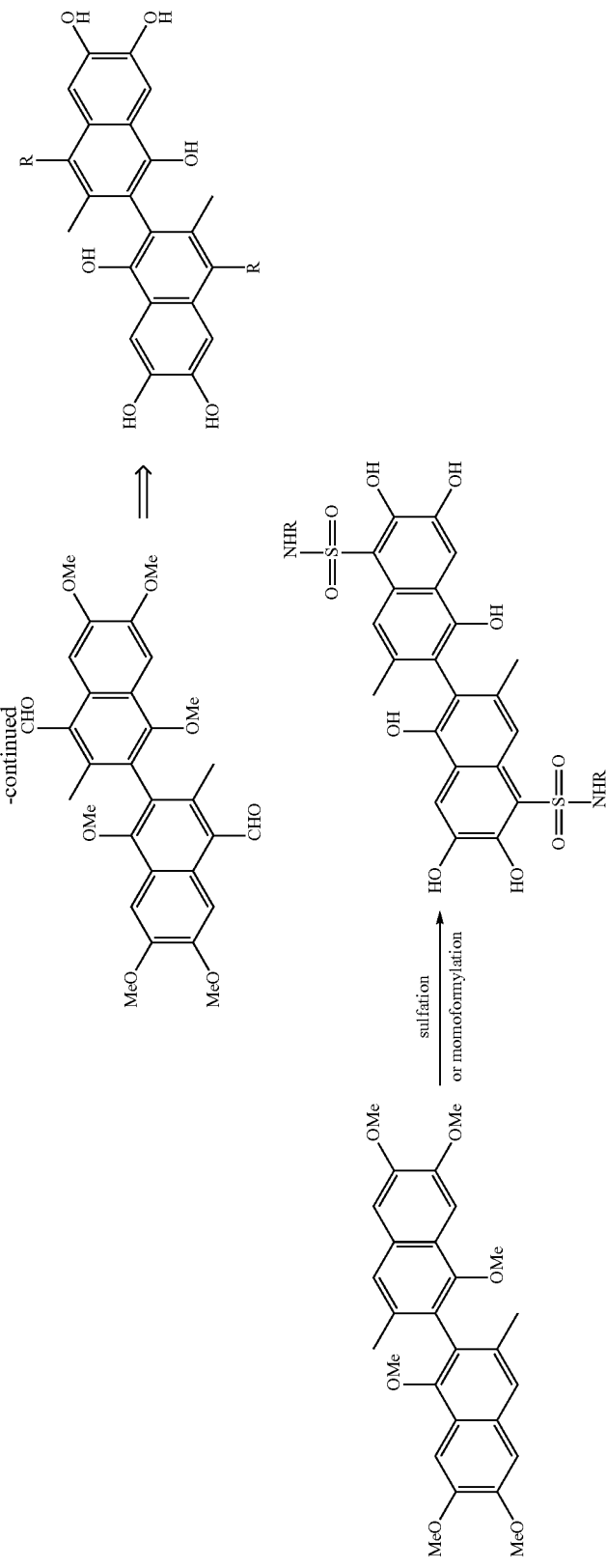

In particular, the synthesis of 5,5' amide substituted Apogossypolone derivatives of the compounds of Formula I is outlined below:

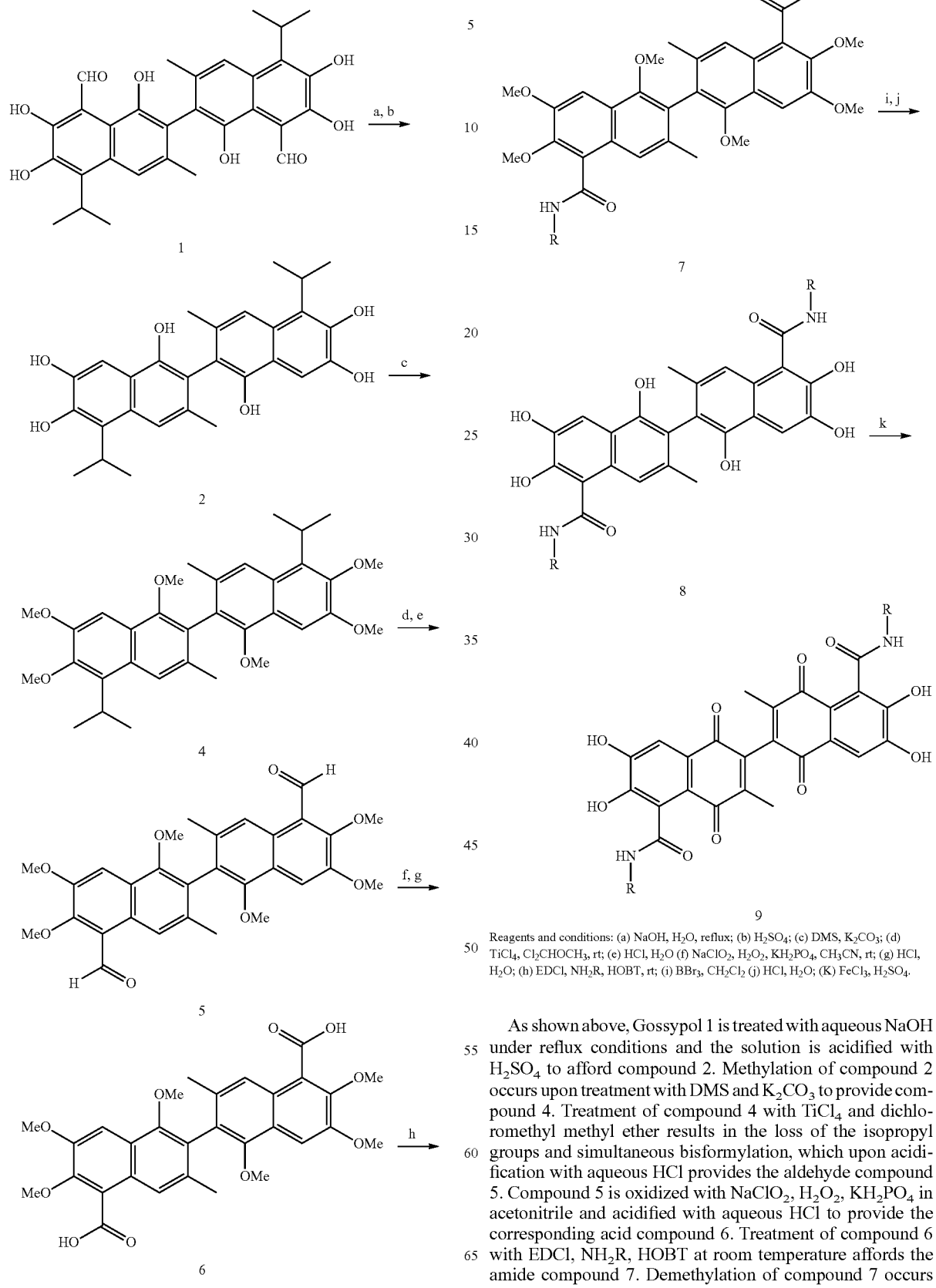

Reagents and conditions: (a) NaOH, H₂O, reflux; (b) H₂SO₄; (c) DMS, K₂CO₃; (d) TiCl₄, Cl₂CHOCH₃, rt; (e) HCl, H₂O (f) NaClO₂, H₂O₂, KH₂PO₄, CH₃CN, rt; (g) HCl, H₂O; (h) EDCl, NH₂R, HOBT, rt; (i) BBr₃, CH₂Cl₂ (j) HCl, H₂O; (K) FeCl₃, H₂SO₄.

As shown above, Gossypol 1 is treated with aqueous NaOH under reflux conditions and the solution is acidified with H₂SO₄ to afford compound 2. Methylation of compound 2 occurs upon treatment with DMS and K₂CO₃ to provide compound 4. Treatment of compound 4 with TiCl₄ and dichloromethyl methyl ether results in the loss of the isopropyl groups and simultaneous bisformylation, which upon acidification with aqueous HCl provides the aldehyde compound 5. Compound 5 is oxidized with NaClO₂, H₂O₂, KH₂PO₄ in acetonitrile and acidified with aqueous HCl to provide the corresponding acid compound 6. Treatment of compound 6 with EDCl, NH₂R, HOBT at room temperature affords the amide compound 7. Demethylation of compound 7 occurs upon treatment with BBr₃ in dichloromethane and acidification of the solution with aqueous HCl provides the amide compound 8. Finally, oxidation of compound 8 with FeCl₃ in H₂SO₄ provides the desired Apogossypolone derivative 9.

The synthesis of 5,5' alkyl substituted Apogossypolone derivatives of Formula I is outlined below.

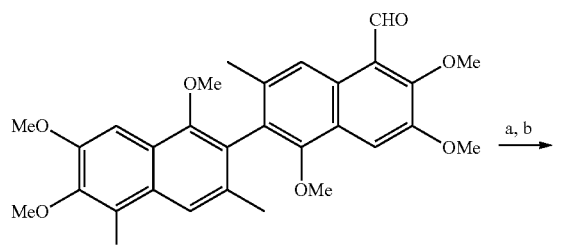

5

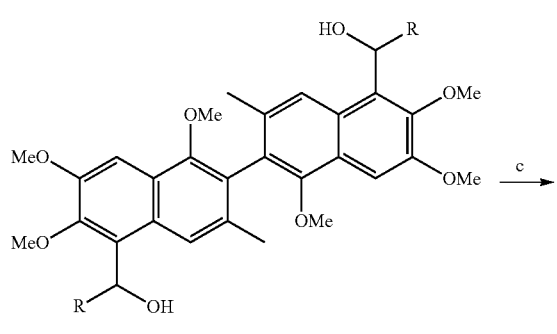

9

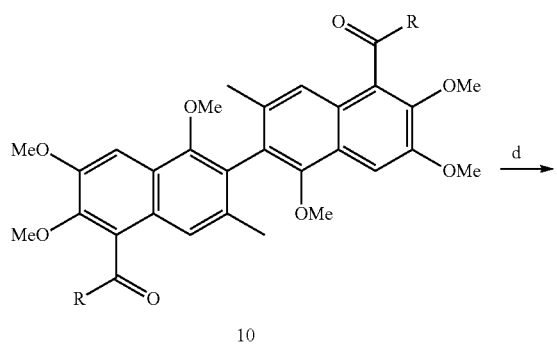

10

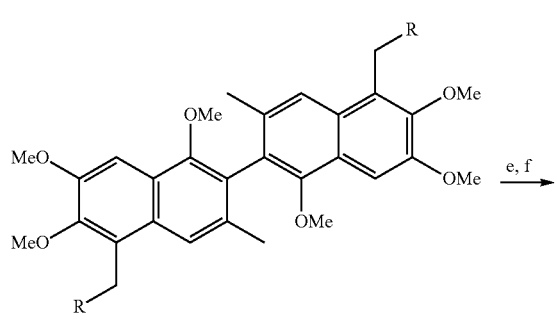

11

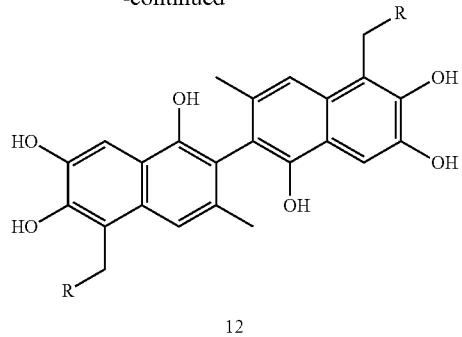

12

Reagents and conditions: (a) RMgBr or RLi, rt; (b) NH₄Cl, H₂O; (c) Pyridinium chlorochromate, CH₂Cl₂, rt; (d) Et₃SiH, TFA or Pd/C, H₂; (e) BBr₃; (f) HCl, H₂O.

Compound 5 was treated with different Grignard or lithium reagents to afford a secondary alcohol 9, which was oxidized to give the phenone 10 by pyridinium chlorochromate. Triethylsilane reduced phenone 10 to alkyl compound 11 followed by subsequent demethylation using boron tribromide to afford compound 12.

Compounds 13 and 14, with only hydrogen atom or carboxylic acid at 5,5' positions, were synthesized to explore if substitution at 5,5' position is important for enhancing biological activities. Compound 13 was synthesized by treating compound 4 with concentrated sulfuric acid to lose isopropyl group. The resulting product and compound 6 was then treated individually with boron tribromide to give compounds 13 and 14, respectively.

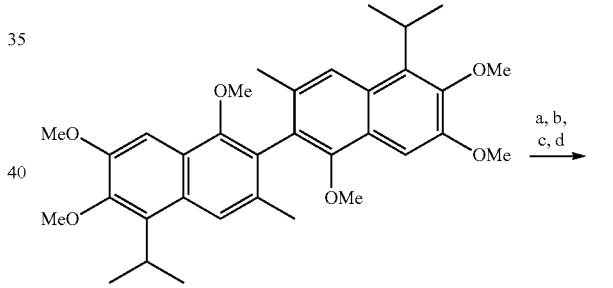

4

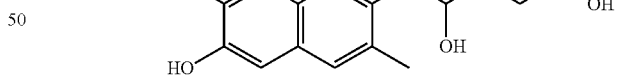

13

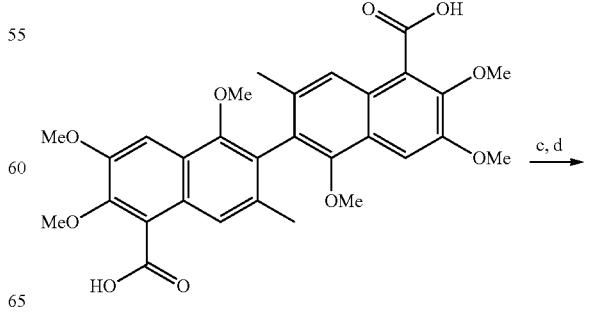

6

-continued

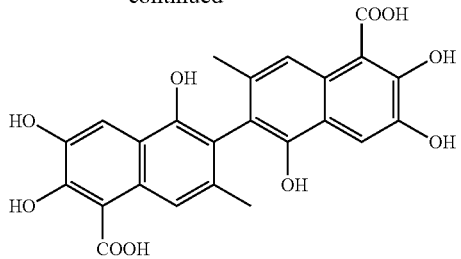

14

Reagents and conditions: (a) H$_2$SO$_4$, rt; (b) H$_2$O; (c) BBr$_3$, CH$_2$Cl$_2$; (d) HCl, H$_2$O.

The synthesis of 5,5' ketone substituted Apogossypolone derivatives of Formula I is outlined below:

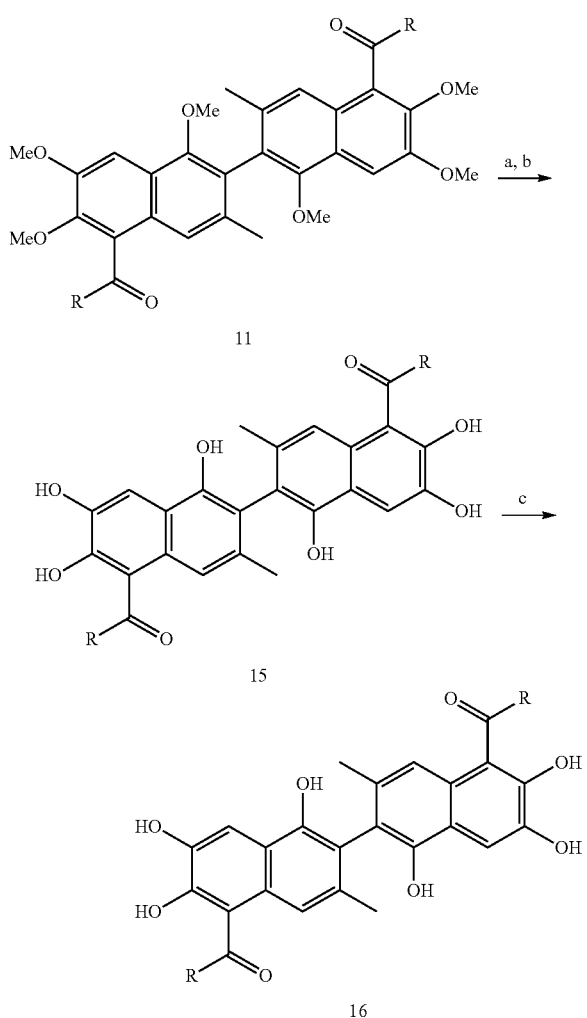

Reagents and conditions: (a) BBr$_3$; (b) HCl, H$_2$O; (c) FeCl$_3$, H$_2$SO$_4$.

As shown above, demethylation of ketone compound 11 occurs upon treatment with BBr$_3$ in dichloromethane and acidification of the solution with aqueous HCl provides compound 15. Oxidation of compound 15 with FeCl$_3$ in H$_2$SO$_4$ provides the desired Apogossypolone derivative 16.

The synthesized compounds of Formula I may be screened by one-dimensional $^1$H nuclear magnetic resonance spectroscopy (1D-$^1$H NMR) binding assays against Bcl-X$_L$. Active compounds in 1D-$^1$H NMR binding assays are then selected and evaluated in the Isothermal Titration Calorimetry assays (ITC), cell viability assays and competitive fluorescence polarization assays (FPA). A group of compounds of Formula I display high binding affinity for Bcl-X$_L$ in these assays. The most potent compounds induce significant chemical shift changes in the active site methyl groups (region between −0.38 and 0.42 ppm) in the one-dimensional $^1$H-NMR spectra of Bcl-X$_L$ and also have an IC$_{50}$ value in the FP displacement assays, which is more effective than Apogossypol. To confirm results of the NMR binding data and the FP assays, binding affinity of the compounds of Formula I for Bcl-X$_L$ using ITC assay were tested. In agreement with NMR binding and FPA data, the compounds of Formula I display potent binding affinity to Bcl-X$_L$ with a K$_d$ value that is more potent than Apogossypol (K$_d$=1.7 µM) in the same assay. Consistent with NMR binding, FPA, and ITC data, the compounds of Formula I display strong efficacy in inhibiting cell growth in PC3ML cells, which express high levels of Bcl-X$_L$.

Bcl-2 and Mcl-1 play critical roles in cell apoptosis and Bfl-1 has been suggested to be an important anti-apoptotic factor in large B-cell lymphomas among Bcl-2 family proteins. Therefore, the binding properties and specificity of selected Bcl-X$_L$ active compounds of Formula I may be evaluated against Bcl-2, Mcl-1 and Bfl-1 using FP assays. The compounds of Formula I display strong binding affinity for Bcl-2, Mcl-1 and Bfl-1, and inhibit Bcl-2, Mcl-1 and Bfl-1 with low IC$_{50}$ values, which are more potent than Apogossypol in similar FP assays. The compounds of Formula I may be further evaluated against H460, H1299 and BP3 cell lines, which express high levels of Bcl-2, Mcl-1 and Bfl-1, respectively. Consistent with FPA data, the compounds of Formula I display significant efficacy in inhibiting cell growth in H460 and BP3 cells with low IC$_{50}$ values, which are more potent than Apogossypol. Molecular docking studies of the compounds of Formula I demonstrate that 2-phenylpropyl groups at 5,5' positions inserted deeper into hydrophobic pockets (P1 and P2) in Bcl-2, hence occupying these regions more efficiently compared to isopropyl groups of Apogossypol. In addition, the carbonyl group on the right naphthalene ring also formed an additional hydrogen bond with residue Tyr199. Other compounds of Formula I may also display strong pan-active inhibitory properties against Bcl-2, Mcl-1 and Bfl-1.

The analysis of the structure-activity relationship (SAR) of synthesized compounds of Formula I reveals that substitution at 5,5' position may be important for achieving stronger binding affinity to Bcl-2 family proteins. Accordingly, the compounds of Formula I with hydrogen atoms or carboxylic acid groups on 5,5' positions, display weak or no inhibition in all assays. Analysis of the SAR of the 5,5' amide substituted compounds of Formula I indicate that longer and flexible hydrophobic groups show better efficacy than small, short and rigid hydrophobic groups. Replacement of small methylcyclopropane or short cyclopentyl groups by longer methylcyclohexyl group may significantly increase cell inhibition potency. Also, compounds of Formula I having phenethyl groups at 5,5' positions may display potent cell activity in the H460 and PC3ML cell lines while compounds of Formula I having phenyl group may display relatively weak cell activity. Based on the modeling prediction, this is likely because longer and flexible groups may insert deeper into the P1 and P2 pockets. The SAR of the 5,5' alkyl substituted compounds of Formula I was explored. In general, longer hydrophobic groups show improved potency. Compounds of Formula I with isobutyl and isopentyl groups display improved activity compared to Apogossypol with isopropyl groups. Again, compounds of Formula I with a phenethyl group may be more active than compounds with benzyl group.

The H460 cell line has been studied by several groups. A pan-Bcl-2 family inhibitor, GX15-070, may be tested in H460 cell line with an $IC_{50}$ value of 3.85 µM. BP3 is human diffuse large B-cell lymphoma (DLBCL) cell line overexpressing Bfl-1. The mRNA ratio of Bfl-1, Bcl-$X_L$ and Mcl-1 is approximately 10:3:1. As shown in Table 1, it was determined that BP3 cell overexpressed high level Bfl-1 and Mcl-1 by Western blot analysis.

TABLE 1

|  | Mcl-1 | Bcl-2 | Bcl-xl | Bfl-1 |
| --- | --- | --- | --- | --- |
| BP3 | +++ | No | + | +++ |
| RS4; 11 | No | ++++ | + | No |

4-point rating scale for western data:
++++: Very high level
+++: High level
++: Medium level
+: Low
No: Not Detectable The potent Bcl-$X_L$ and Bcl-2 antagonist ABT-737 displayed no cell activity against BP3 cell lines because ABT737 is not effective against Mcl-1 and Bfl-1.

The ability of the compounds of Formula I to induce apoptosis of the human lymphoma RS11846 cell line, which expresses high levels of Bcl-2 and Bcl-$X_L$, was evaluated. For these assays, Annexin V-FITC and propidium iodide (PI) double staining, followed by flow-cytometry analysis were used. The synthesized compounds of Formula I effectively induced apoptosis of the RS11846 cell line in a dose-dependent manner. In particular, the compounds of Formula I are effective with low $EC_{50}$ values, which is consistent with previous results in human cancer PC3ML and H460 cell lines. Again, the negative control compounds induced weak or no apoptosis of the RS11846 cell line.

The compounds of Formula I have cytotoxicity against Bax/Bak double knockout (DKO) mouse embryonic fibroblast cells (MEF) in which antiapoptotic Bcl-2 family proteins lack a cytoprotective phenotype. Some potent pan-active Bcl-2 compounds displayed slightly cytotoxicity in Bax/Bak double knockout mouse embryonic fibroblast cells (MEF/DKO) by killing 20-35% of them at 10 µM using FITC-Annexin V/PI assays, implying that those compounds displayed some off-target effects. However, those compounds displayed reduced off-target effects than Gossypol which displayed very similar cytotoxicity in MEF and MEF/DKO cells at 10 µM. In comparison, Apogossypol had reduced off-target effect but displayed weaker ability to induce apoptosis of the MEF cells compared to 5,5' amide substituted compounds of Formula I.

Apogossypol has a polyphenol scaffold with 6 hydroxyl groups on the naphthalene ring, which may be oxidized to quinones. Stabilized Apogossypol may be obtained by cocrystallizing it with ascorbic acid. Apogossypol can also be stabilized by introducing electron withdrawing groups, such as carbonyl groups on the naphthalene rings because these will decrease the electron density on the naphthalene ring and subsequently slow down oxidation rate and other side reactions. The chemical stability of solid compounds may be evaluated at room temperature. The stability of the compound was monitored using a combination of HPLC and LCMS. Overall, 5,5' amide substituted compounds of Formula I show superior chemical stability compared to Apogossypol. In particular, the compounds may be only 10% degraded after 60 days at room temperature while Apogossypol is almost 80% decomposed under same condition in the absence of ascorbic acid. Compounds having a phenethyl group at 5,5' position are also less stable than amide compounds due to lack of electron withdrawing groups.

To test the pharmacological properties of the compounds of Formula I, the in vitro plasma stability, microsomal stability, and cell membrane permeability may be determined. From these studies the compounds of Formula I display superior plasma and microsomal stability than Apogossypol. The compounds only degraded 4% and 11%, respectively, after 1 hour incubation in rat plasma while Apogossypol degraded 47% under the same conditions. In addition, the compounds degraded 24% and 10%, respectively, after 1 hour incubation in rat microsomal preparations while Apogossypol degraded 36% under same condition. The compounds also showed similar or improved cell membrane permeability compared to Apogossypol.

Using a combination of 1D $^1$H-NMR binding assays, FP assays, ITC assays, cytotoxicity assays and preliminary in vitro ADME data, the compounds of Formula I may be selected for further in vivo studies using B6Bcl-2 transgenic mice. B-cells of the B6Bcl-2 transgenic mice overexpress human Bcl-2 and accumulate in the spleen of mice. The spleen weight is used as an end-point for assessing in vivo activity as the weight is highly consistent in age- and sex-matched Bcl-2-transgenic mice and variability was within ±2% among control B6Bcl2 mice. The in vivo activities of the compounds were screened side by side with Apogossypol and Gossypol in a single Bcl-2 transgenic mouse with a single intraperitoneal (ip) injection at 72 µmol/kg. In agreement with all in vitro data, tested 5,5' amide substituted compounds of Formula I display superior in vivo activity compared to Apogossypol and Gossypol. In particular, the compounds induced more than 40% spleen weight reduction. Since the maximum spleen shrinkage would be no more than 50% in this experimental model, these compounds induced near maximal (85-95%) biological activity while Apogossypol and Gossypol only induced 40% of maximum reduction in spleen weight at same dose. Again, the negative control compounds displayed no activity in transgenic mice model, as expected. Overall tested 5,5' alkyl substituted compounds of Formula I display lower in vivo activity compared to 5,5' amide substituted compounds.

The mice treated with a compound of Formula I have more apparent signs of GI toxicity at 72 µmol/kg (50 mg/kg). In order to balance the toxicity and efficacy of compounds, the maximum tolerated dose (MTD) of the compounds was explored using a group of five mice. Mice were treated with a single dose of 100, 75, 50, 25 and 12.5 mg/kg (ip) and observed for a period of 14 days monitoring morbidity (body weight loss) and mortality. All mice were alive after 14 days and the maximum weight loss was observed at the fifth day which underwent 80-100% recovery after 14 days. The mice dosed at 25 and 12.5 mg/kg showed no weight loss while the mice dosed at 50 mg/kg displayed around 13% weight loss. Therefore, the MTD of the compounds having Formula I are likely between 25 mg to 50 mg/kg, approximately. Next, the in vivo activity and toxicity of the compounds having Formula I in groups of six mice each at dose of 42 mg/kg (60 tµmol/kg) was evaluated. Consistent with the single mouse experiment, the compound treatment of these mice resulted in a significant (~70%) reduction of spleen weight (P<0.0001) compared to the control group of six mice. All mice tolerated the treatment well and only mild signs of GI toxicity were observed. The average weight loss of mice was 7.8% during the course of this study.

The compounds of Formula I were synthesized and evaluated in a variety of in vitro and in vivo assays. The most potent compounds bind to Bcl-$X_L$, Bcl-2, Mcl-1 and Bfl-1 with low $IC_{50}$ values. These compounds also may potently inhibited growth in cell cultures of the PC3ML, H460, H1299 and BP3 cancer cell lines, which express Bcl-$X_L$, Bcl-2, Mcl-1 and Bfl-1, respectively, with $EC_{50}$ values in the submicromolar to nanomolar range. These compounds also may effectively induced apoptosis of the RS11846 human lymphoma cell line in a dose-dependent manner and show little cytotoxicity against Bax/Bak double knockout mouse embryonic fibroblast cells in which antiapoptotic Bcl-2 family proteins lack a cytoprotective phenotype, implying that these compounds have little off-target effects. Finally, these compounds show favorable chemical stability, in vitro ADME properties and superior in vivo efficacy compared to Apogossypol in Bcl-2 transgenic mice in which Bcl-2 is overexpressed in B-cells. Thus, the critical roles of anti-apoptotic Bcl-2 family proteins in tumorgenesis, chemoresistance, and the potent inhibitory activity of the compounds of Formula I against anti-apoptotic Bcl-2 family proteins, provide important apoptosis-based cancer therapies.

Binding of the disclosed compounds to anti-apoptotic BCL-2 proteins can induce apoptosis and thereby treat inflammation and/or inflammatory disorders. In some embodiments, disclosed compounds can bind to anti-apoptotic BCL-2 family proteins such as, for example, BCL-2 or BCL-$X_L$. This binding can inhibit binding of the anti-apoptotic BCL-2 family members to pro-apoptotic BCL-2 family members. In various embodiments, binding of disclosed compounds can reduce the formation of complexes between anti-apoptotic BCL-2 proteins and the BH3 domain of pro-apoptotic BCL-2 family members.

Guided by a combination of nuclear magnetic resonance (NMR) binding assays and computational docking studies, a series of compounds having Formula I may be synthesized as potent pan-active inhibitors of anti-apoptotic Bcl-2 family proteins. One of the most potent compound, 8r, inhibits the binding of BH3 peptides to Bcl-$X_L$, Bcl-2, Mcl-1 and Bfl-1 with $IC_{50}$ values of 0.76 µM, 0.32 µM, 0.28 µM and 0.73 µM, respectively. This compound also potently inhibits cell growth in the 1-1460 human lung cancer and BP3 B-cell lymphoma cell lines with $EC_{50}$ values of 0.33 µM and 0.66 µM, respectively. Compound 8r effectively induces apoptosis of the RS11846 human lymphoma cell line in a dose-dependent manner and shows little cytotoxicity against bax$^{-/-}$ bak$^{-/-}$ cells in which antiapoptotic Bcl-2 family proteins lack a cytoprotective phenotype, implying that compound 8r has little off-target effect. Compound 8r also displays in vivo efficacy in transgenic mice in which Bcl-2 is overexpressed in splenic B-cells. Together with its improved chemical, plasma and microsomal stability relative to Apogossypol, Compound 8r provides an apoptosis-based therapy for cancer.

Gossypolone 5, a major metabolite of compound 1 formed by oxidation, displayed similar cytotoxic effects as compound 1 on several cancer cell lines and has been recently proposed for treatment of cancer. Apogossypolone (6a or ApoG2), a derivative of 5, has as well been reported as a potent inhibitor of Mcl-1 and Bcl-2 proteins. Compound 6a blocks binding of Bim and Bcl-2 and induced apoptosis in a number of human cancer cell lines. Compound 6a also induced regression in several tumor xenograft models and its maximum tolerated dose (MTD) when administered orally is above 240 mg/kg while the MTD of (–) 1 is 50 mg/kg. It is therefore attractive to further explore whether 6a derivatives displayed similar or improved biological activities compared to 6a. It was envisioned that 5,5' substitution of 6a could result in compounds with improved biological activities. The synthesis and biological evaluation of novel 5,5' substituted 6a derivatives (6-8) which replace the isopropyl groups of 6a with various alkyl (6), ketone (7) and amide (8) groups at 5,5' positions are provided herein.

Thus, in another embodiment, a general synthetic scheme that may be used to synthesize the compounds of the disclosure is provided below.

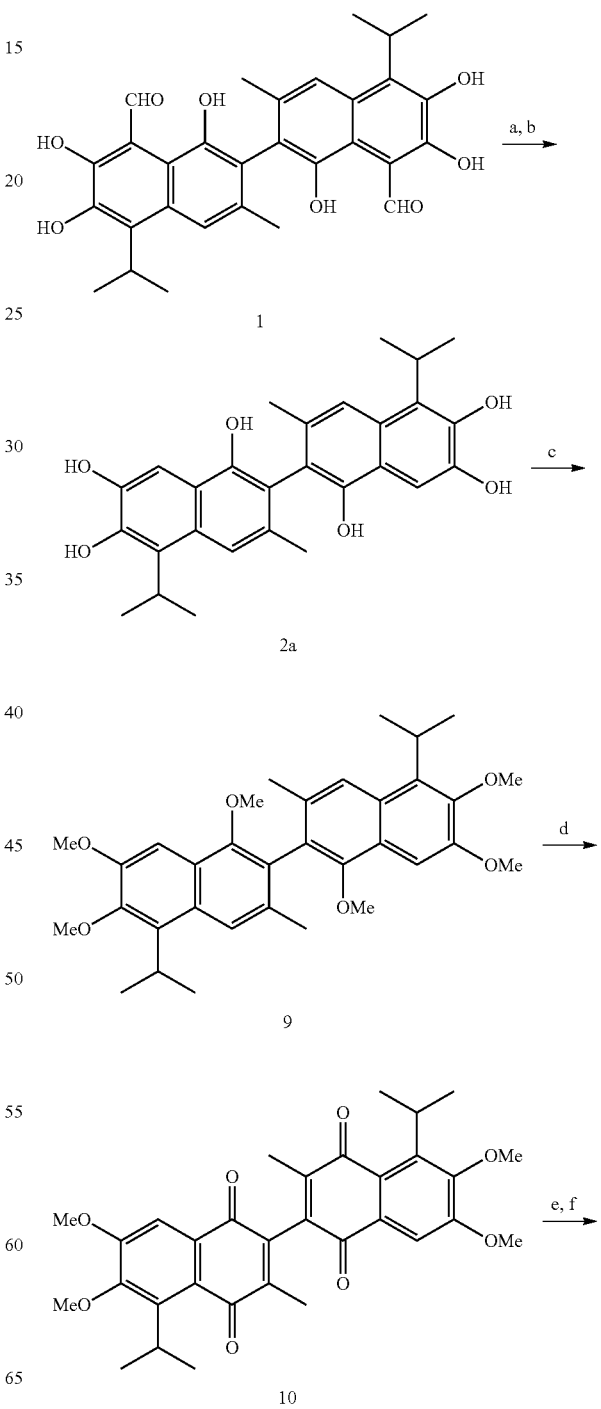

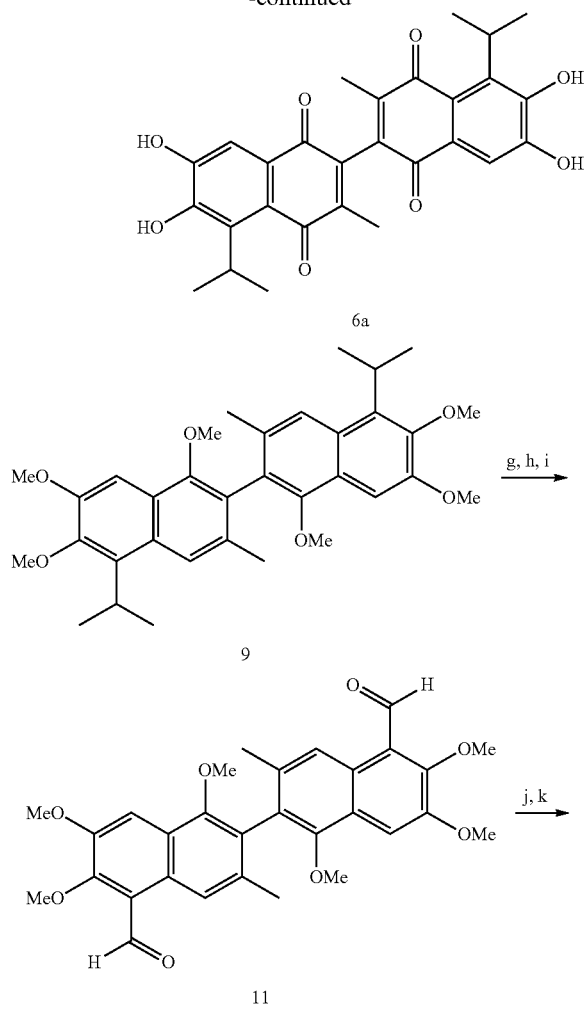
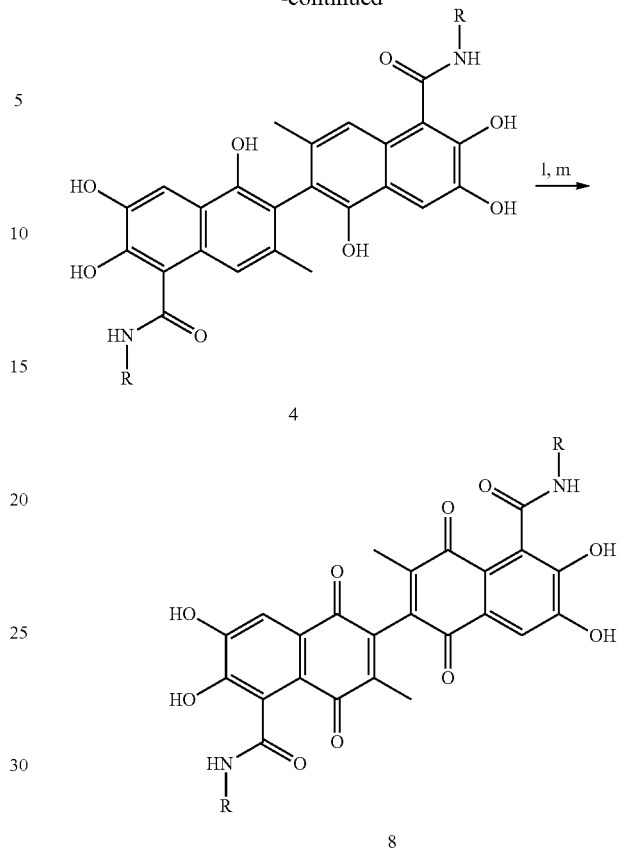

Reagents and conditions: (a) NaOH, $H_2O$, reflux; (b) $H_2SO_4$; (c) DMS, $K_2CO_3$; (d) $H_5IO_6$, 95° C.; (e) $BBr_3$, $CH_2Cl_2$; (f) HCl, $H_2O$; (g) $TiCl_4$, rt; (h) $Cl_2CHOCH_3$, rt; (i) HCl, $H_2O$; (j) $NaClO_2$, $H_2O_2$, $KH_2PO_4$, $CH_3CN$, rt; (k) EDCI, $NH_2R$, HOBT, rt; (l) $FeCl_3$, $CH_3COOH$, 60° C.; (m) 20% $H_2SO_4$.

Compound 1 was treated with NaOH solution at 90° C. to provide compound 2a, which was readily methylated in the presence of potassium carbonate to afford compound 9. Compound 9 was oxidized to compound 10 using periodic acid. Subsequent demethylation of the compound 10 using boron tribromide afforded compound 6a. Reaction of compound 9 with $TiCl_4$ followed by dichloromethyl methyl ether resulted in loss of isopropyl groups and simultaneous bisformylation to give aldehyde compound 11. The aldehyde groups of compound 11 were oxidized and coupled with a variety of commercially available amines in the presence of 1-ethyl-3-(3'-dimethylaminopropyl)carbodiimide (EDCI) to afford amide compound 12. Subsequent demethylation of compound 12 affords compound 4. Several oxidation reagents such as [bis(trifluoroacetoxy)iodo]benzene, potassium nitrosodisulfonate and ferric chloride were used to converted phenol 4 to quinone 8 and the ferric chloride is the most efficient oxidation reagent for this conversion in our hand.

The synthesis of 5,5' alkyl substituted 6a derivatives is outlined below:

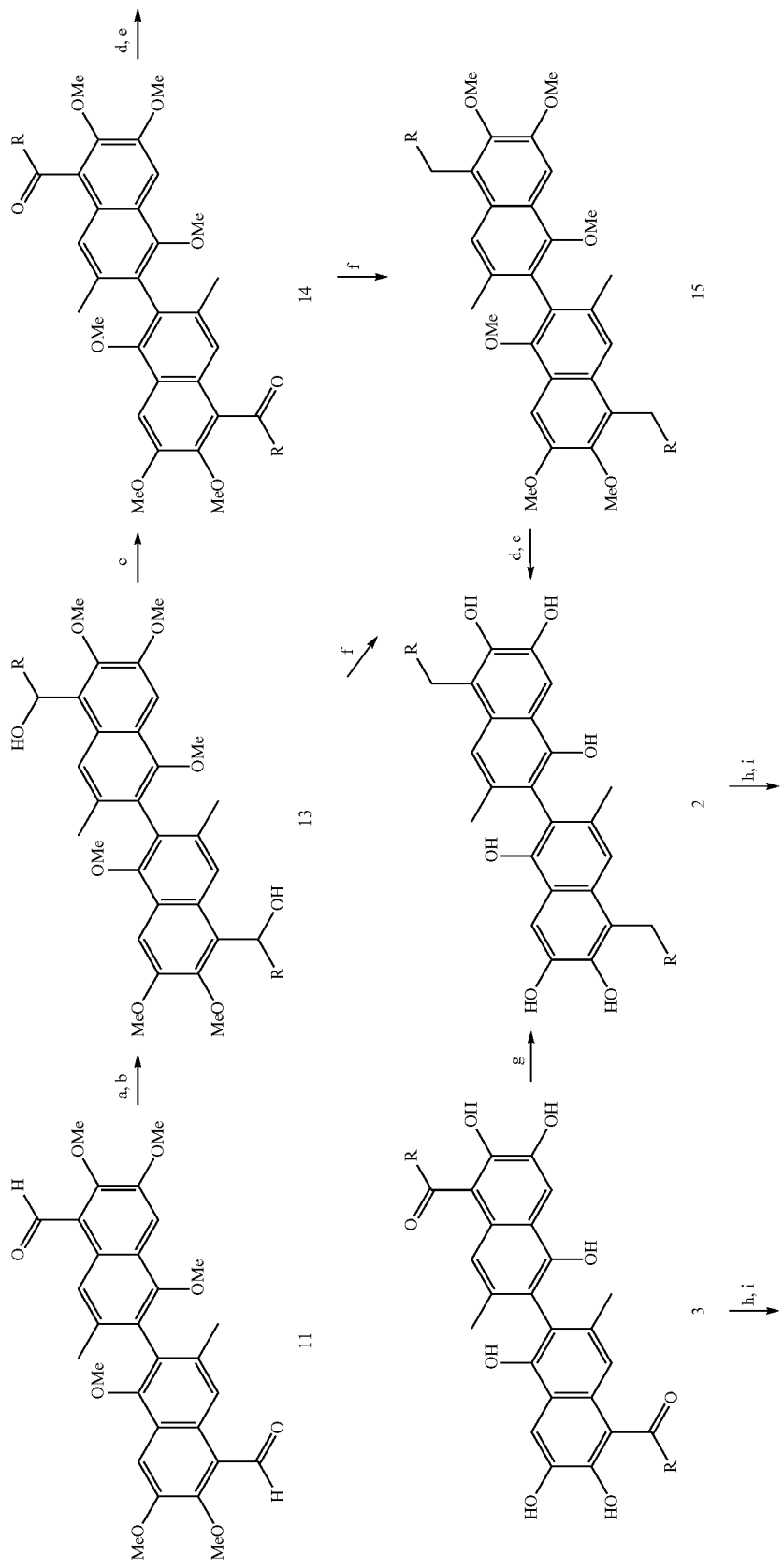

-continued
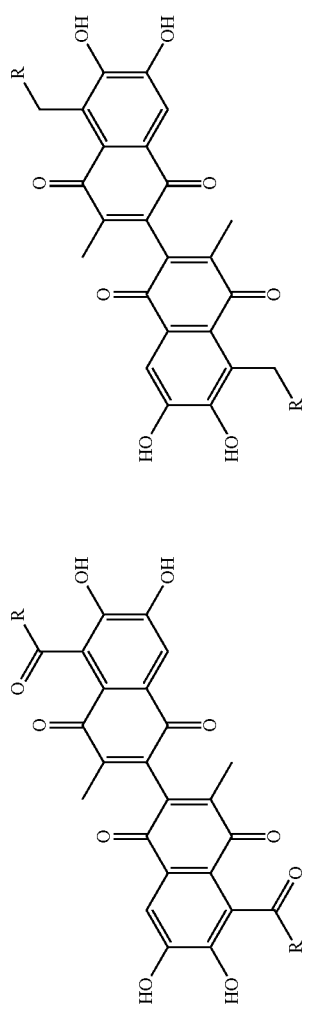
Reagents and conditions: (a) RMgBr or RLi, rt; (b) NH₄Cl, H₂O; (c) Pyridinium chlorochromate, CH₂Cl₂, rt; (d) BBr₃; (e) HCl, H₂O; (f) Et₃SiH, TFA; (g) Pd/C, H₂, CH₃COOH; (h) FeCl₃, CH₃COOH, 60° C.; (i) 20% H₂SO₄

Compound 11 was treated with different Grignard or lithium reagents to afford a secondary alcohol 13, which was oxidized to give the phenone 14 by pyridinium chlorochromate. Alcohol 13 and phenone 14 were readily reduced using triethylsilane to afford alkyl compound 15. Compound 15 was then demethylated using boron tribromide to afford compound 2. Oxidation of compound 2 using ferric chloride gave 6 as 5,5' alkyl substituted 6a derivatives. The reduction of ketone 3 using $H_2$ in the presence of Pd/C also afforded compound 2. Demethylation of compound 14 followed by ferric chloride oxidation afforded compound 7 as a 5,5' ketone substituted 6a derivative.

The synthesized 5,5' substituted 6a derivatives were first screened by one-dimensional $^1$H nuclear magnetic resonance spectroscopy (1D $^1$H NMR) binding assays against Bcl-$X_L$. A group of compounds (6a, 6b, 6f, 6i, 6l, 6m, 7,8a-c) induced chemical shift changes in active site methyl groups (region between −0.38 and 0.42 ppm) in the one-dimensional $^1$H-NMR spectra of Bcl-$X_L$. As shown in Table 2, the 5,5'-substituted 6a derivatives were evaluated using a combination of 1D $^1$H-NMR binding assays and cell viability assays.

TABLE 2

| Compound | R = | 1D-$^1$H NMR[a*] | PC3[b*] (μM) | H460[b*] (μM) | H1299[b*] (μM) | BP3[c*] (μM) | RS4;11[c*] (μM) |
|---|---|---|---|---|---|---|---|
| 6a | 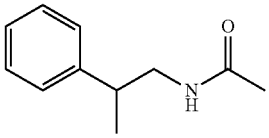 | +++ | 1.46 ± 0.33 | 0.40 ± 0.07 | 2.76 ± 0.72 | 11.73 ± 2.15 | 7.47 ± 2.78 |
| 8a | 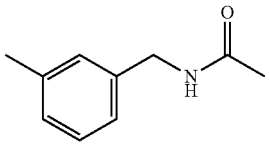 | +++ | 7.6 ± 1.41 | 5.75 ± 1.34 | >30 | 12.9 ± 1.91 | >30 |
| 8b | 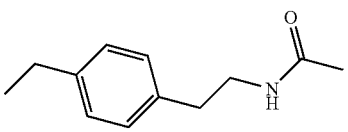 | +++ | 5.44 ± 0.34 | 6.16 ± 1.48 | >30 | 21.64 ± 0.85 | >30 |
| 8c | 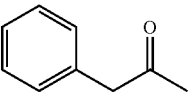 | +++ | 7.70 ± 0.64 | 4.40 ± 0.70 | 9.10 ± 5.20 | 22.23 ± 1.43 | >30 |
| 7 |  | +++ | 5.44 ± 0.24 | 7.38 ± 1.07 | >30 | 9.58 ± 4.16 | >30 |
| 6b | 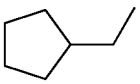 | +++ | 8.50 ± 2.89 | 0.73 ± 0.29 | 10.64 ± 5.02 | 10.93 ± 0.43 | 11.72 ± 0.68 |
| 6c | 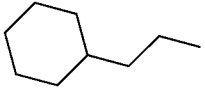 | + | 5.50 ± 0.74 | 0.70 ± 0.34 | 2.32 ± 0.51 | 12.84 ± 1.16 | 9.83 ± 0.26 |
| 6d |  | + | 2.40 ± 0.24 | 2.20 ± 0.76 | 1.32 ± 0.30 | 15.61 ± 0.10 | 15.43 ± 1.86 |

TABLE 2-continued

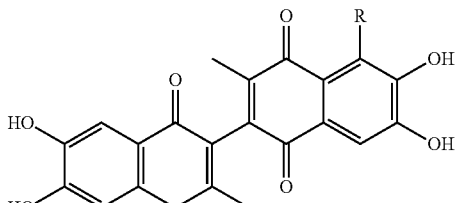

| Compound | R = | 1D-¹H NMR[a*] | PC3[b*] (µM) | H460[b*] (µM) | H1299[b*] (µM) | BP3[c*] (µM) | RS4;11[c*] (µM) |
|---|---|---|---|---|---|---|---|
| | | | | | EC$_{50}$ (µM) | | |
| 6e | 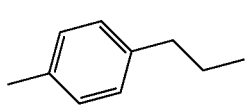 | ++ | 1.40 ± 0.14 | 1.04 ± 0.13 | 0.85 ± 0.36 | 8.72 ± 2.53 | 4.75 ± 0.01 |
| 6f | 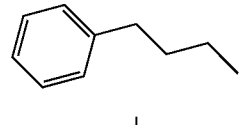 | ++ | 1.10 ± 0.08 | 0.59 ± 0.06 | 1.56 ± 0.17 | 4.18 ± 0.50 | 3.08 ± 0.59 |
| 6g | 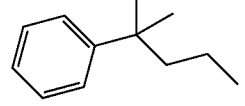 | ++ | 1.30 ± 0.18 | 0.92 ± 0.09 | 1.53 ± 0.41 | 6.0 ± 0.10 | 3.83 ± 0.70 |
| 6h | 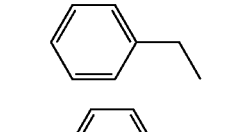 | ++ | 2.00 ± 0.17 | 1.62 ± 0.16 | 2.16 ± 0.27 | 30.0 ± 2.40 | 15.0 ± 0.24 |
| 6i | 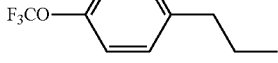 | +++ | 0.59 ± 0.22 | 0.13 ± 0.08 | 0.31 ± 0.19 | 10.1 ± 0.04 | 6.9 ± 1.76 |
| 6j | 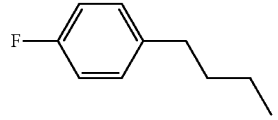 | + | 8.99 ± 2.49 | 1.44 ± 0.20 | 2.38 ± 0.21 | 16.12 ± 0.07 | 7.32 ± 0.90 |
| 6k | 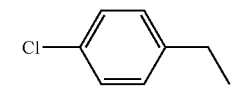 | + | 2.62 ± 0.31 | 1.48 ± 0.02 | 1.91 ± 0.17 | 14.61 ± 0.06 | 11.25 ± 0.54 |
| 6l | 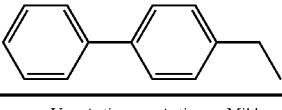 | +++ | 0.21 ± 0.05 | 0.19 ± 0.04 | 2.99 ± 1.21 | 0.48 ± 0.01 | 1.13 ± 0.60 |
| 6m |  | +++ | 2.97 ± 0.98 | 0.98 ± 0.15 | 10.30 ± 3.84 | 0.81 ± 0.06 | 1.74 ± 0.11 |

[a*]4-point-rating scale: +++: Very Active; ++: Active; +: Mild; −: Weak
[b*]Compounds against cell line using ATP-LITE assay
[c*]Compounds against cell line using Annexin V-FITC and propidium iodide assay To confirm the results from the 1D ¹H NMR binding assay described above, ¹⁵N-labeled Bcl-X$_L$ protein was produced and measured by 2D [¹⁵N, ¹H]-HSQC correlation spectra in absence and presence of selected compounds. Consistent with 1D ¹H NMR binding assays, compounds 6f, 6i and 8a displayed strong binding to Bcl-X$_L$, as qualitatively evaluated by the nature of the shifts at the ligand/protein ratio of 1:1. To confirm the results of the NMR binding data, the binding affinity of selected compounds for Bcl-X$_L$ using FP assay were evaluated. Table 3 demonstrates the cross-activity of selected 5,5' substituted 6a derivatives against Bcl-X$_L$, Bcl-2, Mcl-1 and Bfl-1.

TABLE 3

| Compound | IC$_{50}$ (µM) FPA | | | | K$_d$ (µM) ITC |
| --- | --- | --- | --- | --- | --- |
| | Bcl-X$_L$ | Bcl-2 | Bfl-1 | Mcl-1 | Bcl-X$_L$ |
| 6a | 0.63 ± 0.02 | 0.37 ± 0.02 | 2.17 ± 0.35 | 0.54 ± 0.03 | 2.80 ± 0.60 |
| 6b | 0.55 ± 0.06 | 0.25 ± 0.02 | 1.41 ± 0.11 | 0.47 ± 0.03 | 1.50 ± 0.80 |
| 6f | 3.10 ± 0.28 | 3.12 ± 0.15 | 14.7 ± 6.63 | 2.05 ± 0.15 | 2.50 ± 2.20 |
| 6i | 0.34 ± 0.03 | 0.29 ± 0.01 | 0.65 ± 0.05 | 0.24 ± 0.02 | 0.45 ± 0.26 |
| 6c | 2.99 ± 0.16 | 2.27 ± 0.15 | ND$^{a}$* | 3.08 ± 0.17 | ND |
| 6d | 12.65 ± 4.34 | 6.73 ± 2.24 | ND | 5.90 ± 0.54 | ND |
| 6e | 1.79 ± 0.14 | 2.57 ± 0.12 | 9.72 ± 1.38 | 1.29 ± 0.05 | ND |
| 6g | 1.44 ± 0.06 | 2.17 ± 0.14 | 5.27 ± 0.76 | 0.67 ± 0.03 | ND |
| 6l | 0.15 ± 0.06 | 0.34 ± 0.06 | 0.70 ± 0.07 | 0.40 ± 0.05 | ND |
| 7 | 0.34 ± 0.02 | 0.22 ± 0.02 | 0.69 ± 0.03 | 0.35 ± 0.02 | ND |
| 8a | 0.32 ± 0.01 | 0.23 ± 0.01 | 0.71 ± 0.06 | 0.47 ± 0.03 | ND |
| 8c | 0.24 ± 0.02 | 0.21 ± 0.01 | 1.25 ± 0.09 | 0.32 ± 0.02 | ND |

ND$^{a}$* = Not determined

In agreement with NMR binding, compound 6f displayed potent binding affinity to Bcl-X$_L$ with an IC$_{50}$ value of 3.1 µM in FP assay. A group of compounds (6a, 6b, 6i, 6l, 6m, 7, 8a, 8c) were 5-19 times more potent than 6f, with IC$_{50}$ values ranging from 0.16 to 0.63 µM in same assay. Compound 6f inhibits the binding of BH3 peptides to Bcl-X$_L$, Bcl-2 and Mcl-1 with IC$_{50}$ values of 3.10, 3.12 and 2.05 µM, respectively. In a cellular assay, 6f potently inhibits cell growth in several human cancer cell lines in a dose-dependent manner. Compound 6f further displays in vivo efficacy in transgenic mice and demonstrated superior single-agent antitumor efficacy in a PPC-1 mouse xenograft model. Together with its negligible toxicity, compound 6f represents a promising drug for the development of novel apoptosis-based therapies for cancer.

To further confirm results of the NMR binding data and the FP assays, the binding affinity of selected compounds (6a, 6b, 6f, 6i) for Bcl-X$_L$ using isothermal titration calorimetry (ITC) was evaluated. In agreement with NMR binding and FPA data, compound 6f displayed high binding affinity to Bcl-X$_L$ with a K$_d$ value of 2.5 µM by ITC and compound 6i showed increased binding affinity with a K$_d$ value of 0.45 µM in same assay. Compound 6a showed similar binding affinity with 6f with a K$_d$ value of 2.80 µM by ITC. Consistent with the NMR binding, FPA and ITC data, compounds 6a, 6d-6g, 6i and 6l-m displayed potent efficacy in inhibiting cell growth in a 3 day ATP-Lite assay in the PC3 cell line, which expresses high levels of Bcl-X$_L$. The average EC$_{50}$ value of 6i, 6l and 6m is 0.60 µM, hence 2.5-fold more potent than 6a (EC$_{50}$=1.5 µM. Compound 6f (EC$_{50}$=1.1 µM) displayed similar efficacy in inhibiting PC3 cell growth as the potent compound 6a in same assay. However, although compounds 8a and 8c displayed strong binding affinity to Bcl-X$_L$ in the NMR binding assay and FP assay, they showed relative weaker efficacy in inhibiting growth of PC3 cells with EC$_{50}$ values around 7.6 µM. The discrepancy is likely due to high hydrophilicity and molecular weight of 8a and 8c, which may result in low cell permeability. Cell permeability of selected compounds was therefore evaluated using the parallel artificial membrane permeability assay (PAMPA). As anticipated, compounds 8a has a lower LogPe value of −7.9 indicating poor cell membrane permeability while the LogPe value of 6f is −5.6 indicating excellent cell membrane permeability. Compared to 6f, compound 6a also has relatively lower cell membrane permeability (LogPe=−5.9).

In addition to Bcl-X$_L$, other members of the Bcl-2 family are known to play critical roles in tumor survival. Therefore, further evaluation of the binding properties and specificity of selected 5,5' substituted 6a derivatives against Bcl-2, Mcl-1 and Bfl-1 using FP assays were undertaken. Compound 6f displayed potent binding affinity against Bcl-2 (IC$_{50}$=3.12 µM), Mcl-1 (IC$_{50}$=2.05 µM) and relative lower affinity against Bfl-1 (IC$_{50}$=14.0 µM) in FP assays. Compound 6f was further evaluated against H460 and H1299 cancer cell lines, which express high levels of Bcl-2 and Mcl-1, respectively. Consistent with FPA data, compound 6f displayed potent efficacy in inhibiting cell growth in H460 and H1299 cell lines in a 3 day ATP-Lite assay, with EC$_{50}$ values of 0.59 µM and 1.5 µM, respectively, which is comparable with 6a. Molecular docking studies of compound 6f demonstrated that 1-methyl-4-propylbenzene groups at 5,5' positions inserted deeper into hydrophobic pockets (P1 and P2) in Bcl-2. Based on the docking models, compound 6f also forms two hydrogen bonds with residues Arg 143 and Tyr 199 in Bcl-2 through the 1' oxygen and 6' hydroxyl groups, respectively. In addition, the 7' hydroxyl group on the right naphthalene ring also formed an additional hydrogen bond with residue Tyr141. Other 5,5' substituted 6a derivatives, such as 6b, 6i, 6l and 6m also displayed strong pan-active inhibitory properties against Bcl-2, Mcl-1 and Bfl-1. The most potent compound 6i displaces BH3 binding to Bcl-2, Mcl-1 and Bfl-1 with IC$_{50}$ values of 0.29, 0.24 and 0.65 µM, respectively, in FP assays. In agreement with these FPA results, the compound 6i showed potent cell growth inhibitory activity against the H460 and H1299 cell lines in a 3 day ATP-Lite assay, with IC$_{50}$ values of 0.13 and 0.31 µM, respectively. The H460 cell line has been studied by several groups with respect to sensitivity to Bcl-2 antagonists. However, although compounds 7, 8a and 8c display potent binding affinity to Bcl-2 and Mcl-1 with average IC$_{50}$ values of 0.22 µM and 0.38 µM, respectively, in FP assays, they showed relative weak efficacy in inhibiting growth of H460 and H1299 cells with average EC$_{50}$ values of around 5.8 µM and 17 µM, respectively. This discrepancy is partially due to high hydrophilicity and molecular weight of 5,5' substituted ketone and amide 6a derivatives, resulting in reduced cell permeability.

The ability of 5,5' substituted 6a derivatives to induce apoptosis of the human leukemia RS4; 11 cell line (which expresses high levels of Bcl-2 and Bcl-X$_L$) and human lymphoma BP3 cell line (which express high levels of Bfl-1 and Mcl-1) in a one day Annexin-V apoptosis assay was evaluated. For this assay, Annexin V-FITC and propidium iodide (PI) double staining was used, followed by flow-cytometry analysis. The pan-Bcl-2 family inhibitor 6f effectively induced apoptosis of the RS4;11 and BP3 cell lines in a dose-dependent manner with EC$_{50}$ values of 3.5 and 3.0 µM, respectively, which are 2-3 times more potent than 6a (EC$_{50}$ values of 7.4 and 9.2 µM, respectively) in same assays. By comparison, the potent Bcl-$X_L$ and Bcl-2 antagonist ABT-737 displayed no cytotoxic activity against BP3 cell lines presumably because ABT737 is not effective against Mcl-1 and Bfl-1. Consistent with previous results obtained for human PC3, H460 and H1299 cancer cell lines, most of synthesized 6a derivatives induced apoptosis of the RS4;11 and BP3 cell lines in a dose-dependent manner.

To further explore the anticancer activities of selected 5,5' substituted 6a derivatives, their ability to induce apoptosis of primary lymphocytic leukemia cells freshly isolated from different patients affected by chronic lymphocytic leukemia (CLL) in a one day Annexin-V apoptosis assay was tested. Consistent with previous results obtained for human RS4;11 and BP3 cell lines, the most potent compound 6f effectively induced apoptosis of two primary CLL samples in a dose-dependent manner with $LD_{50}$ values of 10 µM and 15 µM, respectively. By comparison, compound 6a display weak activities in these two primary cells ($LD_{50}$>30 µM). Compound 6f was further tested against primary leukemic cells freshly isolated from different six patients affected by CLL using the same assay. In agreement with previous CLL results, compound 6f effectively induced apoptosis of all six CLL samples with $LD_{50}$ values ranging from 1.0-16.9 µM. Compound 6c also effectively induced apoptosis of primary CLL samples, with a $LD_{50}$ value of 6.5 µM while 6a is less effective ($LD_{50}$>30 µM).

To test the pharmacological properties of 5,5' substituted compound 6a derivatives, their in vitro plasma stability, microsomal stability, and cell membrane permeability were determined. Table 4 provides the plasma stability, microsomal stability and membrane permeability of selected 5,5' substituted 6a derivatives.

TABLE 4

| Compounds | Plasma Stability (T = 40 mins) | Microsomal Stability (T = 40 mins) | Membrane Permeability (PAMPA, LogPe) |
|---|---|---|---|
| 6a | 77% | 47% | −5.94 ± 0.09 |
| 8a | 91% | 71% | −7.88 ± 0.08 |
| 6b | 98% | 69% | −6.17 ± 0.02 |
| 6d | 74% | 98% | −5.82 ± 0.20 |
| 6e | 81% | 89% | −6.58 ± 0.05 |
| 6f | 86% | 63% | −5.59 ± 0.08 |
| 6g | 87% | 88% | −6.65 ± 0.05 |
| 6i | 95% | 91% | −7.11 ± 0.04 |

From these studies, it was concluded that most of the synthesized compounds displayed superior plasma and microsomal stability compared to 6a. Compounds 6f and 6i degraded 37% and 9%, respectively, after 1 h incubation in rat plasma while 6a degraded 53% under the same conditions. In addition, compounds 6f and 6i also displayed better plasma stability and only degraded by 14% and 5%, respectively, after 1 h incubation in rat plasma preparations while 6a degraded 23% under the same conditions.

Based on a combination of 1D $^1$H-NMR binding assays, FP assays, ITC, cytotoxicity assays and preliminary in vitro ADME data, compounds were selected for in vivo studies using a B6-Bcl-2 transgenic mouse model. B-cells of the B6 transgenic mice overexpress human Bcl-2 and accumulate in the spleen of mice. The spleen weight is used as an end-point for assessing in vivo activity as it was determined that the spleen weight is highly consistent in age- and sex-matched Bcl-2-transgenic mice, varying by only ±2% among control Bcl2 mice. The in vivo activities of compounds such as 6b and 6f side by side with 6a in a single Bcl-2 transgenic mouse with a single intraperitoneal (ip) injection at 60 and 120 µmol/kg, respectively, were screened. In agreement with all in vitro data, tested 5,5' substituted 6a derivatives induce significant spleen weight reduction of mice in a dose-dependent manner. Compounds 6b, 6d and 6f displayed superior in vivo activity compared to 6a at dose of 60 µmol/kg. In particular, compounds 6b and 6f induced more than 30-40% spleen weight reduction compared to the 20% induced by 6a. Since the maximum spleen shrinkage would be no more than 50% in this experimental model,[19] these compounds induced near maximal (60-80%) biological activity, while 6a induced only 40% of maximum reduction in spleen weight at the same dose. Mice treated with 6b, 6d and 6f tolerated treatment well with no observed toxicity. However, mice treated with compounds 6i, 6l and 8a at 60 µmol/kg i.p., died. Nevertheless, compounds 6i and 6l are well tolerated when adimistested i.p. at 30 µmol/kg resulting in significant maximal reduction of speen size of 86%±8.0% and 76%±14.0%, respectively.

To further confirm results of the single transgenic mouse experiment, the in vivo activity of compound 6f in groups of seven B6-Bcl-2 transgenic mice each at a dose of 60 µmol/kg was evaluated. Consistent with the single mouse experiment, compound 6f treatment resulted in a significant (~60%) reduction of spleen weight (P<0.0002) compared to the control group of seven mice. All mice tolerated the treatment well, with no evident signs of toxicity. The average weight loss of mice was ~5.0% during the course of this study with compound 6f.

To examine the therapeutic potential of compound 6a and its derivatives (6f and 6i) as a single agent against prostate cancer, the in vivo efficacy of these compounds were investigated side by side with compound 1 on the growth of PPC-1 xenograft tumors. When dosed i.p. three times in first week at 50 mg/kg, compound 6f and 6a induced strong tumor regression compared with the control group. Mice treated with 6f and 6a tolerate the treatment well in first week with modest (~5%) weight loss. However, mice treated with 6i (50 mg/kg, i.p.) and 1 (25 mg/kg, i.p.) died in the first week of this experiment. Mice were treated with 6f and 6a twice in the second week and once in third week at 50 mg/kg. Overall, compound 6f displayed significant antitumor activity compared to control group, with T/C % ratios of 33% (P<0.001) in PPC-1 xenograft-bearing nude mice. Compound 6a showed weaker antitumor activity compared to 6f, with T/C % ratios of 65% in same xenograft model. Mice treated with 6f tolerated the treatment were well with no observable signs of toxicity. Average body weight losses during the treatment are 6.8%, 7.1% and 9.3% for 6f, control and 6a group, respectively.

A series of 5,5' substituted 6a derivatives were synthesized and evaluated in a variety of in vitro and in vivo assays. Compound 6f was found to bind to Bcl-$X_L$, Bcl-2 and Mcl-1 with $IC_{50}$ values of 3.10 µM, 3.12 µM and 2.05 µM, respectively. In a cellular assay, 6f potently inhibited growth in cultures of the PC3, H460, H1299 and BP3 cancer cell lines, which express Bcl-$X_L$, Bcl-2, Mcl-1 and Bfl-1, respectively, with $EC_{50}$ values in the single digit micromolar to nanomolar range. Compound 6f effectively induced apoptosis of the RS4;11 human lymphoma cell line and primary human chronic lymphocytic leukemia cells in a dose-dependent manner. Compound 6f also displays in vivo efficacy in transgenic mice in which Bcl-2 is overexpressed in splenic B-cells. Finally, compound 6f showed favorable in vitro ADME properties and superior in vivo efficacy as a single agent in a PPC-1 nude mouse xenograft model relative to 6a. Considering the critical roles of anti-apoptotic Bcl-2 family proteins in tumorgenesis, chemoresistance, and the potent inhibitory activity of 6f against anti-apoptotic Bcl-2 family proteins, compound 6f represents a viable compound for the development of novel apoptosis-based cancer therapies.

According to other embodiments, the disclosure provides a method for treating a disease or disorder. The method can include administering to a subject in need of such treatment, an effective amount of any herein described compound, or pharmaceutically acceptable salts, hydrates, or solvates thereof. Non-limiting examples of the diseases or disorders that may be treated are cancer and autoimmune diseases.

According to another embodiment, the disclosure provides a method for treating cancer. The method comprises administering to a subject in need thereof a therapeutically effective amount of any above herein described compound, or pharmaceutically acceptable salts, hydrates, or solvates thereof. Any herein described compound may be used for treating any type of cancer. In some aspects, the kinds of cancer that may be treated include lung cancer, breast cancer, prostate cancer, as well as a variety of lymphomas.

According to another embodiment, any of the disclosed compound may be used for the manufacture of a medicament for the treatment of a pathological condition or symptom in a mammal, such as a human. The medicament may be directed to the treatment of cancer, within the limitations described herein.

According to another embodiment, the disclosure provides pharmaceutical compositions. The pharmaceutical compositions may comprise any of the disclosed compounds, or pharmaceutically acceptable salts, hydrates, or solvates thereof, and a pharmaceutically acceptable diluent or carrier. The pharmaceutical compositions may be used to treat cancer. The pharmaceutical compositions can further optionally include one or more additional therapeutic anti-cancer agents, including, but not limited to, such agents as (1) alkaloids, including, microtubule inhibitors (e.g., Vincristine, Vinblastine, and Vindesine, etc.), microtubule stabilizers (e.g., Paclitaxel [marketed under the trademark "TAXOL®"], and Docetaxel [marketed under the trademark "TAXOTERE®"], etc.), and chromatin function inhibitors, including, topoisomerase inhibitors, such as, epipodophyllotoxins (e.g., Etoposide [VP-16], and Teniposide [VM-26], etc.), and agents that target topoisomerase I (e.g., Camptothecin and Isirinotecan [CPT-11], etc.); (2) covalent DNA-binding agents [alkylating agents], including, nitrogen mustards (e.g., Mechlorethamine, Chlorambucil, Cyclophosphamide, Ifosphamide, and Busulfan [marketed under the trademark "MYLERAN®"], etc.), nitrosoureas (e.g., Carmustine, Lomustine, and Semustine, etc.), and other alkylating agents (e.g., Dacarbazine, Hydroxymethylmelamine, Thiotepa, and Mitocycin, etc.); (3) noncovalent DNA-binding agents [anti-tumor antibiotics], including, nucleic acid inhibitors (e.g., Dactinomycin [Actinomycin D], etc.), anthracyclines (e.g., Daunorubicin [Daunomycin, marketed under the trademark "CERUBIDINE®"], Doxorubicin [marketed under the trademark "ADRIAMYCIN®"], and Idarubicin [marketed under the trademark "IDAMYCIN®"], etc.), anthracenediones (e.g., anthracycline analogues, such as, [Mitoxantrone], etc.), bleomycins (marketed under the trademark "BLENOXANE®"), etc., and plicamycin (Mithramycin), etc.; (4) antimetabolites, including, antifolates (e.g., Methotrexate, marketed under the trademarks "FOLEX®", and "MEXATE®", etc.), purine antimetabolites (e.g., 6-Mercaptopurine[6-MP, marketed under the trademark "PURINETHOL®"], 6-Thioguanine[6-TG], Azathioprine, Acyclovir, Ganciclovir, Chlorodeoxyadenosine, 2-Chlorodeoxyadenosine [CdA], and 2'-Deoxycoformycin [Pentostatin], etc.), pyrimidine antagonists (e.g., fluoropyrimidines [e.g., 5-fluorouracil (marketed under the trademark "ADRUCIL®"), 5-fluorodeoxyuridine (FdUrd) (Floxuridine)] etc.), and cytosine arabinosides (marketed under the trademark "CYTOSAR®" [ara-C] and Fludarabine, etc.); (5) enzymes, including, L-asparaginase, and hydroxyurea, etc.; (6) hormones, including, glucocorticoids, such as, antiestrogens (e.g., Tamoxifen, etc.), nonsteroidal antiandrogens (e.g., Flutamide, etc.), and aromatase inhibitors (e.g., anastrozole [marketed under the trademark "ARIMIDEX®"], etc.); (7) platinum compounds (e.g., Cisplatin and Carboplatin, etc.); (8) monoclonal antibodies conjugated with anticancer drugs, toxins, and/or radionuclides, etc.; (9) biological response modifiers (e.g., interferons [e.g., IFN-.alpha., etc.] and interleukins [e.g., IL-2, etc.], etc.); (10) adoptive immunotherapy; (11) hematopoietic growth factors; (12) agents that induce tumor cell differentiation (e.g., all-trans-retinoic acid, etc.); (13) gene therapy agents; 14) antisense therapy agents; (15) tumor vaccines; (16) agents directed against tumor metastases (e.g., Batimistat, etc.); (17) inhibitors of angiogenesis, and (18) selective serotonin reuptake inhibitors (SSRI's).

Relative, but non-limiting examples of suitable SSRIs that may be used include sertraline (e.g., sertraline hydrochloride, marketed under the trademark "ZOLOFT®" by Pfizer, Inc.) or sertraline metabolite, fluvoxamine (e.g., fluvoxamine melate, marketed under the trademark "LUVOX®" by Solvay Pharmaceuticals, Inc.), paroxetine (e.g., paroxetine hydrochloride, marketed under the trademark "PAXIL®" by SmithKline Beecham Pharmaceuticals, Inc.), fluoxetine (e.g., fluoxetine hydrochloride, marketed under the trademarks "PROZAC®" or "SARAFEM®" by Eli Lilly and Company) and citalopram (e.g., citalopram hydrobromide, marketed under the trademark "CELEXA®" by Forest Laboratories, Parke-Davis, Inc.), and metabolites thereof. Additional examples include venlafaxine (e.g., venlafaxine hydrochloride marketed under the trademark "EFFEXOR®" by Wyeth-Ayerst Laboratories), mirtazapine (e.g., marketed under the trademark "REMERON®" by Organon, Inc.), buspirone (e.g., buspirone hydrochloride marketed under the trademark "BUSPAR®" by Bristol-Myers Squibb), trazodone (e.g., trazodone hydrochloride marketed under the trademark "DESYREL®" by Bristol-Myers Squibb and Apothecon), nefazadone (e.g., nefazodone hydrochloride marketed under the trademark "SERZON®" by Bristol-Myers Squibb), clomipramine (e.g., clomipramine hydrochloride marketed under the trademark "ANAFRANIL®" by Novopharm, LTD, Ciba, and Taro Pharmaceuticals), imipramine (e.g., imipramine hydrochloride marketed under the trademark "TOFRANIL®" by Glaxo-Welcome, Inc.), nortriptyline (e.g., Nortriptyline hydrochloride marketed under the trademark "NORTRINEL®" by Lundbeck), mianserine (e.g., marketed under the trademark "TOLVON®" by Organon, Inc.), duloxetine (e.g., duloxetine hydrochloride marketed by Eli Lilly and Company), dapoxetine (e.g., dapoxetine hydrochloride marketed by ALZA Corporation), litoxetine (e.g., litoxetine hydrochloride marketed by Synthelabo Recherche (L.E.R.S.), Bagneux, France.), femoxetine, lofepramine (e.g., marketed under the trademark "GAMONIL®" by MERCK & Co., Inc.), tomoxetine (e.g., marketed by Eli Lilly and Company). The disclosure encompasses SSRIs that are currently used, or those later discovered or formulated. SSRIs, including those listed herein, may be administered orally in an amount between about 2 mg and about 2,500 mg daily.

In the broad sense, any cancer or tumor (e.g. hematologic and solid tumors) may be treated according to embodiments of the disclosure. Exemplary cancers that may be treated according to embodiments of the disclosure include, but are not limited to, head and neck cancer, brain cancer (e.g. glioblastoma multifoma) breast cancer, colorectal cancer, esophageal cancer, gastric cancer, hepatic cancer, bladder cancer, cervical cancer, endometrial cancer, lung cancer (non-small cell), ovarian cancer and other gynological cancers (e.g. tumors of the uterus and cervix), pancreatic cancer, prostate cancer, renal cancer, choriocarcinoma (lung cancer), skin cancer (e.g. melanoma, basal cell carcinoma), hairy cell leukemia, chronic lymphotic leukemia, acute lymphocytic leukemia (breast & bladder), acute myelogenous leukemia, meningeal leukemia, chronic myelogenous leukemia, and erythroleukemia. More commonly, the cancers treated include leukemia and B-cell cancers (e.g. lymphoma, multiple myeloma, and MDS.

Non-limiting examples of autoimmune diseases that may be treated using any herein described compound and methods of the disclosure include rheumatoid arthritis, psoriatic arthritis, juvenile idiopathic arthritis, multiple sclerosis, systemic lupus erythematosus, myasthenia gravis, juvenile onset diabetes, glomerulonephritis, autoimmune thyroiditis, Behcet's disease, Crohn's disease, ulcerative colitis, bullous pemphigoid, sarcoidosis, psoriasis, ichthyosis, Graves ophthalmopathy, psoriasis, psoriasis inflammatory bowel disease, and asthma.

As discussed in more detail herein, some embodiments also provide methods for treating and/or prevention various inflammatory disorders, diseases and conditions. Such inflammatory disorders, diseases and conditions include, without limitation, systemic autoimmune diseases such as, for example, lupus erythematosus, rheumatoid arthritis, multiple sclerosis, and psoriasis; and organ specific autoimmune diseases such as, for example, ulcerative colitis, myasthenia gravis, Grave's disease, Hashimoto's thyroiditis, Crohn's disease, lupus nephritis, autoimmune hemolytic anemias, immune thrombocytopenic purpura (ITP), thrombotic thrombocytopenic purpura (TTP), insulin dependent diabetes mellitus, glomerulonephritis, and rheumatic fever. Other inflammatory diseases that may be treated in accordance with this disclosure include, without limitation, other inflammatory arthritic conditions such as psoriatic arthritis, osteoarthritis and gouty arthritis, as well as other inflammatory conditions such as conjunctivitis, dermatitis, bronchitis, rhinitis etc., brought about by injury, allergies, infections, microorganisms, trauma, or physical or chemical agents. The treatment of inflammatory aspects of asthma, Sjogrens' syndrome, meningitis, adrenoleukodystrophy, CNS vasculitis, mitochondrial myopathies, Amyotrophic Lateral Sclerosis, Alzheimer's disease, or tumors is also contemplated as part of this disclosure. Examples of mitochondrial myopathies include MELAS syndrome, MERF syndrome, Leber's disease, Wernicke's encephalopathy, Rett syndrome, homocystinuria, hyperprolinemia, nonketotic hyperglycinemia, hydroxybutyric aminoaciduria, sulfite oxidase deficiency, and combined systems disease (B12 deficiency). In association with such prevention and/or treatment, articles of manufacture, compositions, methods of use, and medical treatments by disclosed compounds are also provided.

In some cases, it may be appropriate to administer any herein described compound as a salt. Examples of pharmaceutically acceptable salts include organic acid addition salts formed with acids which form a physiological acceptable anion, for example, tosylate, methanesulfonate, acetate, citrate, malonate, tartarate, succinate, benzoate, ascorbate, ketoglutarate, and glycerophosphate. Suitable inorganic salts may also be formed, including hydrochloride, sulfate, nitrate, bicarbonate, and carbonate salts. Pharmaceutically acceptable salts may be obtained using standard procedures well known in the art, for example by reacting any herein described compound with a suitable base affording a physiologically acceptable anion. Alkali metal (for example, sodium, potassium or lithium) or alkaline earth metal (for example calcium) salts of carboxylic acids can also be made.

Any tablets, troches, pills, capsules, and the like, which incorporate any herein described compound, may also contain binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When there is a unit dosage form of any herein described compound, it may contain, in addition to materials of the herein type, a liquid carrier, such as a vegetable oil or a polyethylene glycol. Various other materials may be as coatings or to otherwise modify the physical form of a solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Any material used in preparing any unit dosage form should be pharmaceutically acceptable and substantially non-toxic in the amounts employed. In addition, any herein described compound may be incorporated into sustained-release preparations and devices.

Any herein described compound may also be administered intravenously or intraperitoneally by infusion or injection. Solutions of any herein described compound may be prepared in water, optionally mixed with a nontoxic surfactant. Dispersions may also be prepared in glycerol, liquid polyethylene glycols, triacetin, and mixtures thereof and in oils. Under ordinary conditions of storage and use, these preparations may contain a preservative to prevent the growth of microorganisms.

Sterile injectable solutions may be prepared by incorporating any herein described compound of in the sufficient therapeutic amount in the appropriate solvent with various of the other ingredients enumerated herein, as required, followed by filter sterilization. In the case of sterile powders for the preparation of sterile injectable solutions, the methods of preparation are vacuum drying and the freeze drying techniques, which yield a powder of the active ingredient plus any additional desired ingredient in the previously sterile-filtered solutions.

For topical administration, any herein described compound may be applied in pure form, i.e., when it is a liquid. However, it will generally be desirable to administer it to the skin as compositions or formulations, in combination with a dermatologically acceptable carrier, which may be a solid or a liquid. Useful solid carriers include finely divided solids such as talc, clay, microcrystalline cellulose, silica, alumina and the like. Useful liquid carriers include water, alcohols or glycols or water-alcohol/glycol blends, in which the compounds may be dissolved or dispersed at effective levels, optionally with the aid of non-toxic surfactants. Adjuvants and additional antimicrobial agents may be added to optimize the properties for a given use.

The resultant liquid compositions may be applied from absorbent pads, used to impregnate bandages and other dressings, or sprayed onto the affected area using pump-type or aerosol sprayers. Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user, as known to those having ordinary skill in the art.

The disclosure also provides a pharmaceutical composition comprising disclosed compounds, or a pharmaceutically acceptable salt thereof, in combination with a pharmaceutically acceptable diluent or carrier. Further, the disclosure provides the use of compounds disclosed herein in combination with other known anti-inflammatory compounds.

In various embodiments, the disclosure provides a method for treating inflammatory disease and/or a condition associated with inflammation comprising administering to a mammal in need of such therapy, an effective amount of a disclosed compound, in combination with an additional anti-inflammatory compound or a pharmaceutically acceptable salt thereof. In other embodiments, methods for the prevention of inflammatory disease and/or a condition associated with inflammation or a method for reducing the likelihood that a patient will develop such inflammation is provided. The methods can include administering to a mammal in need of such therapy, an effective amount of a disclosed compound or a pharmaceutically acceptable salt thereof.

There are also provided methods for treating a mammalian subject, particularly a human, suspected of having, or being prone to a disease or condition involving inflammation, comprising administering to a mammalian subject in need thereof a therapeutically effective amount of a compound comprising at least one of disclosed compounds of Formula I may be a single enantiomer, a mixture of the (+) enantiomer and the (−) enantiomer, a mixture of about 90% or more by weight of the (+) or (−) enantiomer and about 10% or less by weight of the (−) or (+) enantiomer, respectively, or a pharmaceutically acceptable salt, solvate, or prodrug thereof, so as to affect treat or prevent inflammation.

In some embodiments, the methods for treating inflammation or preventing inflammation include administration of an effective amount of another therapeutic agent useful for treating or preventing the diseases or disorders disclosed herein. In some embodiments, the time in which the therapeutic effect of the other therapeutic agent is exerted overlaps with the time in which the therapeutic effect of the Apogossypol or derivative is exerted.

In some embodiments, the other therapeutic agent is an anti-inflammatory agent. Examples of anti-inflammatory agents suitable for use according to some embodiments disclosed herein include, but are not limited to, steroids (e.g., cortisol, cortisone, fludrocortisone, prednisone, methylprednisolone, 6-methylprednisone, triamcinolone, betamethasone or dexamethasone), nonsteroidal anti-inflammatory drugs (NSAIDS (e.g., aspirin, acetaminophen, tolmetin, salicylates, ibuprofen, mefenamic acid, piroxicam, nabumetone, rofecoxib, celecoxib, etodolac or nimesulide). For the treatment of lupus erythmatosus, for example, the compounds disclosed herein may also be administered in conjunction with anti-malarial drugs including, for example, hydroxychloroquinone or in conjunction with cytotoxic chemotherapies including, for example, azathioprine and cyclophosphamide.

In some embodiments, the other therapeutic agent is an antibiotic (e.g., vancomycin, penicillin, amoxicillin, ampicillin, cefotaxime, ceftriaxone, cefixime, rifampinmetronidazole, doxycycline or streptomycin). In another embodiment, the other therapeutic agent is a PDE4 inhibitor (e.g., roflumilast or rolipram). In another embodiment, the other therapeutic agent is an antihistamine (e.g., cyclizine, hydroxyzine, promethazine or diphenhydramine). In another embodiment, the other therapeutic agent is an anti-malarial (e.g., artemisinin, artemether, artsunate, chloroquine phosphate, mefloquine hydrochloride, doxycycline hyclate, proguanil hydrochloride, atovaquone or halofantrine).

Another type of therapeutic agent useful in the combination treatment of the disclosure is an antibody such as a humanized monoclonal antibody. Non-limiting examples include, the anti-CD99 antibody. See, for example, U.S. Pat. No. 7,223,395; White et al., Annu. Rev. Med., 52:125 (2001). Rituximab (marketed under the trademark "RITUXAN®"; Genentech, South San Francisco, Calif.) is another therapeutic agent that is useful in a conjugate of the disclosure for treating rheumatoid arthritis. Another therapeutic agent useful in the disclosure also may be cytotoxic agents, which, as used herein, is any molecule that directly or indirectly promotes cell death. Specific anticancer agents include Flavopiridol, doxorubicin marketed under the trademark "ADRIAMYCIN®", VP16 (Etoposide), paclitaxel marketed under the trademark "TAXOL®", cisplatin and the like.

In cases where compounds are sufficiently basic or acidic to form stable nontoxic acid or base salts, administration of the compounds as salts may be appropriate. Examples of pharmaceutically acceptable salts are organic acid addition salts formed with acids which form a physiological acceptable anion, for example, tosylate, methanesulfonate, acetate, citrate, malonate, tartarate, succinate, benzoate, ascorbate, a-ketoglutarate, and a.-glycerophosphate. Suitable inorganic salts may also be formed, including hydrochloride, sulfate, nitrate, bicarbonate, and carbonate salts.

Pharmaceutically acceptable salts may be obtained using standard procedures well known in the art, for example by reacting a sufficiently basic compound such as an amine with a suitable acid affording a physiologically acceptable anion. Alkali metal (for example, sodium, potassium or lithium) or alkaline earth metal (for example calcium) salts of carboxylic acids can also be made.

The compounds useful in practicing the disclosure may be formulated as pharmaceutical compositions and administered to a mammalian host, such as a human patient in a variety of forms adapted to the chosen route of administration, i.e., orally or parenterally, by intravenous, intramuscular, topical or subcutaneous routes.

The compounds may be systemically administered, e.g., orally, in combination with a pharmaceutically acceptable vehicle such as an inert diluent or an assimilable edible carrier. The route of administration may be oral or intravenous. Other routes of administration include, for example, parental, intramuscular, topical and subcutaneous. The compounds may be enclosed in hard or soft shell gelatin capsules, may be compressed into tablets, or may be incorporated directly with the food of the patient's diet. For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of a given unit dosage form. The amount of active compound in such therapeutically useful compositions is such that an effective dosage level will be obtained.

The compounds of Formula I may be administered in a variety of ways. For example, the tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the herein type, a liquid carrier, such as a vegetable oil or a polyethylene glycol. Various other materials may be as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Any material used in preparing any unit dosage form should be pharmaceutically acceptable and substantially non-toxic in the amounts employed. In addition, the active compound may be incorporated into sustained-release preparations and devices.

The compounds may also be administered intravenously or intraperitoneally by infusion or injection. Solutions of the active compound or its salts may be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle may be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity may be maintained, for example, by the formation of liposomes, by the maintenance of the required particle size in the case of dispersions or by the use of surfactants. The prevention of the action of microorganisms may be brought about by various antibacterial and antifungal agents, for example, parabens, chlorobutanol, phenol, sorbic acid, thimerosal, and the like. In many cases, it will be advisable to include isotonic agents, for example, sugars, buffers or sodium chloride. Prolonged absorption of the injectable compositions may be brought about by the use in the compositions of agents delaying absorption, for example, aluminum monostearate and gelatin.

Sterile injectable solutions are prepared by incorporating the active compound in the required amount in the appropriate solvent with various of the other ingredients enumerated herein, as required, followed by filter sterilization. In the case of sterile powders for the preparation of sterile injectable solutions, the methods of preparation are vacuum drying and the freeze drying techniques, which yield a powder of the active ingredient plus any additional desired ingredient in the previously sterile-filtered solutions.

For topical administration, the compounds may be applied in pure form, i.e., when they are liquids. However, it will generally be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina and the like. Useful liquid carriers include water, alcohols or glycols or water-alcohol/glycol blends, in which the compounds may be dissolved or dispersed at effective levels, optionally with the aid of non-toxic surfactants. Adjuvants such as fragrances and additional antimicrobial agents may be added to optimize the properties for a given use. The resultant liquid compositions may be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Examples of useful dermatological compositions which may be used to deliver the compounds of structures A or B to the skin are known in the art; for example, see U.S. Pat. Nos. 4,608,392, 4,992,478, 4,559,157, and 4,820,508.

Useful dosages of the compounds may be determined by comparing their in vitro activity, and in vivo activity in animal models. Methods for the extrapolation of effective dosages in mice, and other animals, to humans are known to the art; for example, see U.S. Pat. No. 4,938,949.

Generally, the concentration of the compounds of Formula I in a liquid composition, such as a lotion, may be between about 0.1 and about 25.0 mass %, such as between about 0.5 about 10.0 mass %. The concentration in a semi-solid or solid composition such as a gel or a powder may be between about 0.1 and about 5.0 mass %, such as between about 0.5 and 2.5 mass %.

The amount of the compound, or an active salt or derivative thereof, required for use in treatment will vary not only with the particular salt selected but also with the route of administration, the nature of the condition being treated and the age and condition of the patient and will be ultimately at the discretion of the attendant physician or clinician. In general, however, a suitable dose may be in the range of between about 0.2 and about 100.0 μmmol/kg per day. In one embodiment, the dose may be, e.g., between about 0.2 to about 1.0 μmmol/kg per day. In some embodiments, a suitable does may be in the rage of between about 0.5 and about 100 mg/kg, e.g., between about 10 and about 75 mg/kg of body weight per day, such as between about 3 and about 50 mg per kilogram body weight of the recipient per day, for example, in the range of between about 6 and about 90 mg/kg/day, such as in the range of between about 15 and about 60 mg/kg/day.

Pharmaceutical compositions suitable for use in the methods disclosed herein include compositions where the active ingredients are contained in an amount effective to achieve its intended purpose. More specifically, a therapeutically effective amount means an amount of compound effective to prevent, alleviate or ameliorate symptoms of disease or prolong the survival of the subject being treated. Determination of a therapeutically effective amount is well within the capability of those skilled in the art, especially in light of the detailed disclosure provided herein.

The exact formulation, route of administration and dosage for the pharmaceutical compositions disclosed herein may be chosen by the individual physician in view of the patient's condition. Typically, the dose range of the composition administered to the patient may be between about 0.5 and about 1000 mg/kg of the patient's body weight, or between about 1 and about 500 mg/kg, or between about 10 and about 500 mg/kg, or between about 50 and about 100 mg/kg of the patient's body weight. The dosage may be a single one or a series of two or more given in the course of one or more days, as is needed by the patient. Where no human dosage is established, a suitable human dosage may be inferred from $ED_{50}$ or ID$_{50}$ values, or other appropriate values derived from in vitro or in vivo studies, as qualified by toxicity studies and efficacy studies in animals.

Although the exact dosage will be determined on a drug-by-drug basis, in most cases, some generalizations regarding the dosage may be made. The daily dosage regimen for an adult human patient may be, for example, an oral dose of between about 0.1 mg and about 500 mg of each ingredient, such as between about 1 mg and about 250 mg, e.g. between about 5 and about 200 mg or an intravenous, subcutaneous, or intramuscular dose of each ingredient between about 0.01 mg and about 100 mg, such as between about 0.1 mg and about 60 mg, e.g. between about 1 and about 40 mg of each ingredient of the pharmaceutical compositions disclosed herein or a pharmaceutically acceptable salt thereof calculated as the free base, the composition being administered 1 to 4 times per day. Alternatively the compositions disclosed herein may be administered by continuous intravenous infusion, which may be at a dose of each ingredient up to 400 mg per day. Thus, the total daily dosage by oral administration of each ingredient will typically be in the range between about 1 and about 2000 mg and the total daily dosage by parenteral administration will typically be in the range between about 0.1 and about 400 mg. In some embodiments, the compounds will be administered for a period of continuous therapy, for example for a week or more, or for months or years.

Dosage amount and interval may be adjusted individually to provide plasma levels of the active moiety, which are sufficient to maintain the modulating effects, or minimal effective concentration (MEC). The MEC will vary for each compound but may be estimated from in vitro data. Dosages necessary to achieve the MEC will depend on individual characteristics and route of administration. However, HPLC assays or bioassays may be used to determine plasma concentrations.

Dosage intervals can also be determined using MEC value. Compositions should be administered using a regimen, which maintains plasma levels above the MEC for 10-90% of the time, such as between 30-90%, e.g., between 50-90%. In cases of local administration or selective uptake, the effective local concentration of the drug may not be related to plasma concentration.

The amount of composition administered will, of course, be dependent on the subject being treated, on the subject's weight, the severity of the affliction, the manner of administration and the judgment of the prescribing physician.

In various embodiments, the compositions may, if desired, be ed in a pack or dispenser device, which may contain one or more unit dosage forms containing the active ingredient. The pack may for example comprise metal or plastic foil, such as a blister pack. The pack or dispenser device may be accompanied by instructions for administration. The pack or dispenser may also be accompanied with a notice associated with the container in form prescribed by a governmental agency regulating the manufacture, use, or sale of pharmaceuticals, which notice is reflective of approval by the agency of the form of the drug for human or veterinary administration. Such notice, for example, may be the labeling approved by the U.S. Food and Drug Administration for prescription drugs, or the approved product insert. Compositions comprising a compound disclosed herein formulated in a compatible pharmaceutical carrier may also be prepared, placed in an appropriate container, and labeled for treatment of an indicated condition.

In various embodiments, compounds of the disclosure may be labeled using methods known in the art. One detectable group is a fluorescent group. Fluorescent groups typically produce a high signal to noise ratio, thereby providing increased resolution and sensitivity in a detection procedure. For example, the fluorescent group absorbs light with a wavelength above about 300 nm, such as above about 350 nm, e.g., above about 400 nm. The wavelength of the light emitted by the fluorescent group is above about 310 nm, such as above about 360 nm, e.g., above about 410 nm.

The fluorescent detectable moiety may be selected from a variety of structural classes, including the following non-limiting examples: 1- and 2-amino-naphthalene, p,p'-diamino-stilbenes, pyrenes, quaternary phenanthridine salts, 9-aminoacridines, p,p'-diaminobenzo-phenone imines, anthracenes, oxacarbocyanine, marocyanine, 3-aminoequilenin, perylene, bisbenzoxazole, bis-p-oxazolyl benzene, 1,2-benzophenazin, retinol, bis-3-aminopridinium salts, hellebrigenin, tetracycline, sterophenol, benzimidazolyl phenylamine, 2-oxo-3-chromen, indole, xanthen, 7-hydroxycoumarin, phenoxazine, salicylate, strophanthidin, porphyrins, triaryl-methanes, flavin, xanthene dyes (e.g., fluorescein and rhodamine dyes); cyanine dyes; 4,4-difluoro-4-bora-3a, 4a-diaza-s-indacene dyes and fluorescent proteins (e.g., green fluorescent protein, phycobiliprotein).

In various embodiments, the compounds may be labeled, where the labeling group spontaneously emits a signal, or generates a signal upon the introduction of a suitable stimulus. Labels, include atoms such as, for example, $^{13}$C, $^{15}$N, $^{19}$F, $^{1}$H and the like. In various embodiments, the compound may be conveniently administered in unit dosage form; for example, containing between about 5 and about 1,000 mg, such as between about 10 and about 750 mg, e.g., between about 50 and about 500 mg of active ingredient per unit dosage form.

In some embodiments, the active ingredient may be administered to achieve peak plasma concentrations of the active compound of between about 0.5 and about 75 μM, such as between about 1 and about 50 μM, e.g., between about 2 and about 30 μM. This may be achieved, for example, by the intravenous injection of a 0.05 to 5% solution of the active ingredient, optionally in saline, or orally administered as a bolus containing about 1-100 mg of the active ingredient. Desirable blood levels may be maintained by, for example, continuous infusion to provide about 0.01-5.0 mg/kg/hr or by intermittent infusions containing about 0.4-15 mg/kg of the active ingredient(s).

The desired dose may conveniently be ed in a single dose or as divided doses administered at appropriate intervals, for example, as two, three, four or more sub-doses per day. The sub-dose itself may be further divided, e.g., into a number of discrete loosely spaced administrations; such as multiple inhalations from an insufflator.

EXAMPLES

Various aspects of the disclosure may be further illustrated by the following non-limiting examples.

Abbreviations list: Bcl-2: B-cell lymphoma/leukemia-2; EDCI: 1-ethyl-3-(3'-dimethylaminopropyl)carbodiimide; 1D-$^{1}$H NMR: one-dimensional $^{1}$H nuclear magnetic resonance spectroscopy; SAR: Structure-activity relationship; FPA: Fluorescence Polarization Assays; ITC: Isothermal Titration calorimetry; CLL: Chronic lymphocytic leukemia; WT: Wild type; MEFs: Mouse embryonic fibroblast cells; DKO: Bax/Bak Double knockout; DKO/MEFs: Bax/Bak Double knockout mouse embryonic fibroblast cells; ACN: Acetonitrile; LC-MS: Liquid chromatography and tandem mass spectrometry; HPLC: High-performance liquid chromatography; TROSY: Transverse Relaxation-Optimized Spectroscopy; ADME: Absorption, Distribution, Metabolism, and Excretion; DMSO: Dimethyl sulphoxide; PPC-1: Human Prostatic cancer cell line; PAMPA: Parallel artificial membrane permeation assay; FITC: Fluorescein isothiocyanate; GST: Glutathione-S-transferase; PBS: Phosphate-buffered saline; SE: Standard error; PI: Propidium iodide; NADPH: Nicotinamide adenine dinucleotide phosphate; Rpm: Rotations Per Minute; and AUC: Area under the curve.

Example 1

General Synthetic Procedures

Unless otherwise noted, all reagents and anhydrous solvents ($CH_2Cl_2$, THF, diethyl ether, etc) were obtained from commercial sources and used without purification. All reactions were performed in oven-dried glassware. All reactions involving air or moisture sensitive reagents were performed under a nitrogen atmosphere. Silica gel or reverse phase chromatography was performed using prepacked silica gel or C-18 cartridges (RediSep), respectively. All final compounds were purified to >95% purity, as determined by a HPLC Breeze from Waters Co. using an Atlantis T3 3 µM 4.6 mm×150 mm reverse phase column.

Method A: The eluant was a linear gradient with a flow rate of 1 mL/min from 50% A and 50% B to 5% A and 95% B in 15 min followed by 5 min at 100% B (Solvent A: $H_2O$ with 0.1% TFA; Solvent B: ACN with 0.1% TFA). Compounds were detected at λ=254 nm.

Method B: The eluant was a linear gradient with a flow rate of 1 mL/min from 20% A and 80% B to 100% B in 15 min followed by 5 min at 100% B (Solvent A: $H_2O$ with 0.1% TFA; Solvent B: ACN with 0.1% TFA). Compounds were detected at λ=254 nm.

$^1$H NMR spectra were recorded on Varian 300 or Bruker 600 MHz instruments. Chemical shifts are reported in ppm (δ) relative to ($Me_4Si$ at 0.00 ppm). Coupling constant[11] are reported in Hz throughout. Mass spectral data were acquired on Shimadzu LCMS-2010EV for low resolution, and on an Agilent ESI-TOF for high resolution.

Example 2

Synthesis of the Compounds of Formula I

The synthesis of 5,5' amide substituted Apogossypolone derivatives of the compounds of Formula I is outlined below:

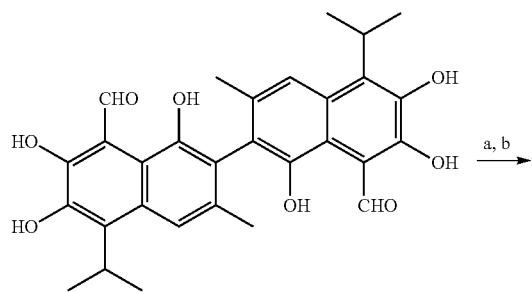

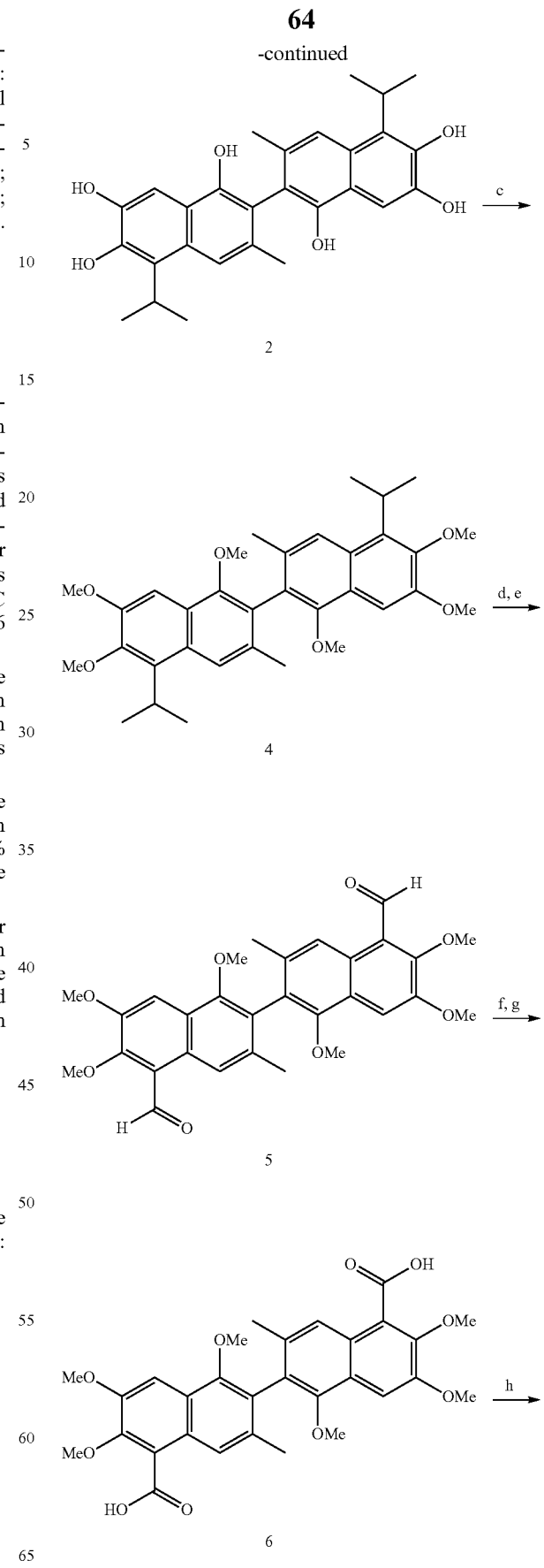

with aqueous HCl provides the amide compound 8. Finally, oxidation of compound 8 with $FeCl_3$ in $H_2SO_4$ provides the desired Apogossypolone derivative 9.

The synthesis of 5,5' alkyl substituted Apogossypol derivatives is outlined below.

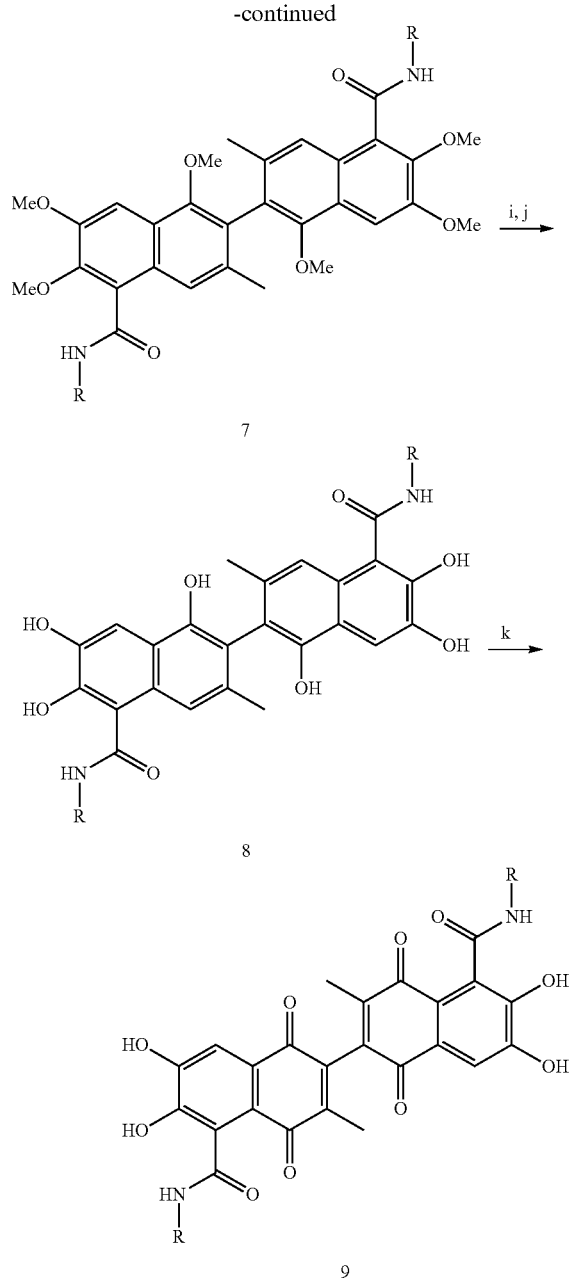

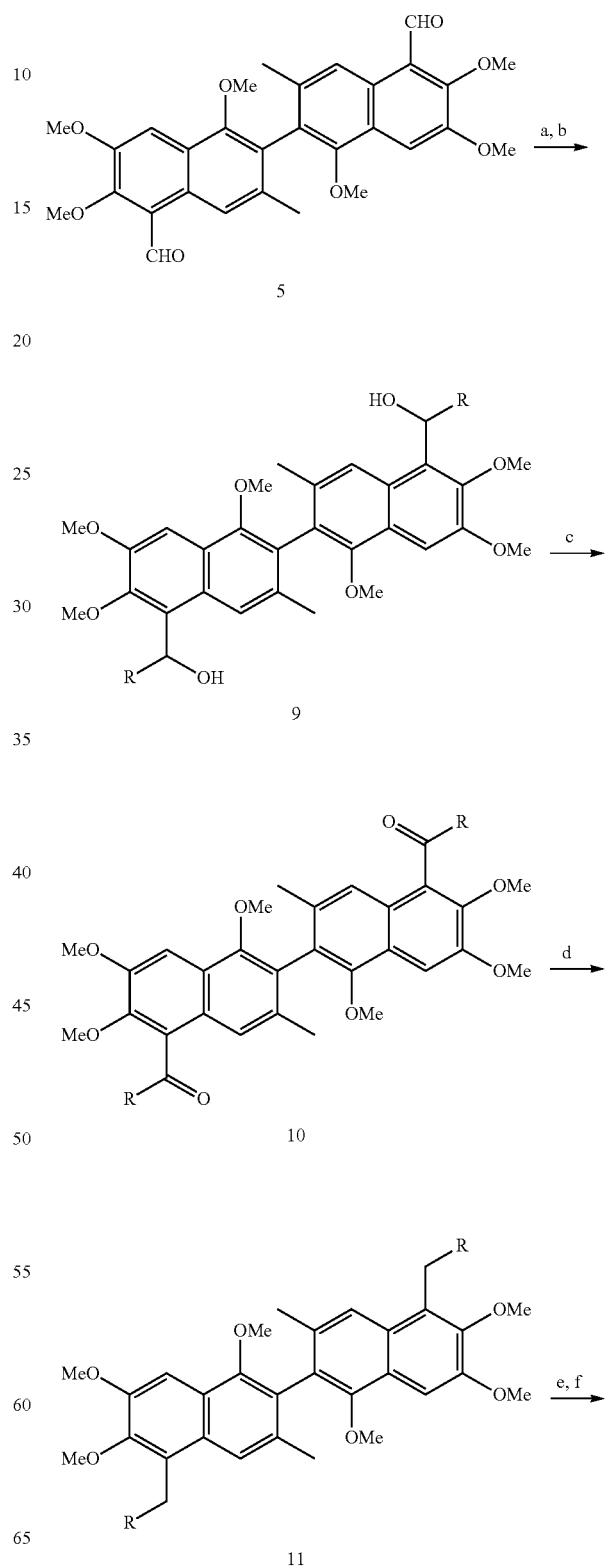

Reagents and conditions: (a) NaOH, $H_2O$, reflux; (b) $H_2SO_4$; (c) DMS, $K_2CO_3$; (d) $TiCl_4$, $Cl_2CHOCH_3$, rt; (e) HCl, $H_2O$ (f) $NaClO_2$, $H_2O_2$, $KH_2PO_4$, $CH_3CN$, rt; (g) HCl, $H_2O$; (h) EDCl, $NH_2R$, HOBT, rt; (i) $BBr_3$, $CH_2Cl_2$ (j) HCl, $H_2O$; (K) $FeCl_3$, $H_2SO_4$.

Gossypol 1 is treated with aqueous NaOH under reflux conditions and the solution is acidified with $H_2SO_4$ to afford compound 2. Methylation of compound 2 occurs upon treatment with DMS and $K_2CO_3$ to provide compound 4. Treatment of compound 4 with $TiCl_4$ and dichloromethyl methyl ether results in the loss of the isopropyl groups and simultaneous bisformylation, which upon acidification with aqueous HCl provides the aldehyde compound 5. Compound 5 is oxidized with $NaClO_2$, $H_2O_2$, $KH_2PO_4$ in acetonitrile and acidified with aqueous HCl to provide the corresponding acid compound 6. Treatment of compound 6 with EDCl, $NH_2R$, HOBT at room temperature affords the amide compound 7. Demethylation of compound 7 occurs upon treatment with $BBr_3$ in dichloromethane and acidification of the solution

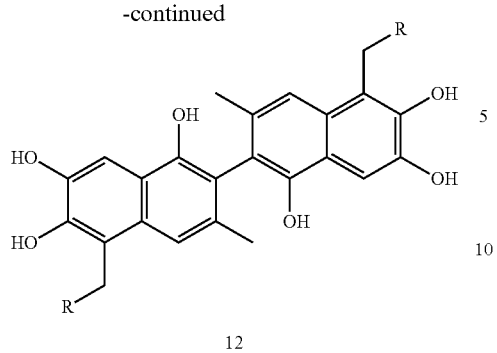

12

Reagents and conditions: (a) RMgBr or RLi, rt; (b) NH$_4$Cl, H$_2$O; (c) Pyridinium chlorochromate, CH$_2$Cl$_2$, rt; (d) Et$_3$SiH, TFA or Pd/C, H$_2$; (e) BBr$_3$; (f) HCl, H$_2$O.

Compound 5 was treated with different Grignard or lithium reagents to afford a secondary alcohol 9, which was oxidized to give the phenone 10 by pyridinium chlorochromate. Triethylsilane reduced phenone 10 to alkyl compound 11 followed by subsequent demethylation using boron tribromide to afford compound 12.

Compounds 13 and 14, with only hydrogen atom or carboxylic acid at 5,5' positions, were synthesized to explore if substitution at 5,5' position is important for enhancing biological activities. Compound 13 was synthesized by treating compound 4 with concentrated sulfuric acid to lose isopropyl group. The resulting product and compound 6 was then treated individually with boron tribromide to give compounds 13 and 14, respectively.

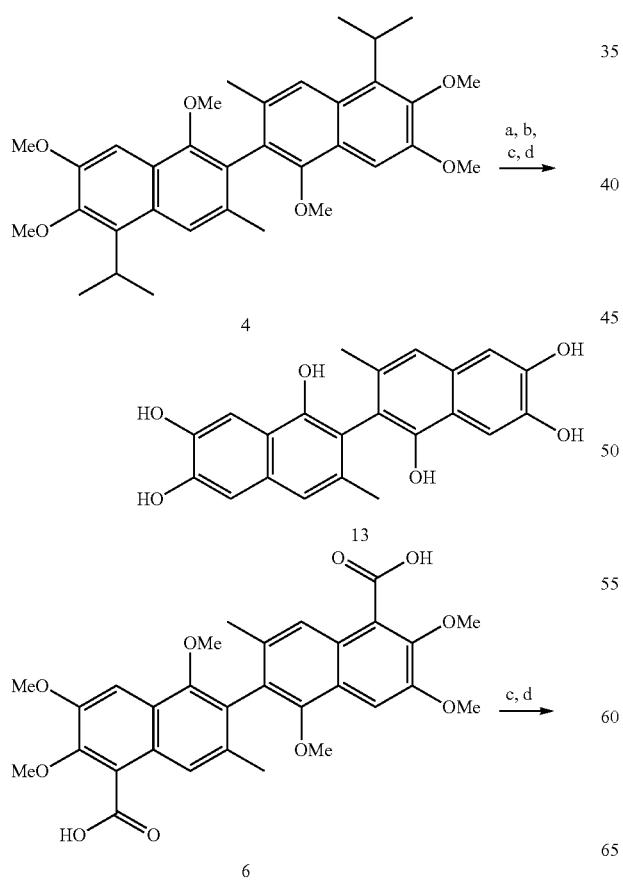

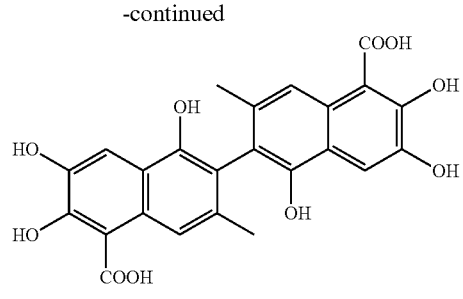

14

Reagents and conditions: (a) H$_2$SO$_4$, rt; (b) H$_2$O; (c) BBr$_3$, CH$_2$Cl$_2$; (d) HCl, H$_2$O.

The synthesis of 5,5' ketone substituted Apogossypolone derivatives of Formula I is outlined below:

Demethylation of ketone compound 11 occurs upon treatment with BBr$_3$ in dichloromethane and acidification of the solution with aqueous HCl provides compound 15. Oxidation of compound 15 with FeCl$_3$ in H$_2$SO$_4$ provides the desired Apogossypolone derivative 16.

Example 3

Detailed Synthesis of the Compounds of Formula I 1,1',6,6',7,7'-Hexahydroxy-5,5'-diisopropyl-3,3'-dimethyl-2,2'-binaphthyl-8,8'-dicarboxaldehyde (1). Compound 1 (Gossypol) is commercially available from Yixin Pharmaceutical Co. HPLC purity 99.0%, $t_R$=12.50 min (Method A).

5,5'-Diisopropyl-1,1',6,6',7,7'-hexamethoxy-3,3'-dimethyl-2,2'-binaphthalene (9)

Compound 1 (5 g, 8.65 mmol) in 50 mL of 40% NaOH was heated under nitrogen at 90° C. for 3.5 h in the dark. The reaction mixture was cooled and poured slowly onto ice (300 mL) and concentrated $H_2SO_4$ (35 mL) mixture to form white precipitation. The precipitation was filtered, washed with water and dried to afford 3.8 g of compound 2a (95%) as a white solid. $^1$H NMR (300 MHz, $CDCl_3$) δ 7.61 (s, 2H), 7.50 (s, 2H), 5.93 (s, 2H), 5.27 (s, 2H), 5.13 (s, 2H), 3.88 (m, 2H), 2.12 (s, 6H), 1.55 (d, J=5.5 Hz, 12H). HPLC purity 99.2%, $t_R$=13.12 min. HRMS calcd for $C_{28}H_{30}O_6$ 463.2115 (M+H). found 463.2108. The compound 2a (3.8 g, 8.21 mmol) was dissolved into acetone (200 mL). $K_2CO_3$ (23.9 g, 206.7 mmol) and dimethyl sulfate (16.3 mL, 206.7 mmol) were added and the reaction mixture was refluxed under nitrogen for 24 h. The solid was collected by filtration and washed using acetone and water and dried to yield 4.2 g of compound 9 as white solid (93%). $^1$H NMR (300 MHz, $CDCl_3$) 7.83 (s, 2H), 7.43 (s, 2H), 3.98 (m, 8H), 3.94 (s, 6H), 3.57 (s, 6H), 2.20 (s, 6H), 1.56 (s, 12H).

5,5'-Diisopropyl-6,6',7,7'-tetramethoxy-3,3'-dimethyl-2,2'-binaphthyl-1,1',4,4'-tetraone (10)

Periodic acid (10 g, 43.8 mmol) was added to a solution of compound 9 (0.62 g, 1.12 mmol) in 20 mL of dioxane and the reaction mixture was stirred at 95° C. for 15 min. Crushed ice was added to quench the reaction. The solution was extracted twice with ethyl acetate and the organic layer was washed with water, brine and dried over $MgSO_4$. The solvent was concentrated in vacuo and the residue was purified by flash silica column chromatography to give 142 mg of compound 10 (23%) as yellow solid. $^1$H NMR (600 MHz, $CD_3OD$) δ 7.56 (s, 2H), 4.31 (m, 2H), 3.97 (s, 6H), 3.94 (s, 6H), 2.03 (s, 6H), 1.40 (d, J=1.8 Hz, 6H), 1.39 (d, J=1.8 Hz, 6H).

6,6',7,7'-tetrahydroxy-5,5'-diisopropyl-3,3'-dimethyl-2,2'-binaphthyl-1,1',4,4'-tetraone (6a)

0.54 mL of $BBr_3$ (1.43 g, 5.71 mmol) was added dropwise into a solution of compound 10 (260 mg, 0.48 mmol) in 10 mL of anhydrous $CH_2Cl_2$ at −78° C. Stirring was continued at −78° C. for 1 h, 0° C. for 1 h, and ambient temperature for 1 h. 50 grams of ice containing 5 mL of 6M HCl was added to the mixture and stirred for 1 h at room temperature. The aqueous layer was extracted with dichloromethane (3×50 mL). The combined organic layer was washed with water, brine and dried over $MgSO_4$. The solvent was concentrated in vacuo and the residue was purified using C-18 column chromatography ($H_2O$/Acetonitrile) followed by recrystallization from ethyl acetate/hexane to give 163 mg of compound 6a (70%) as brown-yellow solid. $^1$H NMR (600 MHz, $CD_3OD$) δ 7.31 (s, 2H), 4.32 (m, 2H), 1.88 (s, 6H), 1.42 (s, 6H), 1.40 (s, 6H). $^{13}$C NMR (600 MHz, $(CD_3)_2SO$)) δ 187.10, 182.51, 150.92, 149.54, 147.60, 137.78, 137.10, 126.24, 125.00, 111.03, 27.07, 20.50, 20.35, 15.00. HPLC purity 99.5%, $t_R$=11.60 min (Method A). HRMS calcd for $C_{28}H_{26}O_8$ 491.1700 (M+H). found 491.1696.

6,6',7,7'-Tetrahydroxy-3,3'-dimethyl-1,1',4,4'-tetraoxo-$N^5,N^{5'}$-bis(2-phenylpropyl)-1,1',4,4'-tetrahydro-2,2'-binaphthyl-5,5'-dicarboxamide (8a)

A solution of compound 4a (290 mg, 0.414 mmol) in 12 mL of acetone and 23 mL of acetic acid was heated on an oil bath (60-67° C.) during the addition of 18 mL of a 10% aqueous solution of ferric chloride (6.64 mmol) and for several minutes longer. The solution was cooled and 30 mL of water was added followed by 20 mL of aqueous 20% sulfuric acid. The solution was extracted twice with diethyl ether and the organic layer was washed with water, brine and dried over $MgSO_4$. The solvent was concentrated in vacuo and the residue was purified by C-18 column chromatography ($H_2O$/Acetonitrile) to give 60 mg of compound 8a (45%) as yellow solid. $^1$H NMR (600 MHz, $CD_3OD$) δ 7.42 (s, 2H), 7.34 (d, J=7.2 Hz, 4H), 7.30 (t, $J_1$=$J_2$=7.2 Hz, 4H), 7.18 (t, $J_j$=$J_2$=7.2 Hz, 4H), 3.54 (d, J=7.2 Hz, 4H), 3.22 (m, 2H), 1.91 (s, 6H), 1.39 (s, 6H), 1.38 (d, J=6.6 Hz, 6H). $^{13}$C NMR (600 MHz, $CD_3OD$) δ 184.50, 183.68, 170.44, 151.92, 150.19, 146.99, 146.55, 140.68, 129.63, 128.54, 127.53, 127.23, 126.13, 124.30, 113.14, 48.34, 40.74, 19.97, 14.50. HPLC purity 98.3%, $t_R$=5.82 min (Method A). HRMS calcd for $C_{42}H_{36}N_2O_{10}$ 729.2443 (M+H). found 729.2441.

Following the above mentioned procedure and the appropriate starting materials and reagents used; compounds 7 and 8b-8c were synthesized.

6,6',7,7'-tetrahydroxy-3,3'-dimethyl-$N^5,N^{5'}$-bis(3-methylbenzyl)-1,1',4,4'-tetraoxo-1,1',4,4'-tetrahydro-2,2'-binaphthyl-5,5'-dicarboxamide (8b)

Yield, 50%; $^1$H NMR (600 MHz, $CD_3OD$) δ 7.44 (s, 2H), 7.39 (s, 2H), 7.29 (d, J=7.2 Hz, 2H), 7.20 (t, $J_1$=7.2 Hz, $J_2$=7.8 Hz, 4H), 7.06 (d, J=7.8 Hz, 2H), 4.61 (dd, $J_1$=15 Hz, $J_2$=4.8 Hz, 4H), 2.35 (s, 6H), 1.91 (s, 6H). $^{13}$C NMR (600 MHz, $CD_3OD$) δ 184.57, 183.70, 170.33, 152.01, 150.28, 147.04, 139.71, 139.24, 129.68, 129.41, 128.87, 127.33, 126.04, 126.00, 124.32, 113.21, 44.65, 21.66, 14.49. HPLC purity 99.0%, $t_R$=5.53 min (Method A). HRMS calcd for $C_{40}H_{32}N_2O_{10}$ 701.2130 (M+H). found 701.2128.

$N^5,N^{5'}$-Bis(4-ethylphenethyl)-6,6',7,7'-tetrahydroxy-3,3'-dimethyl-1,1',4,4'-tetraoxo-1,1',4,4'-tetrahydro-2,2'-binaphthyl-5,5'-dicarboxamide (8c)

Yield, 52%; $^1$H NMR (600 MHz, $CD_3OD$) δ 7.43 (s, 2H), 7.23 (d, J=6.6 Hz, 4H), 7.12 (d, J=6.6 Hz, 4H), 3.60 (m, 4H), 2.96 (t, $J_1$=$J_2$=6.6 Hz, 4H), 2.50 (q, $J_1$=$J_2$=6.6 Hz, 4H), 1.93 (s, 6H), 1.20 (t, $J_1$=$J_2$=6.6 Hz, 6H). $^{13}$C NMR (600 MHz, $CD_3OD$) δ 184.55, 183.68, 170.37, 151.99, 150.18, 147.01, 143.51, 140.73, 138.24, 130.09, 129.09, 127.38, 126.09, 124.31, 113.18, 43.03, 36.03, 29.68, 16.49, 14.51. HPLC purity 97.6%, $t_R$=6.99 min (Method A). HRMS calcd for $C_{44}H_{40}N_2O_{10}$ 757.2756 (M+H). found 757.2745.

6,6',7,7'-Tetrahydroxy-3,3'-dimethyl-5,5'-bis(2-phenylacetyl)-2,2'-binaphthyl-1,1',4,4'-tetraone (7)

Yield, 49%; $^1$H NMR (600 MHz, $CD_3OD$) δ 7.32 (s, 2H), 7.28 (d, J=6.0 Hz, 4H), 7.22 (t, $J_1$=$J_2$=6.0 Hz, 4H), 7.15 (t, $J_1$=$J_2$=6.0 Hz, 2H), 4.13 (m, 4H), 1.93 (s, 6H). $^{13}$C NMR (600 MHz, $CD_3OD$) δ 204.02, 183.63, 181.97, 150.74, 147.30, 145.10, 139.75, 134.05, 130.14, 129.78, 127.70, 126.40, 125.69, 122.90, 111.65, 49.31, 12.84. HPLC purity 99.0%, $t_R$=9.44 min (Method A). HRMS calcd for $C_{38}H_{26}O_{10}$ 643.1599 (M+H). found 643.1601.

1,1',6,6',7,7'-hexamethoxy-3,3'-dimethyl-5,5'-bis(4-methylphenethyl)-2,2'-binaphthyl (15f)

To a freshly prepared 4-methylbenzylmagnesium chloride (30.85 mmol) solution at room temperature was added a solution of 11 (2.0 g, 3.86 mmol) in anhydrous tetrahydrofuran (30 mL) and the reaction mixture was heated at 30° C. for 18 h. The reaction mixture was poured onto saturated ammonium chloride solution and the aqueous layer was extracted twice with diethyl ether, washed with brine and dried over $MgSO_4$. Filtration followed by evaporation of the ether gave yellow oil 13. To a solution of the yellow oil 13 (1.4 g, 1.929 mmol) in 25 mL TFA was added 3.1 mL of triethylsilane dropwise. The solution was heated at 75° C. for 1 h followed by stirred at room temperature for 18 h. The solution was concentrated in vacuo followed by silica gel column chromatography to give 660 mg compound 15f as colorless oil (50% from 11). $^1$H NMR (600 MHz, $CDCl_3$) δ 7.64 (s, 2H), 7.44 (s, 2H), 7.26 (d, J=7.8 Hz, 4H), 7.15 (d, J=7.8 Hz, 4H), 3.99 (s, 6H), 3.94 (s, 6H), 3.60 (s, 6H), 3.37 (t, $J_1$=$J_2$=8.40 Hz, 4H), 2.98 (t, $J_1$=$J_2$=8.4 Hz, 4H), 2.35 (s, 6H), 2.20 (s, 6H).

3,3'-dimethyl-5,5'-bis(4-methylphenethyl)-2,2'-binaphthyl-1,1',6,6',7,7'-hexaol (2f)

2.1 mL of $BBr_3$ solution (5.56 g, 22.2 mmol) was added dropwise into a solution of 15f (1.23 g, 1.76 mmol) in 60 mL of anhydrous $CH_2Cl_2$ at −78° C. Stirring was continued at −78° C. for 1 h, 0° C. for 1 h, and ambient temperature for 1 h, respectively. 300 grams of ice containing 30 mL of 6M HCl was added to the mixture and stirred for 0.5 h at room temperature. The aqueous layer was extracted with dichloromethane (3×100 mL). The combined organic layer was washed with water, brine and dried over $MgSO_4$. The solvent was concentrated in vacuo and the residue was purified by C-18 column chromatography (H2O/Acetonitrile) to give 1.1 g of compound 2f (90%) as white solid. Yield, 45%; NMR (600 MHz, $CD_3OD$) δ 7.45 (s, 2H), 7.34 (s, 2H), 7.20 (d, J=7.2 Hz, 4H), 7.08 (d, J=7.2 Hz, 4H), 3.27 (m, 4H), 2.87 (m, 4H), 2.31 (s, 6H), 2.03 (s, 6H). HPLC purity 96.6%, $t_R$=17.00 min (Method A). HRMS calcd for $C_{40}H_{38}O_6$ 615.2741 (M+H). found 615.2720.

6,6',7,7'-tetrahydroxy-3,3'-dimethyl-5,5'-bis(4-methylphenethyl)-2,2'-binaphthyl-1,1',4,4'-tetraone (6f)

A solution of compound 2f (1.0 g, 1.55 mmol) in 50 mL of acetone and 80 mL of acetic acid was heated on an oil bath (60-67° C.) during the addition of 68 mL of a 10% aqueous solution of ferric chloride and for several minutes longer. The solution was cooled and 50 mL of water was added followed by 30 mL of aqueous 20% sulfuric acid. The solution was extracted twice with diethyl ether and the organic layer was washed with water, brine and dried over $MgSO_4$. The solvent was concentrated in vacuo and the residue was purified by C-18 column chromatography ($H_2O$/Acetonitrile) to give 350 mg of compound 6f (35%) as yellow solid. $^1$H NMR (600 MHz, $CD_3OD$) δ 7.40 (s, 2H), 7.22 (d, J=7.8 Hz, 4H), 7.08 (d, J=7.2 Hz, 4H), 3.45 (m, 4H), 2.78 (t, $J_1$=8.4 Hz, $J_2$=7.8 Hz, 4H), 2.30 (s, 6H), 1.93 (s, 6H). $^{13}$C NMR (600 MHz, $CD_3OD$) δ 185.65, 182.87, 149.35, 148.72, 146.61, 139.47, 138.20, 134.62, 131.79, 128.32, 128.14, 126.47, 123.95, 110.50, 34.44, 28.68, 19.69, 13.36. HPLC purity 99.0%, $t_R$=17.53 min (Method A). HRMS calcd for $C_oH_{34}O_8$ 643.2326 (M+H). found 643.2326.

Following above mentioned procedure and the appropriate starting materials and reagents used; compounds 6b-l, 6l and 6m were synthesized.

6,6',7,7'-tetrahydroxy-5,5'-diisobutyl-3,3'-dimethyl-2,2'-binaphthyl-1,1',4,4'-tetraone (6b)

Yield, 50%; $^1$H NMR (600 MHz, $CD_3OD$) δ 7.39 (s, 2H), 3.18 (m, 4H), 1.94 (m, 2H), 1.93 (s, 6H), 0.96 (d, J=6.0 Hz, 6H). $^{13}$C NMR (600 MHz, $(CD_3)_2SO$)) δ 185.67, 182.75, 149.97, 149.53, 146.67, 138.38, 132.10, 126.65, 123.60, 111.39, 34.43, 29.18, 23.13, 23.11, 14.96. HPLC purity 96.7%, $t_R$=13.68 min (Method A). HRMS calcd for $C_{30}H_{30}O_8$ 519.2013 (M+H). found 519.2012.

5,5'-bis(cyclopentylmethyl)-6,6',7,7'-tetrahydroxy-3,3'-dimethyl-2,2'-binaphthyl-1,1',4,4'-tetraone (6c)

Yield, 40%; $^1$H NMR (600 MHz, $(CD_3)_2SO$) δ 10.99 (s, br, 2H), 9.54 (s, br, 2H), 7.34 (s, 2H), 3.23 (dd, $J_1$=7.2 Hz, $J_2$=4.8 Hz, 2H), 3.15 (dd, $J_1$=7.2 Hz, $J_2$=4.8 Hz, 2H), 2.10 (m, 2H), 1.87 (s, 6H), 1.61 (m, 8H), 1.45 (m, 4H), 1.26 (m, 4H). $^{13}$C NMR (600 MHz, $(CD_3)_2SO$)) δ 185.25, 182.29, 149.36, 149.00, 146.23, 137.95, 132.26, 126.19, 123.05, 110.84, 40.26, 32.00, 30.65, 24.50, 14.52. HPLC purity 99.0%, $t_R$=16.80 min (Method A). HRMS calcd for $C_{34}H_{34}O_8$ 571.2326 (M+H). found 571.2323.

5,5'-bis(2-cyclohexylethyl)-6,6',7,7'-tetrahydroxy-3,3'-dimethyl-2,2'-binaphthyl-1,1',4,4'-tetraone (6d)

Yield, 50%; $^1$H NMR (600 MHz, $(CD_3)_2SO$) δ 10.88 (s, br, 2H), 9.51 (s, br, 2H), 7.30 (s, 2H), 3.08 (m, 4H), 1.85 (s, 6H), 1.80 (d, J=12.0 Hz, 4H), 1.68 (d, J=12.6 Hz, 4H), 1.61 (d, J=11.4 Hz, 2H), 1.35 (m, 6H), 1.23 (q, J=24.6 Hz, $J_2$=12.6 Hz, 4H), 1.16 (m, 2H), 0.96 (m, 4H). $^{13}$C NMR (600 MHz, $(CD_3)_2SO$)) δ 185.20, 182.22, 148.95, 148.85, 146.16, 138.00, 133.20, 125.96, 123.03, 110.72, 38.02, 36.26, 32.87, 26.32, 25.91, 23.93, 14.44. HPLC purity 98.5%, $t_R$=14.76 min (Method B). HRMS calcd for $C_{38}H_{42}O_8$ 627.2952 (M+H). found 627.2952.

6,6',7,7'-tetrahydroxy-3,3'-dimethyl-5,5'-diphenethyl-2,2'-binaphthyl-1,1',4,4'-tetraone (6e)

Yield, 38%; $^1$H NMR (600 MHz, $CD_3OD$) δ 7.41 (s, 2H), 7.36 (d, J=7.8 Hz, 4H), 7.28 (t, $J_1$=7.8 Hz, $J_2$=7.2 Hz, 4H), 7.16 (t, $J_1$=7.8 Hz, $J_2$=7.2 Hz, 2H), 3.47 (m, 4H), 2.84 (t, $J_1$=8.4 Hz, $J_2$=7.8 Hz, 4H), 1.95 (s, 6H). HPLC purity 99.0%, $t_R$=15.48 min (Method A). HRMS calcd for $C_{38}H_{30}O_8$ 615.2013 (M+H). found 615.2015.

6,6',7,7'-tetrahydroxy-3,3'-dimethyl-5,5'-bis(3-phenylpropyl)-2,2'-binaphthyl-1,1',4,4'-tetraone (6g)

Yield, 42%; $^1$H NMR (600 MHz, $CD_3OD$) δ 7.39 (s, 2H), 7.26 (m, 8H), 7.14 (m, 2H), 3.27 (m, 4H), 2.81 (t, $J_1$=$J_2$=7.8 Hz, 4H), 1.97 (s, 6H), 1.90 (p, $J_1$=$J_2$=7.8 Hz, 4H). $^{13}$C NMR (600 MHz, $CD_3OD$) δ 185.90, 183.4, 149.40, 148.80, 146.70, 142.80, 138.22, 132.54, 127.96, 127.75, 126.61, 125.11, 123.67, 110.42, 36.15, 30.73, 26.21. HPLC purity 98.0%, $t_R$=16.20 min (Method A). HRMS calcd for $C_{40}H_{34}O_8$ 643.2326 (M+H). found 643.2334.

6,6',7,7'-tetrahydroxy-3,3'-dimethyl-5,5'-bis(3-methyl-3-phenylbutyl)-2,2'-binaphthyl-1,1',4,4'-tetraone (6h)

Yield, 50%; $^1$H NMR (600 MHz, CD$_3$OD) δ 7.52 (d, J=7.8 Hz, 4H), 7.36 (s, 2H), 7.32 (t, J$_1$=J$_2$=7.8 Hz, 4H), 7.16 (t, J$_1$=7.2 Hz, J$_2$=7.8 Hz, 2H), 3.04 (t, J$_1$=7.8 Hz, J$_2$=8.4 Hz, 4H), 1.96 (s, 6H), 1.91 (m, 4H), 1.47 (s, 12H). HPLC purity 98.0%, t$_R$=13.5 min (Method B). $^{13}$C NMR (600 MHz, CD$_3$OD) δ 185.36, 182.93, 149.38, 148.47, 146.58, 138.18, 133.24, 131.96, 127.47, 126.47, 125.66, 124.84, 123.69, 110.29, 42.15, 37.51, 35.48, 28.19, 22.01. HRMS calcd for C$_{44}$H$_{42}$O$_8$ 699.2952 (M+H). found 699.2964.

5,5'-dibenzyl-6,6',7,7'-tetrahydroxy-3,3'-dimethyl-2,2'-binaphthyl-1,1',4,4'-tetraone (6i)

Yield, 55%; $^1$H NMR (600 MHz, CD$_3$OD) δ 7.44 (s, 2H), 7.22 (d, J=7.2 Hz, 4H), 7.17 (t, J$_1$=7.2 Hz, J$_2$=7.8 Hz, 4H), 7.17 (t, J$_1$=7.2 Hz, J$_2$=7.8 Hz, 2H), 4.63 (q, J$_1$=11.4 Hz, J$_2$=14.4 Hz, 4H), 1.86 (s, 6H). $^{13}$C NMR (600 MHz, (CD$_3$)$_2$SO)) δ 185.38, 182.54, 149.94, 149.77, 146.53, 140.89, 138.49, 130.01, 128.60, 128.33, 126.45, 125.76, 123.69, 111.68, 31.68, 14.77. HPLC purity 99.6%, t$_R$=12.12 min (Method A). HRMS calcd for C$_{36}$H$_{26}$O$_8$ 587.1700 (M+H). found 587.1710.

5,5'-bis(4-chlorobenzyl)-6,6',7,7'-tetrahydroxy-3,3'-dimethyl-2,2'-binaphthyl-1,1',4,4'-tetraone (6l)

Yield, 60%; $^1$H NMR (600 MHz, CD$_3$OD) δ 7.45 (s, 2H), 7.22 (d, J=6.4 Hz, 4H), 7.18 (d, J=6.4 Hz, 4H), 4.59 (dd, J$_1$=13.8 Hz, J$_2$=26.4 Hz, 4H), 1.85 (s, 6H). HPLC purity 99.0%, t$_R$=14.88 min (Method A). HRMS calcd for C$_{40}$H$_{32}$F$_2$O$_8$ 655.0921 (M+H). found 655.0931.

5,5'-bis(biphenyl-4-ylmethyl)-6,6',7,7'-tetrahydroxy-3,3'-dimethyl-2,2'-binaphthyl-1,1',4,4'-tetraone (6m)

Yield, 52%; $^1$H NMR (600 MHz, CD$_3$OD) δ 7.55 (d, J=7.2 Hz, 4H), 7.44 (d, J=7.8 Hz, 6H), 7.38 (t, J$_1$=7.2 Hz, J$_2$=7.8 Hz, 4H), 7.30 (d, J=7.8 Hz, 4H), 7.27 (t, J$_1$=7.2 Hz, J$_2$=6.6 Hz, 2H), 4.59 (dd, J$_1$=13.8 Hz, J$_2$=27.0 Hz, 4H), 1.88 (s, 6H). HPLC purity 99.0%, t$_R$=16.96 min (Method A). HRMS calcd for C$_{40}$H$_{32}$F$_2$O$_8$ 739.2326 (M+H). found 739.2329.

6,6',7,7'-tetrahydroxy-3,3'-dimethyl-5,5'-bis(4-(trifluoromethoxy)phenethyl)-2,2'-binaphthyl-1,1',4,4'-tetraone (6j)

To a solution of 3j (100 mg, 0.13 mmol) in 25 mL of ethonal and 1 mL acetic acid at room temperature under H$_2$, 10% palladium on carbon (0.10 g) was added and stirred overnight. The solution was extracted twice with diethyl ether and the organic layer was washed with water, brine and dried over MgSO$_4$. The solvent was concentrated in vacuo and the crude residue (2j) was dissolved in 5 mL of acetone and 8 mL of acetic acid was heated on an oil bath (60-67° C.) during the addition of 7 ml of a 10% aqueous solution of ferric chloride and for several minutes longer. The solution was cooled and 5 mL of water was added followed by 3 mL of aqueous 20% sulfuric acid. The solution was extracted twice with diethyl ether and the organic layer was washed with water, brine and dried over MgSO$_4$. The solvent was concentrated in vacuo and the residue was purified by C-18 column chromatography (H$_2$O/Acetonitrile) to give 30 mg of compound 6j (30%) as yellow-brown solid. $^1$H NMR (600 MHz, CD$_3$OD) δ 7.48 (d, J=7.8 Hz, 4H), 7.42 (s, 2H), 7.20 (d, J=7.8 Hz, 4H), 3.48 (m, 4H), 2.88 (t, J$_1$=8.4 Hz, J$_2$=7.2 Hz, 4H), 1.95 (s, 6H). HPLC purity 97.0%, t$_R$=11.67 min (Method B). HRMS calcd for C$_{40}$H$_{28}$F$_6$O$_{10}$ 783.1659 (M+H). found 783.1659.

Following above mentioned procedure and the appropriate starting materials and reagents used; compound 6k was synthesized.

5,5'-bis(3-(4-fluorophenyl)propyl)-6,6',7,7'-tetrahydroxy-3,3'-dimethyl-2,2'-binaphthyl-1,1',4,4'-tetraone (6k)

Yield, 45%; $^1$H NMR (600 MHz, CD$_3$OD) δ 7.37 (s, 2H), 7.24 (m, 4H), 6.97 (m, 4H), 3.26 (m, 4H), 2.78 (t, J$_1$=7.2 Hz, J$_2$=7.8 Hz, 4H), 1.94 (s, 6H), 1.90 (m, 4H). HPLC purity 96.5%, t$_R$=8.76 min (Method B). HRMS calcd for C$_{40}$H$_{32}$F$_2$O$_8$ 679.2138 (M+H). found 679.2150.

Example 4

Evaluation of the Compounds of Formula I Using Cell Viability Assays

The activity of the compounds of Formula I against human cancer cell lines (PC3ML, H460, H1299, RS11846) may be assessed by using the ATP-LITE assay (PerkinElmer). All cells are seeded in either F12 or RPMI1640 medium with 5 mM L-glutamine supplemented with 5% fetal bovine serum (Mediatech Inc.), penicillin and streptomycin (Omega). For maintenance, cells are cultured in 5% FBS. Cells plated into 96 well plates at varying initial densities depending on doubling time. H460 and H1299 plated at 2000 cells/well, A549 and PC3 at 3000 cells/well, and RS118456S at 10,000 cells/well. The compounds are diluted to final concentrations with 0.1% DMSO. Prior to dispensing the compounds onto cells, fresh 5% media is placed into the wells. Administration of compounds occurs 24 hours after seeding into the fresh media. Cell viability may be evaluated using ATP-LITE reagent (PerkinElmer) after 72 hours of treatment. Data are normalized to the DMSO control-treated cells using Prism version 5.01 (Graphpad Software).

The apoptotic activity of the compounds against RS11846 cells may be assessed by staining with Annexin V- and propidium iodide (PI). Lymphoma cell line, RS11846, is cultured in RPMI 1640 medium (Mediatech Inc., Herndon, Va. 20171) containing 10% fetal bovine serum (Mediatech Inc., Herndon, Va. 20171) and Penicillin/Streptomycin (Mediatech Inc., Herndon, Va. 20171). Cells are cultured with various concentrations of a compound of Formula I for 1-2 days. The percentage of viable cells may be determined by FITC-Annexin V- and propidium iodide (PI)-labeling, using an Apoptosis Detection kit (BioVision Inc.), and analyzing stained cells by flow cytometry (FACSort; Bectin-Dickinson, Inc.; Mountain View, Calif.). Cells that are annexin-V-negative and PI-negative are considered viable.

The apoptotic activity of the compounds of Formula I against mouse embryonic fibroblast wild-type cells (MEF/WT) and mouse embryonic fibroblast BAX/Bak double knockout cells (MEF/DKO) may be assessed by staining with Annexin V and propidium iodide (PI). MEF/WT and MEF/DKO cells are seeded in 24-well plate at a seeding density of half a million per well (in 1 ml of DMEM medium supplemented by 10% FCS). The next day, a compound of Formula I may be added to wild-type and DKO cells at final concentration of 0, 2.5, 5.0, 7.5 and 10 μM. On the following day, floating cells are pooled with adherent cells harvested after brief incubation with 0.25% Trypsin/EDTA solution (Gibco/In-Vitrogen Inc.). Cells are centrifuged and supernatant is discarded, and the cell pellet is re-suspended with 0.2 ml of Annexin-V binding buffer, followed by addition of 1 μl Annexin-FITC and 1 μl PI (propidium iodide). The percentage of viable cells may be determined by a 3-color FACSort instrument and data analyzed by Flow-Jo program, scoring Annexin V-negative, PI-negative as viable cells. The EC50 values for the compounds of Formula I are provided below in Table 5.

TABLE 5

| Compound | R = | EC$_{50}$ (μM) | | | |
|---|---|---|---|---|---|
| | | RS4;11 (μM) | H460 (μM) | BP3 (μM) | H1299 (μM) |
| BI97C3 | 2-phenylpropyl acetamide | >30 | 5.7 | 9.1 | ~30 |
| B197C4 | 3-methylbenzyl acetamide | >30 | 6.2 | 28.4 | ~30 |
| BI97C5 | 4-ethylphenethyl acetamide | >30 | 4.4 | 10.1 | 9.1 |
| BI97C6 | phenylacetone | >30 | 7.4 | 6.1 | 10 |
| BI97C7 | sec-butyl | 11.1 | 0.73 | 10.8 | 10.6 |
| B197C9 | cyclopentylethyl | 10.1 | 0.70 | 12.4 | 2.3 |
| BI97C10 | cyclohexylpropyl | 15.6 | 2.2 | 15.5 | 1.3 |
| BI97C11 | phenylpropyl | 4.7 | 1.0 | 7.5 | 0.85 |
| BI97D1 | 4-methylphenylpropyl | 3.1 | 0.59 | 4.0 | 1.56 |
| BI97D4 | phenylbutyl | 3.0 | 0.9 | 6.0 | 1.5 |

TABLE 5-continued

| Compound | R = | RS4;11 (µM) | H460 (µM) | BP3 (µM) | H1299 (µM) |
|---|---|---|---|---|---|
| BI79D5 | (2-phenylpentan-2-yl) | 15.0 | 1.6 | 30.0 | 2.1 |
| BI97D6 | (benzyl) | ND$^{a*}$ | ND | ND | ND |
| BI97D7 | (4-trifluoromethoxyphenyl propyl) | ND | ND | ND | ND |
| BI97D8 | (4-fluorophenyl butyl) | ND | ND | ND | ND |

ND$^{a*}$ = Not determined

Example 5

Cross-Activity of Selected Compounds of Formula I

The cross-activity of selected compounds of Formula I, against Bcl-X$_L$, Bcl-2, Mcl-1 and Bfl-1 using Fluorescence polarization-based competitive binding assay (FPA) is shown below in Table 6.

TABLE 6

| | IC$_{50}$ (µM) | | | |
|---|---|---|---|---|
| Compounds | Bcl-X$_L$ | Bcl-2 | Blf-1 | Mcl-1 |
| BI97C3 | 0.32 | 0.23 | 0.71 | 0.47 |
| BI97C5 | 0.24 | 0.21 | 1.3 | 0.32 |
| BI97C6 | 0.36 | 0.22 | 0.69 | 0.35 |
| BI97C7 | 0.55 | 0.25 | 1.4 | 0.47 |
| BI97C9 | 3.0 | 2.3 | ND$^{a*}$ | 3.1 |
| BI97C10 | 12.6 | 6.7 | ND | 5.9 |

ND$^{a*}$ = Not determined

Example 6

Plasma Stability, Microsomal Stability, and Cell Permeability of Selected Compounds of Formula I To test the pharmacological properties of selected compounds of Formula I, the in vitro plasma stability, microsomal stability, and cell membrane permeability were determined. The results are shown below in Table 7.

TABLE 7

| Compounds | Plasma stability (T = 40 mins) | Microsomal Stability (T = 40 mins) | Cell Permeability |
|---|---|---|---|
| BI97C3 | 91% | 71% | −7.6 |
| BI97C7 | 98% | 69% | −6.1 |
| BI97C10 | 74% | 98% | −5.6 |
| BI97C11 | 81% | 89% | −6.8 |
| BI97D1 | 86% | 52% | −5.0 |
| BI97D4 | 87% | 88% | −7.1 |

ND$^{a*}$ = Not determined

Example 7

Characterization of Selected Compounds of Formula I In Vivo

Figure 21:
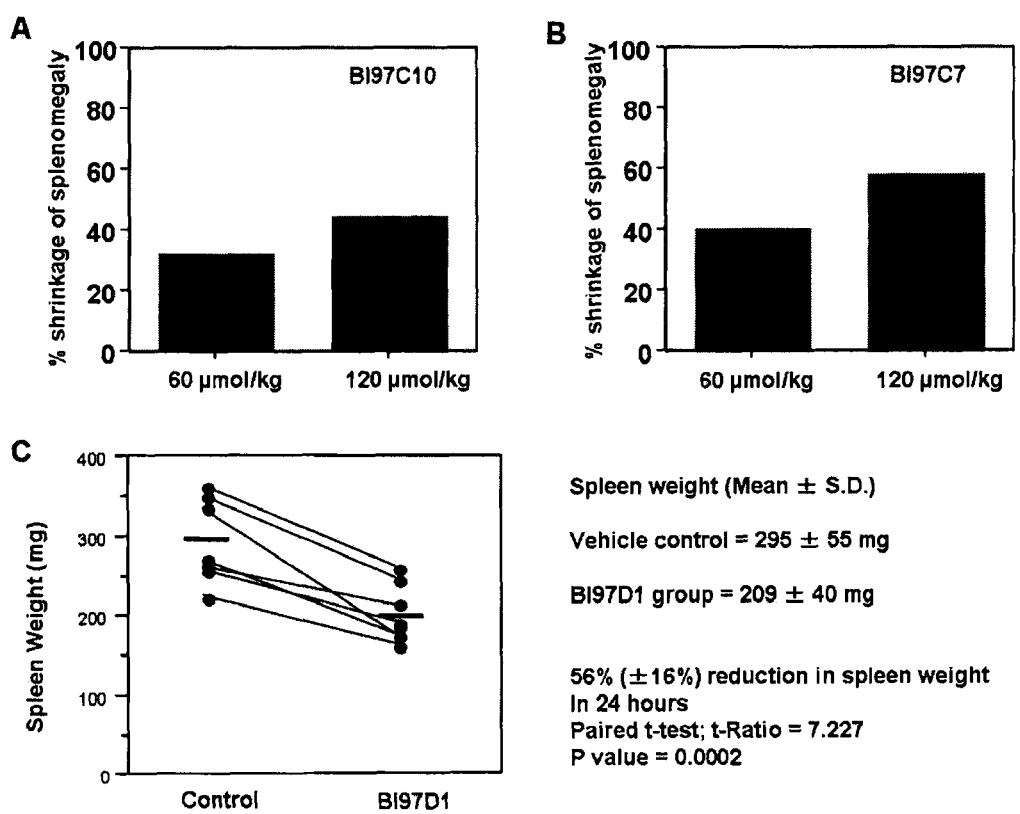
FIG. 21(A) and FIG. 21(B) shows the dose dependent effects of BI97C10 and BI97C7, respectively, on shrinkage of Bcl-2 transgenic mice spleen at a single intraperitoneal injection dose of 0.06 and 0.12 mmol/kg. Also shown in FIG. 21(C), are the effects of compound BI97D1 at 0.12 mmol/kg on reduction of spleen weight of seven Bcl-2 transgenic mice treatment with a single intraperitoneal injection. No toxicity was observed.

The characterization of selected compounds of Formula I in vivo may be determined. As shown in FIG. 21(A) and FIG. 21(B), the dose dependent effects of BI97C10 and BI97C7, respectively, on shrinkage of Bcl-2 transgenic mice spleen at a single intraperitoneal injection dose of 0.06 and 0.12 mmol/kg did not show any toxicity. All shrinkage data are percentage of maximum reduction of mice spleen size. Also shown in FIG. 21(C), are the effects of compound BI97D1 at 0.12 mmol/kg on reduction of spleen weight of seven Bcl-2 transgenic mice treatment with a single intraperitoneal injection. Data shown as means±S.D. (n=7). P=0.0002. No toxicity is observed.

Example 9

Molecular Modeling

Molecular modeling studies were conducted on a Linux workstation and a 64 3.2-GHz CPUs Linux cluster. Docking studies may be performed using the crystal structure of BCL-$X_L$ in complex with Bak-derived peptide (Protein Data Bank code 1BXL). The docked structures of the compounds having Formula I in the peptide-binding pocket may be obtained by ChemScore as the scoring function in the GOLD docking program. The protein surface may be prepared with the program MOLCAD as implemented in Sybyl (Tripos, St. Louis). Docking studies may also be performed using the crystal structure of Bcl-2 in complex with a benzothiazole BH3 mimetic ligand (Protein Data Bank code 1YSW). The ligand may be extracted from the protein structure and used to define the binding site for small molecules. Apogossypol and its derivatives may be docked into the Bcl-2 protein by the GOLD docking program using ChemScore as the scoring function. The active site radius may be set at 10 Å and 10 GA solutions generated for each molecule. The GA docking procedure in GOLD allows the small molecules to flexibly explore the best binding conformations while the protein structure is static. The protein surface may be prepared with the program MOLCAD as implemented in Sybyl (Tripos, St. Louis) and used to analyze the binding poses for the studied small molecules.

Example 10

Fluorescence Polarization Assays (FPA)

A Bak BH3 peptide (F-BakBH3) (GQVGRQLAIIGD-DINR (SEQ ID NO:1)) was labeled at the N-terminus with fluorescein isothiocyanate (FITC) (Molecular Probes) and purified by HPLC. For competitive binding assays, 100 nM GST-BCL-$X_L$ ΔTM protein was preincubated with the tested compound at varying concentrations in 47.5 μL PBS (pH=7.4) in 96-well black plates at room temperature for 10 min, then 2.5 μL of 100 nM FITC-labeled Bak BH3 peptide was added to produce a final volume of 50 μL. The wild-type and mutant Bak BH3 peptides were included in each assay plate as positive and negative controls, respectively. After 30 min incubation at room temperature, the polarization values in millipolarization units were measured at excitation/emission wavelengths of 480/535 nm with a multilabel plate reader (PerkinElmer). $IC_{50}$ was determined by fitting the experimental data to a sigmoidal dose-response nonlinear regression model (SigmaPlot 10.0.1, Systat Software, Inc., San Jose, Calif., USA). Data reported are mean of three independent experiments±standard error (SE). Performance of BCL-2 and Mcl-1 FPA are similar. Briefly, 50 nM of GST-BCL-2 or -Mcl-1 were incubated with various concentrations of Apogossypol, or its derivatives for 2 min, then 15 nM FITC-conjugated-Bim BH3 peptide was added in PBS buffer. Fluorescence polarization was measured after 10 min.

Example 11

Cell Viability and Apoptosis Assays

The activity of the compounds against human cancer cell lines (PC3, H460, H1299) were assessed by using the ATP-LITE assay (PerkinElmer). All cells were seeded in either 12F2 or RPMI1640 medium with 5 mM L-glutamine supplemented with 5% fetal bovine serum (Mediatech Inc.), penicillin and streptomycin (Omega). For maintenance, cells were cultured in 5% FBS. Cells plated into 96 well plates at varying initial densities depending on doubling time. H460 and H1299 plated at 2000 cells/well and PC3 at 3000 cells/well. Compounds were diluted to final concentrations with 0.1% DMSO. Prior to dispensing compounds onto cells, fresh 5% media was placed into wells. Administration of compounds occurred 24 hours after seeding into the fresh media. Cell viability was evaluated using ATP-LITE reagent (PerkinElmer) after 72 hours of treatment. Data were normalized to the DMSO control-treated cells using Prism version 5.01 (Graphpad Software).

The apoptotic activity of the compounds against RS4;11, BP3 and primary CLL cells was assessed by staining with Annexin V-FITC and propidium iodide (PI). Cells were cultured in RPMI 1640 medium (Mediatech Inc., Herndon, Va. 20171) containing 10% fetal bovine serum (Mediatech Inc., Herndon, Va. 20171) and Penicillin/Streptomycin (Mediatech Inc., Herndon, Va. 20171). Cells were cultured with various concentrations of 5,5' substituted 6a derivatives for 1 day. The percentage of viable cells was determined by FITC-Annexin V- and propidium iodide (PI)-labeling, using an Apoptosis Detection kit (BioVision Inc.), and analyzing stained cells by flow cytometry (FACSort; Bectin-Dickinson, Inc.; Mountain View, Calif.). Cells that were annexin-V-negative and PI-negative were considered viable.

Example 12

BCL-2 Transgenic Mice Studies

Transgenic mice expressing Bcl-2 have been described as the B6 line.[56] The BCL-2 transgene represents a minigene version of a t(14;18) translocation in which the human BCL-2 gene is fused with the immunoglobulin heavy-chain (IgH) locus and associated IgH enhancer. The transgene was propagated on the Balb/c background. These mice develop polyclonal B-cell hyperplasia with asynchronous transformation to monoclonal aggressive lymphomas beginning at approximately 6 months of age, with approximately 90% of mice undergoing transformation by the age of 12 to 24 months. All animals used here had not yet developed aggressive lymphoma. Compounds dissolved in 500 μL of solution (Ethanol:Cremophor EL:Saline=10:10:80) were injected intraperitoneally to age- and sex-matched B6Bcl2 mouse, while control-mice were injected intraperitoneally with 500 μL of the same formulation without compound. After 24 hours, B6Bcl2 mice were sacrificed by intraperitoneal injection of lethal dose of Avertin. Spleen was removed and weighed. The spleen weight of mice is used as an end-point for assessing activity as it was determined that spleen weight is highly consistent in age- and sex-matched Bcl-2-transgenic mice in preliminary studies. Variability of spleen weight was within ±2% among control-treated age-matched, sex-matched B6Bcl2 mice.

Example 13

Tumor Xenograft Studies

Female 6-week-old nude mice were purchased from Charles River Laboratories. 5×10⁶ PCC-1 cells suspended in 0.2 ml PBS were injected subcutaneously into a flank region of each nude mouse. Tumor bearing mice were size matched (200 mm³) into treatment and control group, ear tagged, and monitored individually. Tumor volume was measured two to three times weekly by digital calipers (volume=length×width$^2$/2). All studies use 6 mice per group. Compounds dissolved in 500 μL of solvent (Ethanol:Cremophor EL/saline=10:10:80) were injected intraperitoneally (i.p.) into tumor-bearing mice. Control mice received saline. The injections were given three times in first week, twice in second week and once in third week and a total of six injections were administered during the experiment. When all tumors of the control group exceed 2000 mm$^3$ in volume, the animal experiment was terminated. Tumor growth inhibition ratios (T/C %) were calculated by dividing the average tumor volume in the treatment group by the average tumor volume in the control group.

REFERENCES

Vaux, D. L.; Korsmeyer, S. J. Cell death in development. *Cell* 1999, 96, 245-254.

Reed, J. C. Dysregulation of apoptosis in cancer. *J Clin Oncol* 1999, 17, 2941-2953.

Johnstone, R. W.; Ruefli, A. A.; Lowe, S. W. Apoptosis: a link between cancer genetics and chemotherapy. *Cell* 2002, 108, 153-164.

Reed, J. C. Apoptosis-based therapies. *Nature reviews Drug discovery* 2002, 1, 111-121.

Reed, J. C. Molecular biology of chronic lymphocytic leukemia: implications for therapy. *Seminars in hematology* 1998, 35, 3-13.

Adams, J. M.; Cory, S. The Bcl-2 protein family: arbiters of cell survival. *Science* (New York, N.Y.) 1998, 281, 1322-6.

Gross, A.; McDonnell, J. M.; Korsmeyer, S. J. BCL-2 family members and the mitochondria in apoptosis. *Genes & development* 1999, 13, 1899-911.

Wang, J. L.; Liu, D.; Zhang, Z. J.; Shan, S.; Han, X.; Srinivasula, S. M.; Croce, C. M.; Alnemri, E. S.; Huang, Z. Structure-based discovery of an organic compound that binds Bcl-2 protein and induces apoptosis of tumor cells. *Proceedings of the National Academy of Sciences of the United States of America* 2000, 97, 7124-9.

Degterev, A.; Lugovskoy, A.; Cardone, M.; Mulley, B.; Wagner, G.; Mitchison, T.; Yuan, J. Identification of small-molecule inhibitors of interaction between the BH3 domain and Bcl-xL. *Nat Cell Biol* 2001, 3, 173-82.

Reed, J. C. Bcl-2 family proteins. *Oncogene* 1998, 17, 3225-36.

Reed, J. C. Bcl-2 family proteins: strategies for overcoming chemoresistance in cancer. *Advances in pharmacology* (San Diego, Calif.) 1997, 41, 501-32.

Kitada, S.; Leone, M.; Sareth, S.; Zhai, D.; Reed, J. C.; Pellecchia, M. Discovery, characterization, and structure-activity relationships studies of proapoptotic polyphenols targeting B-cell lymphocyte/leukemia-2 proteins. *Journal of medicinal chemistry* 2003, 46, 4259-64.

Zhang, M.; Liu, H.; Guo, R.; Ling, Y.; Wu, X.; Li, B.; Roller, P. P.; Wang, S.; Yang, D. Molecular mechanism of Gossypol-induced cell growth inhibition and cell death of HT-29 human colon carcinoma cells. *Biochemical pharmacology* 2003, 66, 93-103.

Wang, G.; Nikolovska-Coleska, Z.; Yang, C.-Y.; Wang, R.; Tang, G.; Guo, J.; Shangary, S.; Qiu, S.; Gao, W.; Yang, D.; Meagher, J.; Stuckey, J.; Krajewski, K.; Jiang, S.; Roller, P. P.; Abaan, H. O.; Tomita, Y.; Wang, S. Structure-based design of potent small-molecule inhibitors of anti-apoptotic Bcl-2 proteins. *Journal of medicinal chemistry* 2006, 49, 6139-42.

Oliver, C. L.; Miranda, M. B.; Shangary, S.; Land, S.; Wang, S.; Johnson, D. E. (−)-Gossypol acts directly on the mitochondria to overcome Bcl-2- and Bcl-X(L)-mediated apoptosis resistance. *Mol Cancer Ther* 2005, 4, 23-31.

Mohammad, R. M.; Wang, S.; Aboukameel, A.; Chen, B.; Wu, X.; Chen, J.; Al-Katib, A. Preclinical studies of a nonpeptidic small-molecule inhibitor of Bcl-2 and Bcl-X(L) [(−)-gossypol] against diffuse large cell lymphoma. *Mol Cancer Ther* 2005, 4, 13-21.

Wang, S. Y., D. Small Molecular Antagonists of Bcl-2 family proteins. US patent applications series no. 2003008924. May 30, 2002.

Meng, Y.; Tang, W.; Dai, Y.; Wu, X.; Liu, M.; Ji, Q.; Ji, M.; Pienta, K.; Lawrence, T.; Xu, L. Natural BH3 mimetic (−)-gossypol chemosensitizes human prostate cancer via Bcl-xL inhibition accompanied by increase of Puma and Noxa. *Mol Cancer Ther* 2008, 7, 2192-2202.

Becattini, B.; Kitada, S.; Leone, M.; Monosov, E.; Chandler, S.; Zhai, D.; Kipps, T. J.; Reed, J. C.; Pellecchia, M. Rational design and real time, in-cell detection of the proapoptotic activity of a novel compound targeting Bcl-X(L). *Chemistry & biology* 2004, 11, 389-95.

Kitada, S.; Kress, C. L.; Krajewska, M.; Jia, L.; Pellecchia, M.; Reed, J. C. Bcl-2 antagonist Apogossypol (NSC736630) displays single-agent activity in Bcl-2-transgenic mice and has superior efficacy with less toxicity compared with Gossypol (NSC 19048). *Blood* 2008, 111, 3211-9.

Coward, L.; Gorman, G.; Noker, P.; Kerstner-Wood, C.; Pellecchia, M.; Reed, J. C.; Jia, L. Quantitative determination of Apogossypol, a pro-apoptotic analog of Gossypol, in mouse plasma using LC/MS/MS. *Journal of pharmaceutical and biomedical analysis* 2006, 42, 581-6.

Wei, J.; Rega, M. F.; Kitada, S.; Yuan, H.; Zhai, D.; Risbood, P.; Seltzman, H. H.; Twine, C. E.; Reed, J. C.; Pellecchia, M. Synthesis and evaluation of Apogossypol atropisomers as potential Bcl-xL antagonists. *Cancer Lett* 2009, 273, 107-113.

Jun Wei, S. K., Michele F. Rega, Aras Emdadi, Hongbin Yuan, Jason Cellitti, John L. Stebbins, Dayong Zhai, Jiazhi Sun, Li Yang, Russell Dahl, Ziming Zhang, Bainan Wu, Si Wang, Tyler A. Reed, Nicholas Lawrence, Said Sebti,; Pellecchia, J. C. R. A. M. Apogossypol Derivatives as Antagonists of Anti-apoptotic Bcl-2 Family Proteins. *Mol Cancer Ther* 2009, in press.

Oltersdorf, T.; Elmore, S. W.; Shoemaker, A. R.; Armstrong, R. C.; Augeri, D. J.; Belli, B. A.; Bruncko, M.; Deckwerth, T. L.; Dinges, J.; Hajduk, P. J.; Joseph, M. K.; Kitada, S.; Korsmeyer, S. J.; Kunzer, A. R.; Letai, A.; Li, C.; Mitten, M. J.; Nettesheim, D. G.; Ng, S.; Nimmer, P. M.; O'Connor, J. M.; Oleksijew, A.; Petros, A. M.; Reed, J. C.; Shen, W.; Tahir, S. K.; Thompson, C. B.; Tomaselli, K. J.; Wang, B.; Wendt, M. D.; Zhang, H.; Fesik, S. W.; Rosenberg, S. H. An inhibitor of Bcl-2 family proteins induces regression of solid tumours. *Nature* 2005, 435, 677-81.

Bruncko, M.; Oost, T. K.; Belli, B. A.; Ding, H.; Joseph, M. K.; Kunzer, A.; Martineau, D.; McClellan, W. J.; Mitten, M.; Ng, S. C.; Nimmer, P. M.; Oltersdorf, T.; Park, C. M.; Petros, A. M.; Shoemaker, A. R.; Song, X.; Wang, X.; Wendt, M. D.; Zhang, H.; Fesik, S. W.; Rosenberg, S. H.; Elmore, S. W. Studies leading to potent, dual inhibitors of Bcl-2 and Bcl-xL. *J Med Chem* 2007, 50, 641-62.

Meltzer, P. C.; Bickford, H. P.; Lambert, G. J. A Regioselective Route to Gossypol Analogues: The Synthesis of Gossypol and 5,5'-Didesisopropyl-5,5'-diethylgossypol. *J. Org. Chem.* 1985, 50, 3121-3124.

Royer, R. E.; Deck, L. M.; Vander Jagt, T. J.; Martinez, F. J.; Mills, R. G.; Young, S. A.; Vander Jagt, D. L. Synthesis and anti-HIV activity of 1,1'-dideoxygossypol and related compounds. *J Med Chem* 1995, 38, 2427-32.

Yamanoi, Y.; Nishihara, H. Direct and selective arylation of tertiary silanes with rhodium catalyst. *J Org Chem* 2008, 73, 6671-8.

Tang, G.; Ding, K.; Nikolovska-Coleska, Z.; Yang, C. Y.; Qiu, S.; Shangary, S.; Wang, R.; Guo, J.; Gao, W.; Meagher, J.; Stuckey, J.; Krajewski, K.; Jiang, S.; Roller, P. P.; Wang, S. Structure-based design of flavonoid compounds as a new class of small-molecule inhibitors of the anti-apoptotic Bcl-2 proteins. *J Med Chem* 2007, 50, 3163-6.

Rega, M. F.; Leone, M.; Jung, D.; Cotton, N. J.; Stebbins, J. L.; Pellecchia, M. Structure-based discovery of a new class of Bcl-xL antagonists. *Bioorg Chem* 2007, 35, 344-53.

Wesarg, E.; Hoffarth, S.; Wiewrodt, R.; Kroll, M.; Biesterfeld, S.; Huber, C.; Schuler, M. Targeting BCL-2 family proteins to overcome drug resistance in non-small cell lung cancer. *Int J Cancer* 2007, 121, 2387-94.

Brien, G.; Trescol-Biemont, M. C.; Bonnefoy-Berard, N. Downregulation of Bfl-1 protein expression sensitizes malignant B cells to apoptosis. *Oncogene* 2007, 26, 5828-32.

Li, J.; Viallet, J.; Haura, E. B. A small molecule pan-Bcl-2 family inhibitor, GX15-070, induces apoptosis and enhances cisplatin-induced apoptosis in non-small cell lung cancer cells. *Cancer Chemother Pharmacol* 2008, 61, 525-34.

Voortman, J.; Checinska, A.; Giaccone, G.; Rodriguez, J. A.; Kruyt, F. A. Bortezomib, but not cisplatin, induces mitochondria-dependent apoptosis accompanied by up-regulation of noxa in the non-small cell lung cancer cell line NCI-H460. *Mol Cancer Ther* 2007, 6, 1046-53.

Ferreira, C. G.; Span, S. W.; Peters, G. J.; Kruyt, F. A.; Giaccone, G. Chemotherapy triggers apoptosis in a caspase-8-dependent and mitochondria-controlled manner in the non-small cell lung cancer cell line NCI-H460. *Cancer Res* 2000, 60, 7133-41.

Cory, S.; Adams, J. M. Killing cancer cells by flipping the Bcl-2/Bax switch. *Cancer cell* 2005, 8, 5-6.

Wei, M. C.; Zong, W. X.; Cheng, E. H.; Lindsten, T.; Panoutsakopoulou, V.; Ross, A. J.; Roth, K. A.; MacGregor, G. R.; Thompson, C. B.; Korsmeyer, S. J. Proapoptotic BAX and BAK: a requisite gateway to mitochondrial dysfunction and death. *Science* (New York, N Y) 2001, 292, 727-30.

Zhai, D.; Jin, C.; Shiau, C. W.; Kitada, S.; Satterthwait, A. C.; Reed, J. C. Gambogic acid is an antagonist of antiapoptotic Bcl-2 family proteins. *Mol Cancer Ther* 2008, 7, 1639-46.

Wei, J.; Kitada, S.; Rega, M. F.; Emdadi, A.; Yuan, H.; Cellitti, J.; Stebbins, J. L.; Zhai, D.; Sun, J.; Yang, L.; Dahl, R.; Zhang, Z.; Wu, B.; Wang, S.; Reed, T. A.; Lawrence, N.; Sebti, S.; Reed, J. C.; Pellecchia, M. Apogossypol derivatives as antagonists of antiapoptotic Bcl-2 family proteins. *Mol Cancer Ther* 2009, 8, 904-913.

Wei, J.; Kitada, S.; Rega, M. F.; Stebbins, J. L.; Zhai, D.; Cellitti, J.; Yuan, H.; Emdadi, A.; Dahl, R.; Zhang, Z.; Yang, L.; Reed, J. C.; Pellecchia, M. Apogossypol derivatives as pan-active inhibitors of antiapoptotic B-cell lymphoma/leukemia-2 (Bcl-2) family proteins. *Journal of medicinal chemistry* 2009, 52, 4511-4523.

Wei, J.; Stebbins, J. L.; Kitada, S.; Dash, R.; Placzek, W.; Rega, M. F.; Wu, B.; Cellitti, J.; Zhai, D.; Yang, L.; Dahl, R.; Fisher, P. B.; Reed, J. C.; Pellecchia, M. BI-97C1, an optically pure Apogossypol derivative as pan-active inhibitor of antiapoptotic B-cell lymphoma/leukemia-2 (Bcl-2) family proteins. *J Med Chem*, 2010, 53, 4166-4176.

Shelley, M. D.; Hartley, L.; Fish, R. G.; Groundwater, P.; Morgan, J. J.; Mort, D.; Mason, M.; Evans, A. Stereospecific cytotoxic effects of Gossypol enantiomers and Gossypolone in tumour cell lines. *Cancer letters* 1999, 135, 171-180.

Flack, M. R.; Knazek, R.; Reidenberg, M. Gossypolone for the treatment of cancer U.S. Pat. No. 40862. 2009.

Wang, S.; Nikolovska-Coleska, Z.; Yang, C.-Y.; Chen, J pogossypolone and the uses thereof. PCT Int. Appl, WO 2006050447 A2 20060511. 2006.

Sun, J.; Li, Z.-M.; Hu, Z.-Y.; Zeng, Z.-L.; Yang, D.-J.; Jiang, W.-Q. Apogossypolone inhibits cell growth by inducing cell cycle arrest in U937 cells. *Oncology reports* 2009, 22, 193-198.

Lin, J.; Wu, Y.-J.; Yang, D.-J.; Zhao, Y.-Q. [Effect of Apogossypolone on induction apoptosis in multiple myeloma cells and its mechanisms]. *Zhongguo shi yan xue ye xue za zhi/Zhongguo bing li sheng li xue hui=Journal of experimental hematology/Chinese Association of Pathophysiology* 2009, 17, 92-98.

Arnold, A. A.; Aboukameel, A.; Chen, J.; Yang, D.; Wang, S.; Al-Katib, A.; Mohammad, R. M. Preclinical studies of Apogossypolone: a new nonpeptidic pan small-molecule inhibitor of Bcl-2, Bcl-XL and Mcl-1 proteins in Follicular Small Cleaved Cell Lymphoma model. *Molecular cancer* 2008, 7, 20.

Mi, J. X.; Wang, G. F.; Wang, H. B.; Sun, X. Q.; Ni, X. Y.; Zhang, X. W.; Tang, J. M.; Yang, D. J. Synergistic antitumoral activity and induction of apoptosis by novel pan Bcl-2 proteins inhibitor Apogossypolone with adriamycin in human hepatocellular carcinoma. *Acta Pharmacol Sin* 2008, 29, 1467-1477.

Hu, Z. Y.; Zhu, X. F.; Zhong, Z. D.; Sun, J.; Wang, J.; Yang, D.; Zeng, Y. X. ApoG2, a novel inhibitor of antiapoptotic Bcl-2 family proteins, induces apoptosis and suppresses tumor growth in nasopharyngeal carcinoma xenografts. *Int J Cancer* 2008, 123, 2418-2429.

Adams, R.; Butterbaugh, D. J. Structure of Gossypol. X. Apogossypol and its Degradation Products. *J. Am. Chem. SOC.* 1938, 60, 2174-2180.

Du, Y.; Liu, R.; Linn, G.; Zhao, K. Synthesis of N-substituted indole derivatives via PIFA-mediated intramolecular cyclization. *Org Lett* 2006, 8, 5919-5922.

Islam, I.; Skibo, E. B.; Dorr, R. T.; Alberts, D. S. Structure-activity studies of antitumor agents based on pyrrolo[1,2-a]benzimidazoles: new reductive alkylating DNA cleaving agents. *J Med Chem* 1991, 34, 2954-2961.

Dao, V. T.; Gaspard, C.; Mayer, M.; Werner, G. H.; Nguyen, S, N.; Michelot, R. J. Synthesis and cytotoxicity of Gossypol related compounds. *Eur J Med Chem* 2000, 35, 805-813.

Sakamoto, K.; Miyoshi, H.; Takegami, K.; Mogi, T.; Anraku, Y.; Iwamura, H. Probing substrate binding site of the *Escherichia coli* quinol oxidases using synthetic ubiquinol analogues. *J Biol Chem* 1996, 271, 29897-29902.

Li, J.; Viallet, J.; Haura, E. B. A small molecule pan-Bcl-2 family inhibitor, GX15-070, induces apoptosis and enhances cisplatin-induced apoptosis in non-small cell lung cancer cells. *Cancer Chemother Pharmacol* 2008, 61, 525-534.

Jones, G.; Willett, P.; Glen, R. C.; Leach, A. R.; Taylor, R. Development and validation of a genetic algorithm for flexible docking. *Journal of molecular biology* 1997, 267, 727-748.

Eldridge, M. D.; Murray, C. W.; Auton, T. R.; Paolini, G. V.; Mee, R. P. Empirical scoring functions: I. The development of a fast empirical scoring function to estimate the binding affinity of ligands in receptor complexes. *J Comput Aided Mol Des* 1997, 11, 425-445.

Teschner, M.; Henn, C.; Vollhardt, H.; Reiling, S.; Brickmann, J. Texture mapping: a new tool for molecular graphics. *J Mol Graph* 1994, 12, 98-105.

Sattler, M.; Liang, H.; Nettesheim, D.; Meadows, R. P.; Harlan, J. E.; Eberstadt, M.; Yoon, H. S.; Shuker, S. B.; Chang, B. S.; Minn, A. J.; Thompson, C. B.; Fesik, S. W. Structure of Bcl-xL-Bak peptide complex: recognition between regulators of apoptosis. *Science* (New York, N Y) 1997, 275, 983-986.

Ramjaun, A. R.; Tomlinson, S.; Eddaoudi, A.; Downward, J. Upregulation of two BH3-only proteins, Bmf and Bim, during TGF beta-induced apoptosis. *Oncogene* 2007, 26, 970-981.

Katsumata, M.; Siegel, R. M.; Louie, D. C.; Miyashita, T.; Tsujimoto, Y.; Nowell, P. C.; Greene, M. I.; Reed, J. C. Differential effects of Bcl-2 on T and B cells in transgenic mice. *Proc Natl Acad Sci USA* 1992, 89, 11376-11380.

Although the disclosure has been described with reference to the above examples, it will be understood that modifications and variations are encompassed within the spirit and scope of the disclosure.

What is claimed is:

1. A compound of Formula I:

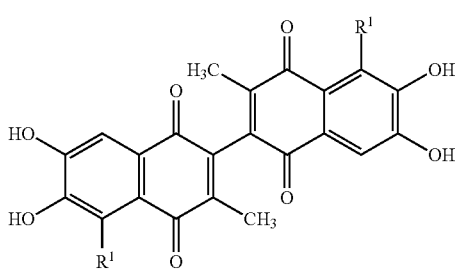

I or a pharmaceutically acceptable salt, hydrate, or solvate thereof,
wherein:

$R^1$ is independently hydrogen, halogen, amino, nitro, cyano, hydroxyl, substituted or unsubstituted alkoxy, substituted or unsubstituted heteroalkyl, substituted or unsubstituted heterocyclic, substituted or unsubstituted aryl, substituted or unsubstituted arylalkyl, substituted or unsubstituted heteroaryl, substituted or unsubstituted heteroarylalkyl, —$(CH_2)_jOR^2$, —$(CH_2)_jC(O)R^2$, —$(CH_2)_jC(O)OR^2$, —$(CH_2)_jOC(O)R^2$, —$(CH_2)_jNR^3R^4$, —$(CH_2)_jC(O)NR^3R^4$, —$(CH_2)_jOC(O)NR^3R^4$, —$(CH_2)_jNR^5C(O)R^2$, —$(CH_2)_jNR^5C(O)OR^2$, —$(CH_2)_jNR^5C(O)NR^3R^4$, —$(CH_2)_jS(O)_mR^6$, or —$(CH_2)_jNR^5S(O)_mR^6$, wherein j is an integer from 0 to 12; and m is an integer from 0 to 2;

$R^2$ is independently hydrogen, substituted or unsubstituted alkyl, substituted or unsubstituted cycloalkyl, perfluoroalkyl, substituted or unsubstituted alkenyl, substituted or unsubstituted alkynyl, substituted or unsubstituted heteroalkyl, substituted or unsubstituted heterocyclic, substituted or unsubstituted aryl, substituted or unsubstituted arylalkyl, substituted or unsubstituted heteroaryl, substituted or unsubstituted heteroarylalkyl;

$R^3$ and $R^4$ are each independently hydrogen, substituted or unsubstituted alkyl, substituted or unsubstituted cycloalkyl, perfluoroalkyl, substituted or unsubstituted alkenyl, substituted or unsubstituted alkynyl, substituted or unsubstituted heteroalkyl, substituted or unsubstituted heterocyclic, substituted or unsubstituted aryl, substituted or unsubstituted arylalkyl, substituted or unsubstituted heteroaryl, substituted or unsubstituted heteroarylalkyl, or $R^3$ and $R^4$, together with the N atom to which they are attached, form substituted or unsubstituted heterocyclic, or substituted or unsubstituted heteroaryl;

$R^5$ is independently hydrogen, substituted or unsubstituted alkyl, substituted or unsubstituted cycloalkyl, perfluoroalkyl, substituted or unsubstituted alkenyl, substituted or unsubstituted alkynyl, substituted or unsubstituted heteroalkyl, substituted or unsubstituted heterocyclic, substituted or unsubstituted aryl, substituted or unsubstituted arylalkyl, substituted or unsubstituted heteroaryl, substituted or unsubstituted heteroarylalkyl;

$R^6$ is independently hydrogen, substituted or unsubstituted alkyl, substituted or unsubstituted cycloalkyl, perfluoroalkyl, substituted or unsubstituted alkenyl, substituted or unsubstituted alkynyl, substituted or unsubstituted heteroalkyl, substituted or unsubstituted heterocyclic, substituted or unsubstituted aryl, substituted or unsubstituted arylalkyl, substituted or unsubstituted heteroaryl, substituted or unsubstituted heteroarylalkyl;

$R^1$, $R^2$, $R^3$, $R^4$, $R^5$, and $R^6$ are optionally independently substituted with 1 to 3 groups selected from hydrogen, halogen, amino, nitro, cyano, hydroxyl, alkyl, cycloalkyl, perfluoroalkyl, alkenyl, alkynyl, alkoxy, heteroalkyl, heterocyclic, aryl, arylalkyl, heteroaryl, heteroarylalkyl, —$(CH_2)_jOR^7$, —$(CH_2)_jC(O)R^7$, —$(CH_2)_jC(O)OR^7$, —$(CH_2)_jOC(O)R^7$, —$(CH_2)$ $_j$NR$^8$R$^9$, —(CH$_2$)$_j$C(O)NR$^8$R$^9$, —(CH$_2$)$_j$OC(O)NR$^8$R$^9$, —(CH$_2$)$_j$NR$^{10}$C(O)R$^7$, —(CH$_2$)$_j$NR$^{10}$C(O)OR$^7$, —(CH$_2$)$_j$NR$^{10}$C(O)NR$^8$R$^9$, —(CH$_2$)$_j$S(O)$_m$R$^{11}$ or —(CH$_2$)$_j$NR$^{10}$S(O)$_m$R$^{11}$, wherein j is an integer from 0 to 12; and m is an integer from 0 to 2;

R$^7$ is independently hydrogen, alkyl, cycloalkyl, perfluoroalkyl, alkenyl, alkynyl, heteroalkyl, heterocyclic, aryl, arylalkyl, heteroaryl, or heteroarylalkyl;

R$^8$ and R$^9$ are each independently hydrogen, alkyl, cycloalkyl, perfluoroalkyl, alkenyl, alkynyl, heteroalkyl, heterocyclic, aryl, arylalkyl, heteroaryl, heteroarylalkyl, or R$^8$ and R$^9$, together with the N atom to which they are attached, form heterocyclic or heteroaryl;

R$^{10}$ is independently hydrogen, alkyl, cycloalkyl, perfluoroalkyl, alkenyl, alkynyl, heteroalkyl, heterocyclic, aryl, arylalkyl, heteroaryl, or heteroarylalkyl; and R$^{11}$ is independently hydrogen, alkyl, cycloalkyl, perfluoroalkyl, alkenyl, alkynyl, heteroalkyl, heterocyclic, aryl, arylalkyl, heteroaryl, or heteroarylalkyl.

2. The compound of claim 1, wherein R$^1$ is —(CH$_2$)$_j$C(O)NR$^3$R$^4$; and R$^3$ and R$^4$ are each independently hydrogen, substituted or unsubstituted alkyl, or substituted or unsubstituted arylalkyl.

3. The compound of claim 2, wherein j is 0; R$^3$ is hydrogen; and R$^4$ is —CH$_2$CH(CH$_3$)C$_6$H$_5$, —CH$_2$(C$_6$H$_4$)CH$_3$, or —CH$_2$(C$_6$H$_4$)CH$_2$CH$_3$.

4. The compound of claim 2, wherein j is 0; R$^3$ is hydrogen; and R$^4$ is

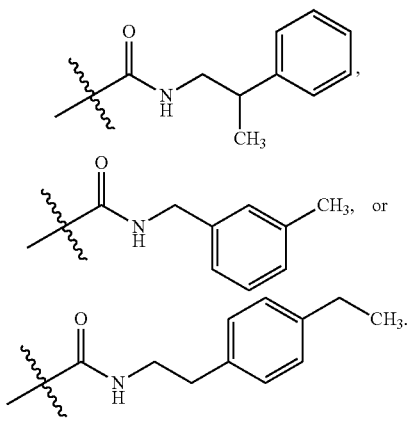

5. The compound of claim 1, wherein R$^1$ is —(CH$_2$)$_j$C(O)R$^2$; and R$^2$ is substituted or unsubstituted alkyl, substituted or unsubstituted arylalkyl.

6. The compound of claim 5, wherein j is 0; and R$^2$ is CH$_2$C$_6$H$_5$.

7. The compound of claim 1, wherein R$^1$ is substituted or unsubstituted arylalkyl.

8. The compound of claim 7, wherein R$^1$ is substituted or unsubstituted aryl(C$_1$-C$_6$)alkyl.

9. The compound of claim 8, wherein R$^1$ is substituted or unsubstituted —(C$_1$-C$_6$)alkyl(C$_6$H$_5$).

10. The compound of claim 9, wherein R$^1$ is

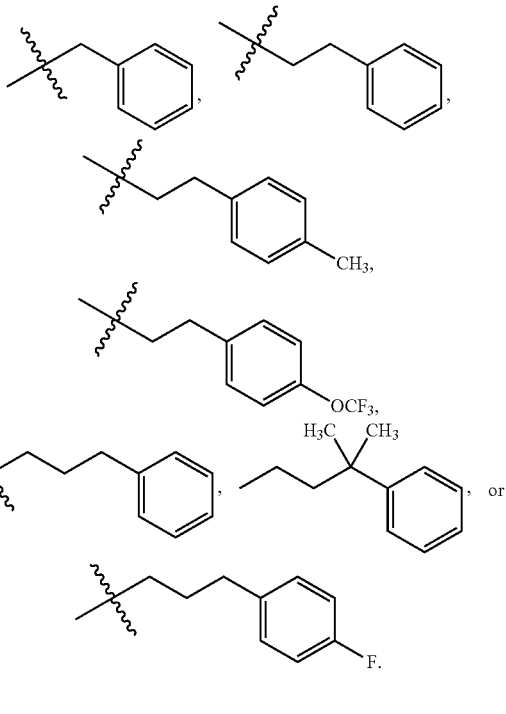

11. The compound of claim 10, wherein R$^1$ is

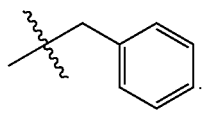 [SMILES: *Cc1ccccc1]

* * * * *

UNITED STATES PATENT AND TRADEMARK OFFICE
CERTIFICATE OF CORRECTION

PATENT NO. : 8,937,193 B2  
APPLICATION NO. : 12/900378  
DATED : January 20, 2015  
INVENTOR(S) : Maurizio Pellecchia and Jun Wei Page 1 of 1

It is certified that error appears in the above-identified patent and that said Letters Patent is hereby corrected as shown below:

In the Specification

In Column 1, Lines 15 through 17, please replace:
"This invention was made in part with government support under NCI-U19, CA113319, and CA149668. The Government has certain rights in the invention."

With:
"This invention was made with government support under CA149668 and CA113319 awarded by the National Institutes of Health. The government has certain rights in the invention."

Signed and Sealed this  
Twenty-third Day of March, 2021

Drew Hirshfeld  
*Performing the Functions and Duties of the*  
*Under Secretary of Commerce for Intellectual Property and*  
*Director of the United States Patent and Trademark Office*